US008883504B2

(12) United States Patent
Miyabayashi et al.

(10) Patent No.: US 8,883,504 B2
(45) Date of Patent: Nov. 11, 2014

(54) CELL DIFFERENTIATION SUPPRESSING AGENT, METHOD OF CULTURING CELLS USING THE SAME, CULTURE SOLUTION, AND CULTURED CELL LINE

(75) Inventors: Tomoyuki Miyabayashi, Fuji (JP); Masashi Yamamoto, Fuji (JP)

(73) Assignee: Asahi Kasei Kabushiki Kaisha, Osaka-Shi (JP)

( * ) Notice: Subject to any disclaimer, the term of this patent is extended or adjusted under 35 U.S.C. 154(b) by 1754 days.

(21) Appl. No.: 12/233,252

(22) Filed: Sep. 18, 2008

(65) Prior Publication Data

US 2009/0155906 A1 Jun. 18, 2009

Related U.S. Application Data

(62) Division of application No. 10/875,194, filed on Jun. 25, 2004, now abandoned.

(30) Foreign Application Priority Data

Jun. 27, 2003 (JP) .................................. 2003-185398
Oct. 14, 2003 (JP) .................................. 2003-353870

(51) Int. Cl.
C12N 5/00 (2006.01)
C07D 217/16 (2006.01)
A61K 31/47 (2006.01)
A61K 31/404 (2006.01)
A61K 31/655 (2006.01)
A61K 31/472 (2006.01)

(52) U.S. Cl.
CPC ............ C07D 217/16 (2013.01); C12N 5/0018 (2013.01); A61K 31/47 (2013.01); A61K 31/404 (2013.01); C12N 2501/999 (2013.01); A61K 31/655 (2013.01); A61K 31/472 (2013.01)
USPC ........... 435/405; 435/404; 435/384; 435/383; 435/377

(58) Field of Classification Search
CPC ............. C12N 5/0606; C12N 2501/31; C12N 2501/392; C12N 5/0603; C12N 5/0018; C12N 9/99; A61K 35/12; A61K 35/48; A61K 35/545; A61K 31/085; A61K 31/138; A61K 31/155; A61K 31/165; A61K 31/185; A61K 31/245; A61K 31/341; A61K 31/34
See application file for complete search history.

(56) References Cited

U.S. PATENT DOCUMENTS

| 4,667,083 | A * | 5/1987 | Stol | 219/136 |
|---|---|---|---|---|
| 6,987,102 | B2 * | 1/2006 | Bridger et al. | 514/183 |
| 7,892,830 | B2 * | 2/2011 | Bergendahl et al. | 435/384 |
| 2003/0082810 | A1 | 5/2003 | Serup et al. | |
| 2004/0028660 | A1 | 2/2004 | Hariri et al. | |
| 2004/0097408 | A1 | 5/2004 | Leder et al. | |
| 2005/0260748 | A1 * | 11/2005 | Chang et al. | 435/366 |
| 2006/0195918 | A1 | 8/2006 | Lemischka et al. | |
| 2007/1017843 | | 8/2007 | Smith et al. | |

FOREIGN PATENT DOCUMENTS

| JP | 2001-17163 A | 1/2001 |
|---|---|---|
| JP | 2003-111588 A | 4/2003 |
| WO | WO-87/00834 A1 | 2/1987 |
| WO | WO 03/010303 A1 | 2/2003 |
| WO | WO-03/038070 A1 | 5/2003 |
| WO | WO-03/093487 A1 | 11/2003 |
| WO | WO-03/102151 A2 | 12/2003 |
| WO | WO-03/104442 A1 | 12/2003 |

OTHER PUBLICATIONS

Atanes et al., "The Reaction of 1-Alkyldihydroisoquinolines with Benzyne An Unexpected Entry to Dibenzindolizines", Tetrahedron Letters, vol. 28. No. 7. pp. 817-820, April 7, 1967.
Japanesese Office Action dated Jul. 20, 2010, for Japanesese Application No. 2005-518810.
Japanese Office Action for Application No. 2005-511810, dated Oct. 19, 2010.
European Search Report issued on Feb. 16, 2011 in corresponding European Patent Application No. 04746848.3.
Gorbunov et al., "Interaction of 1-Methylthio-3,3-Dimethyl-3,4-Dihydroisoquinoline with β-Dicarboxylic Acids, β-Dicarbonyl Compounds, and Their Analogs", Institute of Technical Chemistry, Jun. 26, 1991 (translated Dec. 1992), pp. 1416-1419.
V. M. Lyubchanskaya et al., "Lactam and Acid Amide Acetals. 71.* New Synthesis of 3-Nitro-6-Hydroxyindole Derivatives", S. Ordzbonikidze Scientific-Research Institute of Pharmaceutical Chemistry, May 4, 1990 (translated Jan. 1992), pp. 34-39.
Korean Office Action dated Oct. 10, 2011 for Korean Patent Application No. 10-2005-7024980.
The EMBO Journal, "STAT3 activation is sufficient to maintain an undifferentiated state of mouse embryonic stem cells", vol. 18, No. 15, pp. 4261-4269, 1999.
James A. Thomson et al.; Proc. Natl. Acad. Sci.; vol. 92; Aug. 1995; pp. 7844-7848.

(Continued)

Primary Examiner — Blaine Lankford
(74) Attorney, Agent, or Firm — Birch, Stewart, Kolasch & Birch, LLP

(57) ABSTRACT

The object of the present invention is to provide a differentiation inhibiting agent which allows culture of a stem cell or an embryonic stem cell in an undifferentiated state without use of any feeder cell, a method for culturing using the same, a cell culture liquid using the same, and a cell prepared by culturing using this differentiation inhibiting agent. The present invention provides a differentiation inhibiting agent which comprises a low molecular weight compound, especially a tetrahydroisoquinoline derivative, as an active ingredient; a method for safely culturing a stem cell in large scale in undifferentiated state in the absence of feeder cell which comprises culturing a stem cell by using a tetrahydroisoquinoline derivative; a culture liquid for stem cells comprising a tetrahydroisoquinoline derivative; and a cell which is obtained by culture using a tetrahydroisoquinoline derivative as a differentiation inhibiting agent.

2 Claims, 19 Drawing Sheets

(56) References Cited

OTHER PUBLICATIONS

James A. Thomson et al.; Nature Biotechnolgy; vol. 282 Nov. 6, 1998; pp. 1145-1147.
Tom Burdon et al., Developmental Biology; vol. 210 18; Apr. 1999; pp. 30-43.
Hirofumi Suemori et al.; Developmental Dynamics; vol. 222; 2001; pp. 273-279.
Chunhui Xu et al., Nature Biotechnology; vol. 19; Oct. 2001; pp. 971-974.
Noboru Sato et al., Nature Medicine; vol. 10; No. 1; Jan. 2004; pp. 55-63.
Aubert et al., Journal of Biological Chemistry, 274(35), 24965-24872, 1999.
Tresini et al., Cancer Research, 58, 1-4, 1998.
Son et al., Journal of Neurochemistry, 79, 1013-1021, 2001.
Lyubchanskaya et al., Chemical Abstracts, 118:233815, 1993.
Lyubchanskaya et al., Chemical Abstracts, 119:160035, 1993.
Panisheva et al., Chemical Abstracts, 110:225040, 1989.
Eiden et al., Chemical Abstract, 82:156071, 1975.
Tsuji-Takayama et al., Biochemical and Biophysical Research Communications, 323, 86-90, 2004.
Mitsui et al., Cell, 113(5), 631-642, 2003.
Hamazaki et al., Molecular and Cellular Biology, 26(20), 7539-7549, 2006.
Chen et al., "Suppression of ES Cell Differentiation by Retinol (Vitamin A) Via the Overexpression of Nanog", Differentiation, 75(8) 682-693, Oct. 2007 (abstract only).

* cited by examiner

| | NAME OF COMPOUND | R¹ | R² | R³ | R⁴ | R⁵ | R⁶ | R⁷ | R⁸ | R⁹ | R¹⁰ | R¹¹ | R¹² |
|---|---|---|---|---|---|---|---|---|---|---|---|---|---|
| A | 2-CYANO-2-(3,3-DIMETHYL-3,4-DIHYDRO-2H-ISOQUINOLINE-1-YLIDENE)-N-P-TOLYL-ACETAMIDE | H | H | H | H | H | Me | Me | H | H | H | H | Me |

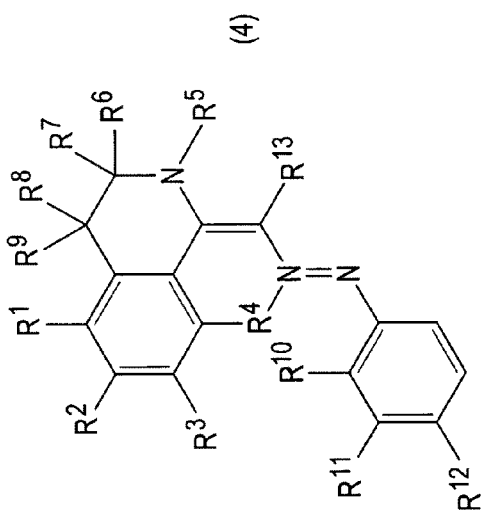

| | NAME OF COMPOUNDS | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ |
|---|---|---|---|---|---|---|---|---|---|---|---|---|---|---|
| B | 2-(4-ACETYL-PHENYLAZO)-2-(3,3-DIMETHYL-3,4-DIHYDRO-2H-ISOQUINOLINE-1-YLIDENE)-ACETAMIDE | H | H | H | H | H | Me | Me | H | H | H | H | Ac | $CONH_2$ |
| C | 2-(3-CHLORO-PHENYLAZO)-2-(3,3-DIMETHYL-3,4-DIHYDRO-2H-ISOQUINOLINE-1-YLIDENE)-ACETAMIDE | H | H | H | H | H | Me | Me | H | H | H | Cl | H | $CONH_2$ |
| D | 2-(3,3-DIMETHYL-3,4-DIHYDRO-2H-ISOQUINOLINE-1-YLIDENE)-2-(3-METHOXYPHENYLAZO)-ACETAMIDE | H | H | H | H | H | Me | Me | H | H | H | OMe | H | $CONH_2$ |
| E | 2-(3,3-DIMETHYL-3,4-DIHYDRO-2H-ISOQUINOLINE-1-YLIDENE)-2-(3-NITRO-PHENYLAZO)-ACETAMIDE | H | H | H | H | H | Me | Me | H | H | H | $NO_2$ | H | $CONH_2$ |
| F | 2-(3,3-DIMETHYL-3,4-DIHYDRO-2H-ISOQUINOLINE-1-YLIDENE)-2-(4-METHOXYPHENYLAZO)-ACETAMIDE | H | H | H | H | H | Me | Me | H | H | H | H | OMe | $CONH_2$ |

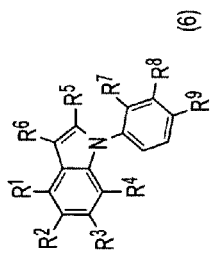

| | | R¹ | R² | R³ | R⁴ | R⁵ | R⁶ | R⁷ | R⁸ | R⁹ |
|---|---|---|---|---|---|---|---|---|---|---|
| a | 2-METHYL-3-NITRO-1-PHENYL-1H-INDOLE-6-OL | -H | -H | -OH | | -Me | -NO₂ | -H | -H | -H |
| b | 1-(4-METHOXY-PHENYL)-2-METHYL-3-NITRO-1H-INDOLE-6-OL | -H | -H | -OH | -H | -Me | -NO₂ | -H | -H | -OMe |
| c | 2-METHYL-3-NITRO-1-P-TOLYL-1H-INDOLE-6-OL | -H | -H | -OH | -H | -Me | -NO₂ | -H | -H | -Me |
| d | 2-{2-(4-METHOXY-PHENYLAMINO)-VINYL}-3-NITRO-1-P-TOLYL-1H-INDOLE-6-OL | -H | -H | -OH | -H | -CH=CHNH-p-METHOXYBENZENE | -NO₂ | -H | -H | -Me |
| e | 1-(2-METHOXY-PHENYL)-2-METHYL-3-NITRO-1H-INDOLE-6-OL | -H | -H | -OH | -H | -Me | -NO₂ | -OMe | -H | -H |
| f | 7-DIMETHYLAMINOMETHYL-2-{2-(DIMETHYLAMINO-VINYL)}-3-NITRO-1-P-TOLYL-1H-INDOLE-6-OL | -H | -H | -OH | -CH₂NMe₂ | -CH=CHNMe₂ | -NO₂ | -H | -H | -Me |
| g | 1-(4-METHOXY-PHENYL)-2-METHYL-3-NITRO-7-PIPERIDINE-1-YLMETHYL-1H-INDOLE-6-OL HYDROCHLORIDE | -H | -H | -OH | -CH₂-PIPERIDINO | -Me | -NO₂ | -H | -H | -OMe |
| h | 2-{2-(DIMETHYLAMINO-VINYL)}-1-(4-METHOXY-PHENYL)-7-MORPHOLINE-4-YLMETHYL-3-NITRO-1H-INDOLE-6-OL | -H | -H | -OH | -CH₂-MORPHOLINO | -CH=CHNMe₂ | -NO₂ | -H | -H | -OMe |
| i | 7-{[(3-HYDROXY-PROPYLAMINO)-METHYL]}-1-(4-METHOXY-PHENYL)-2-METHYL-3-NITRO-1H-INDOLE-6-OL HYDROCHLORIDE | -H | -H | -OH | -CH₂NHCH₂CH₂CH₂OH | -Me | -NO₂ | -H | -H | -OMe |
| j | 7-DIMETHYLAMINOMETHYL-2-{2-(DIMETHYLAMINO-VINYL)}-1-(4-METHOXY-PHENYL)-3-INDOLE-6-OL | -H | -H | -OH | -CH₂NMe₂ | -CH=CHNMe₂ | -NO₂ | -H | -H | -OMe |
| k | 7-DIMETHYLAMINOMETHYL-1-(4-METHOXY-PHENYL)-2-METHYL-3-NITRO-1H-INDOLE-6-OL | -H | -H | -OH | -CH₂NEt₂ | -Me | -NO₂ | -H | -H | -OMe |
| l | 7-DIMETHYLAMINOMETHYL-2-METHYL-3-NITRO-1-P-TOLYL-1H-INDOLE-6-OL | -H | -H | -OH | -CH₂NMe₂ | -Me | -NO₂ | -H | -H | -Me |
| m | 1-(4-METHOXY-PHENYL)-2-METHYL-3-NITRO-7-PIPERIDINE-1-YLMETHYL-1H-INDOLE-6-OL | -H | -H | -OH | -CH₂-PIPERIDINO | -Me | -NO₂ | -H | -H | -OMe |
| n | ACETIC ACID 7-ACETOXYMETHYL-2-METHYL-3-NITRO-1-P-TOLYL-1H-INDOLE-6-YL ESTER | -H | -H | -OAc | -CH₂OAc | -Me | -NO₂ | -H | -H | -Me |
| o | 2-{2-(DIMETHYLAMINO-VINYL)}-1-(4-METHOXY-PHENYL)-3-NITRO-7-PIPERIDINE-1-YLMETHYL-1H-INDOLE-6-OL | -H | -H | -OH | -CH₂-PIPERIDINO | -CH=CHNMe₂ | -NO₂ | -H | -H | -OMe |

| NAME OF COMPOUND | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ |
|---|---|---|---|---|---|---|---|---|---|---|---|---|---|
| | | | | | | | | | | | | | $CONH_2$ |
| | | | | | | | | | | | | Ac | |
| | H | H | H | H | H | Me | Me | H | H | H | H | | |
| ① 2-(4-ACETYL-PHENYLAZO)-2-(3,3-DIMETHYL-1,2,3,4-TETRAHYDRO-ISOQUINOLINE-1-YL)-ACETAMIDE | | | | | | | | | | | | | |

FIG.18

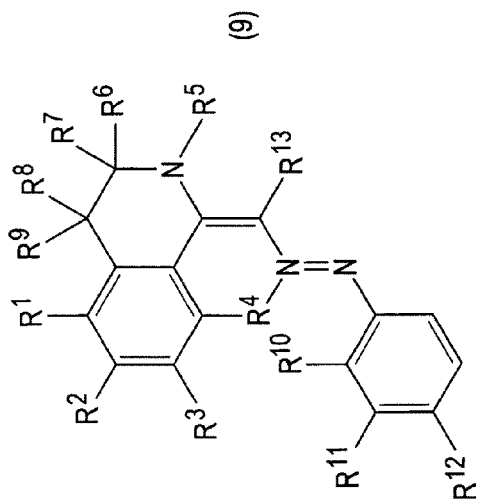

| | NAME OF COMPOUNDS | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ |
|---|---|---|---|---|---|---|---|---|---|---|---|---|---|---|
| ② | (4-ACETYL-PHENYLAZO)-(3,3-DIMETHYL-3,4-DIHYDRO-2H-ISOQUINOLINE-1-YLIDENE)-ACETIC ACID ETHYL ESTER | H | H | H | H | H | Me | Me | H | H | H | H | Ac | $CO_2Et$ |
| ③ | (4-ACETYL-PHENYLAZO)-(3,3-DIMETHYL-3,4-DIHYDRO-2H-ISOQUINOLINE-1-YLIDENE)-ACETONITRILE | H | H | H | H | H | Me | Me | H | H | H | H | Ac | CN |
| ④ | 2-(3-ACETYL-PHENYLAZO)-2-(3,3-DIMETHYL-3,4-DIHYDRO-2H-ISOQUINOLINE-1-YLIDENE)-ACETAMIDE | H | H | H | H | H | Me | Me | H | H | H | Ac | H | $CONH_2$ |
| ⑤ | 2-(4-ACETYL-PHENYLAZO)-2-(3,3-DIMETHYL-3,4-DIHYDRO-2H-ISOQUINOLINE-1-YLIDENE)-N-METHYL-ACETAMIDE | H | H | H | H | H | Me | Me | H | H | H | H | Ac | $CONHMe_2$ |
| ⑥ | 2-(4-ACETYL-PHENYLAZO)-2-(3,3-DIMETHYL-3,4-DIHYDRO-2H-ISOQUINOLINE-1-YLIDENE)-N,N-DIMETHYL-ACETAMIDE | H | H | H | H | H | Me | Me | H | H | H | H | Ac | $CONMe_2$ |
| ⑦ | 2-(4-ACETYL-PHENYLAZO)-2-(3,3-DIMETHYL-3,4-DIHYDRO-2H-ISOQUINOLINE-1-YLIDENE)-N-PHENYL-ACETAMIDE | H | H | H | H | H | Me | Me | H | H | H | H | Ac | CONHPh |
| ⑧ | (4-ACETYL-PHENYLAZO)-2-(3,3-DIMETHYL-3,4-DIHYDRO-2H-ISOQUINOLINE-1-YLIDENE)-ACETIC ACID | H | H | H | H | H | Me | Me | H | H | H | H | Ac | $CO_2H$ |
| ⑨ | 2-(4-ACETYL-PHENYLAZO)-2-(2,3,3-TRIMETHYL-3,4-DIHYDRO-2H-ISOQUINOLINE-1-YLIDENE)-ACETAMIDE | H | H | H | H | Me | Me | Me | H | H | H | H | Ac | $CONH_2$ |
| ⑩ | 2-(2-ACETYL-3,3-DIMETHYL-3,4-DIHYDRO-2H-ISOQUINOLINE-1-YLIDENE)-2-(4-ACETYL-PHENYLAZO)-ACETAMIDE | H | H | H | H | Ac | Me | Me | H | H | H | H | Ac | $CONH_2$ |

CELL DIFFERENTIATION SUPPRESSING AGENT, METHOD OF CULTURING CELLS USING THE SAME, CULTURE SOLUTION, AND CULTURED CELL LINE

This application is a Divisional of application Ser. No. 10/875,194, filed on Jun. 25, 2004, now abandoned and for which priority is claimed under 35 U.S.C. §120; this application claims priority of Application No. 2003-185398 and Application No. 2003-353870 filed in Japan on Jun. 27, 2003 and Oct. 14, 2003, respectively, under 35 U.S.C. §119; the entire contents of all are hereby incorporated by reference.

TECHNICAL FIELD

The present invention relates to a stem cell differentiation inhibiting agent comprising a low molecular weight compound, especially a tetrahydroisoquinoline derivative, as an active ingredient, a stem cell culture method by using the same, a culture medium, and a cultured stem cell line prepared by using the same. The present invention relates further to new bicyclic compounds having an action of maintaining an undifferentiated state of the stem cell.

BACKGROUND ART

An organ and a tissue damaged by an injury, a disease or aging require promotion of regeneration to recover its function. Particularly, a substantial organ such as heart, liver, kidney, or pancreas is essential for maintaining life, and thus hypofunction and a function thereof causes a death. Therefore transplantation treatment such as organ transplantation is popularly conducted intending life saving. However, the number of donor is generally insufficient, and thus a new approach to solve the problem is necessary.

In recent years, regeneration medicine by using a stem cell, which is present in an embryo or an adult and may have an ability of dividing indefinitely to differentiate in one or a plurality of directions, to prepare the tissue and the organ for repairing a defect tissue, attracts attention as a therapeutic method without the defect of the conventional organ transplantation.

Specifically, it is exemplified that following propagation, the stem cell is grown and then differentiated to be used for cell transplantation and, through use of an artificial support tissue and artificial tissue construction, the artificial tissue is transplanted into a living body and is used as an artificial organ. It is expected that using the stem cell for cell transplantation therapy and tissue engineering allows solving the problem, which includes a defect of a tissue after a transplanting piece is resected from the donor and the shortage of the donor, in transplantation therapy including conventional autotransplantation.

The stem cell has been identified from many organs such as a blood vessel, nerve, blood, cartilage, bone, liver, pancreas. Particularly among them, a totipotent stem cell having the ability of differentiating in all cell types gets a lot of attention as a cell that can provide easily a cell and a tissue used for the aforementioned regeneration medicine field and also drug creation and gene therapy.

Known examples of the totipotent stem cell are Embryonic Stem (hereafter ES) cell and Embryonic Germ (hereafter EG) cell. The ES cell is a cell line isolated from an Inner Cell Mass (ICM) of a blastocyst stage of a mouse (Evans et al., Nature, 292: 154, 1981). Cells consisting an individual are derived from a primary ectoderm produced from an Inner Cell Mass (hereafter ICM) of the blastocyst stage or an epiblast of a gastrula, and the ICM and the epiblast are a stem cell group having the totipotency. The ES cell has the ability of the differentiation into various kinds of tissues to form the individual and forms a normal embryo and a chimeric embryo to differ into any mature cells of the adult. In addition, the ES cell has the ability of producing such various cells as blood cells, myocardial cell, vascular endothelial cell, nerve cell, pigment cell, pancreatic incretion cell depending on the condition of in vitro differentiation induction (Nakano, T. Saisin Igaku Bessatsu Regeneration medicine: 81-89. 2000).

The EG cell is a cell line established by culturing a primordial germ cell in presence of LIF (Leukemia Inhibitory Factor) and bFGF (basic Fibroblast Growth Factor) (Matsui et al., Cell 70: 84. 1992; Resnic et al., Nature 359: 550. 1992) and has ability of differentistion into various tissues as in the case of the ES cell.

In recent years, the ES cell lines established in animals other than the mouse were reported, and it was shown that they have multidifferentiation ability similar to that of the mouse ES cell (bovine ES cell: Schellander et al., Theriogenology, 31: p15-17, 1989, swine ES cell: Strojek et al., Theriogenology 33: p901, 1990, sheep ES cell: primate Handyside, Roux's Arch. De v. Biol., 196: p185, 1987, hamster ES cell: Doetschman et al., Dev. Biol., 127: p224, 1988, Rhesus macaque ES cell: Thomson et al., Proc. Natl. Acad. Sci. USA, 92: p7844, 1995, marmoset ES cell: Thomson et al., Biology of Production 55: p254, 1996, human ES cell: Thomson et al., Science, 282: p1145, 1998, Reubinoff et al., Nature Biotech 18: p399, 2000, cynomolgus monkey ES cell: Suemori et al., Dev. Dyn. 222: p273, 2001).

In order to maintain undifferentiation of the ES cell, it is generally necessary to co-culture a fibroblast originated from a mouse fetus as a feeder cell. The same method is used for maintaining undifferentiation of the ES cell line of a primate (Thomson et al., Proc. Natl. Acad. Sci. USA 92: p7844, 1995, Thomson et al., Science: 282: p1145, 1998, Reubinoff et al., Nature Biotech 18: p399, 2000).

However, preparation of the mouse primary fibroblast is complicated as follows. A 13.5 to 15.5-day old embryo is taken out from a pregnant mouse, the embryo is degraded by enzyme treatment, and the fibroblast yielded is collected on a dish. Since this cell is primary cell, quality management is complicated, management on a GMP-matched level is difficult, and the ability of maintaining undifferentiation may be different depending on the embryo used. As an ES cell culture method without this complicated preparation work, there is a method of using an STO cell (ATCC 56-X) which is a cell line of the fibroblast of a mouse embryo. However, the STO cell's ability of maintaining undifferentiation of the ES cell is variable, and thus, for stable culture of the ES cell, the mouse primary fibroblast is superior.

In recent years, an infection case of an endogenous virus across different animal species was reported (van der Laan et al., Nature 407: p90, 2000). The culture method aiming use of the human ES cell for medicine requires developing the culture method without contact between cells of different animal species as possible. Therefore, the above culture method for maintaining undifferentiation of the ES cell by using cells derived from the mouse is not suitable for culturing the ES cell aiming to use for medicine.

As the method for culturing a primate ES cell using no mouse-derived feeder cell, a method of adding a component secreted by the mouse primary fibroblast to a culture medium has been reported (for example, Japanese Patent Laid-open Publication No. 2001-17163). However, also in this case, the ES cell under culturing is exposed to an unidentified factor secreted from the mouse cell, and therefore the ES cell cultured in such an environment is not suitable for the use in medicine. Moreover, a danger of infection of the endogenous virus remains Consequently, the defect caused by coculture with the mouse primary fibroblast is not solved at all.

As the method for culture for maintaining undifferentiation of the mouse ES cell without using the mouse-derived feeder cell and the component secreted by the mouse feeder cell, a culture method of using a culture dish coated with gelatin has been already known. However, in this method, leukemia inhibitory factor (LIF) must be added to the culture medium (for example, Smith et al., Dev. Biol. 121: p1, 1987). LIF is a cytokine and therefore, has problems of high cost and a bad preservation performance, resulting in unsuitableness for mass culture. In addition, an effect of LIF is limited to the ES cell derived from a very specific mouse line (129/sv line and C57BL/6 line) and shows no distinct effect on animals of other species. Especially, for the primate ES cell, it has been known that addition of LIF to the culture medium alone does not allow keeping the undiffentiation status (for example, Thomson et al., Proc. Natl. Acad. Sci. USA 92: p7844, 1995; and Thomson et al., Science 282: p1145, 1998).

On the other hand, as a low molecular weight compound which amplifies an LIF's action of maintaining undifferentiation of an embryonic stem cell, PD98059 (Cell Signaling Technology Corp. made) is reported. However, the action of PD98059 depends on LIF and does not express independently the effect (Burdon et al., Dev. Biol. 210: p30, 1999) and, hence, the aforementioned problem is not solved.

Consequently, so far, there was no differentiation inhibiting agent enabling safe mass culture of the totipotent stem cell at a low cost, and no method of safe mass culture of the totipotent stem cell at the low cost has been known. The differentiation inhibiting agent according to the present invention comprises a low molecular weight compound as the active ingredient. It has been not so far known that a low molecular weight compound maintains the undifferentiated status of the totipotent stem cell. Therefore, the action of maintaining undifferentiation of the totipotent stem cell which is possessed by the low molecular weight compound represented by the formulae (1) to (10) shown in this specification, has not been known at all so far.

DISCLOSURE OF THE INVENTION

The object of the present invention is to provide a differentiation inhibiting agent which allows culture of a stem cell or an embryonic stem cell in an undifferentiated state without use of any feeder cell or any component derived from the feeder cell. In addition, the object of the present invention is to provide a method for culturing the stem cell or the embryonic stem cell in an undifferentiated state by using such the differentiation inhibiting agent without use of any feeder cell or any component derived from the feeder cell, and to provide a cell culture liquid which comprises such the differentiation inhibiting agent, and to provide a cell line prepared by culturing using such the differentiation inhibiting agent. Further another object of the present invention is to provide a novel bicyclic compound enabling culture of the stem cell or the embryonic stem cell in the undifferentiated state without use of any feeder cell or any component derived from the feeder cell.

The present invention was achieved to solve the above objects and relates to a differentiation inhibiting agent allowing culture of a stem cell or an embryonic stem cell in an undifferentiated state, a method for culturing the stem cell or the embryonic stem cell by using such the differentiation inhibiting agent, a cell culture liquid comprising such the differentiation inhibiting agent, and a cell line prepared by culturing using such the differentiation inhibiting agent.

Thus, the present invention includes the followings:
(1) A stem cell differentiation inhibiting agent which comprises a low molecular weight compound or a salt thereof as an active ingredient.
(2) The stem cell differentiation inhibiting agent according to (1) above, wherein the low molecular weight compound is a compound represented by the formula (1):

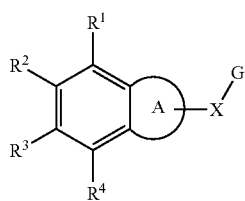

(1)

wherein, $R^1$, $R^2$, $R^3$ and $R^4$ may be the same or different, each representing an electron-withdrawing group, an electron-donating group or a hydrogen atom; ring A represents 5- to 8-member ring containing at least 1 hetero atom in the ring; X represents an alkylene group of which atomic number of a main chain ranges from 0 to 10; the alkylene group having the atomic number of 0 represents a single bond; one or more ethylene groups constituting the alkylene group may be replaced by —C=C— group, and/or —N=N— group, and/or —CONH— group, and further the group may have a double bond bonding to the ring A; the alkylene group has 1 or more electron-withdrawing groups, electron-donating groups or hydrogen atoms as a substituent; G represents an aromatic group which may have an electron-withdrawing group, an electron-donating group or a hydrogen atom; the ring A may have 1 or more electron-withdrawing group and/or an electron-donating group as a substituent other than an —XG group.

(3) The stem cell differentiation inhibiting agent according to (2) above, wherein the ring A is a 5- or 6-member ring containing at least 1 hetero atom selected from a group consisting of a nitrogen atom, an oxygen atom and a sulfur atom, in the ring.

(4) The stem cell differentiation inhibiting agent according to (2) above, wherein the ring A is a 5- or 6-member ring containing 1 nitrogen atom in the ring.

(5) The stem cell differentiation inhibiting agent according to any of (2) to (4) above, wherein the alkylene group represented by X includes 1 or more groups and/or atoms selected from the group consisting of an alkyl group, an acyl group, an alkoxy group, a nitro group, a hydroxycarbonyl group, an alkoxycarbonyl group, an aminocarbonyl group, a nitrile group and a halogen atom as a substituent.

(6) The stem cell differentiation inhibiting agent according to (2) above, wherein the low molecular weight compound is a compound represented by the formula (2):

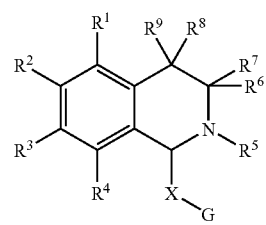

(2)

wherein $R^1$, $R^2$, $R^3$, $R^4$, X and G are the same as those defined in (2) above, and $R^5$, $R^6$, $R^7$, $R^8$ and $R^9$ may be the same or different, each representing an electron-withdrawing group, an electron-donating group or a hydrogen atom.

(7) The stem cell differentiation inhibiting agent according to (2) above, wherein the low molecular weight compound is a compound represented by the formula (3):

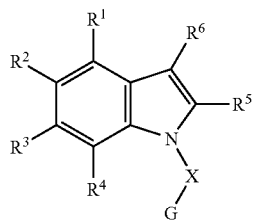

(3)

wherein $R^1$, $R^2$, $R^3$, $R^4$, X and G are the same as those defined in (2) above; $R^5$ and $R^6$ may be the same or different, each representing an electron-withdrawing group, an electron-donating group or a hydrogen atom.

(8) The stem cell differentiation inhibiting agent according to (6) above, wherein the low molecular weight compound is a compound represented by the formula (4):

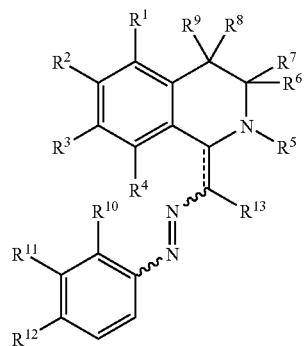

(4)

wherein $R^1$, $R^2$, $R^3$, $R^4$, $R^5$, $R^6$, $R^7$, $R^8$ and $R^9$ are the same as those defined in (6) above; $R^{10}$, $R^{11}$, $R^{12}$ and $R^{13}$ may be the same or different, each representing an electron-withdrawing group, an electron-donating group or a hydrogen atom; the double one-side broken line represents a single bond or a double bond; when the double one-side broken line represents a double bond, a wavy portion represents the presence of a geometric isomer; arrangement of these geometric isomers is not specially restricted, but may be any of an E isomer or a Z isomer each independently.

(9) The stem cell differentiation inhibiting agent according to (8) above, wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently groups or atoms selected from the group consisting of an alkyl group, an acyl group, an alkoxy group, a nitro group, a hydroxycarbonyl group, a nitrile group, an alkoxycarbonyl group, an aminocarbonyl group, a halogen atom and a hydrogen atom.

(10) The stem cell differentiation inhibiting agent according to (6) above, wherein the low molecular weight compound is a compound represented by the formula (5):

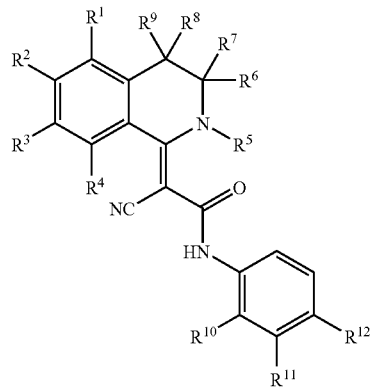

(5)

wherein $R^1$, $R^2$, $R^3$, $R^4$, $R^5$, $R^6$, $R^7$, $R^8$ and $R^9$ are the same as those defined in (6) above; $R^{10}$, $R^{11}$ and $R^{12}$ may be the same or different, each representing an electron-withdrawing group, an electron-donating group or a hydrogen atom.

(11) The stem cell differentiation inhibiting agent according to (10) above, wherein $R^1$, $R^2$, $R^3$, $R^4$, $R^5$, $R^6$, $R^7$, $R^8$, $R^9$, $R^{10}$, $R^{11}$ and $R^{12}$ are each independently groups or atoms selected from the group consisting of an alkyl group, an acyl group, an alkoxy group, a nitro group, a hydroxycarbonyl group, a nitrile group, an alkoxycarbonyl group, an aminocarbonyl group, a halogen atom and a hydrogen atom.

(12) The stem cell differentiation inhibiting agent according to (7) above, wherein the low molecular weight compound is a compound represented by the formula (6):

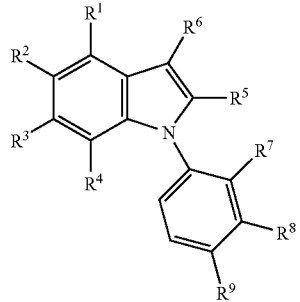

(6)

wherein $R^1$, $R^2$, $R^3$, $R^4$, $R^5$ and $R^6$ are the same as those defined in (7) above; $R^7$, $R^8$ and $R^9$ may be the same or different, each representing an electron-withdrawing group, an electron-donating group or a hydrogen atom.

(13) The stem cell differentiation inhibiting agent according to (12) above, wherein $R^1$, $R^2$, $R^3$, $R^4$, $R^5$, $R^6$, $R^7$, $R^8$ and $R^9$ are each independently groups or atoms selected from the group consisting of an alkyl group, an alkoxy group, a hydroxyl group, a nitro group, a nitrile group, an acetoxy group, an acetoxy alkyl group, a cyclic alkylaminoalkyl group which may contain an oxygen atom, a dialkylaminoalkyl group, a dialkylaminovinyl group, a hydroxyalkylaminoalkyl group, an arylaminovinyl group and a hydrogen atom.

(14) The stem cell differentiation inhibiting agent according to (8) above, wherein $R^1$, $R^2$, $R^3$, $R^4$, $R^8$, $R^9$ and $R^{10}$ are hydrogen atoms; $R^5$ is a hydrogen atom, a lower acyl group or a lower alkyl group; $R^6$ and $R^7$ are lower alkyl groups which may be the same or different; $R^{11}$ is a hydrogen atom, a halogen atom, a nitro group or a lower alkoxy group; $R^{12}$ is a hydrogen atom, a lower alkyl group, a lower acyl group or a lower alkoxy group; and $R^{13}$ is a hydroxycarbonyl group, a nitrile group, an aminocarbonyl group or a lower alkoxycarbonyl group.

(15) The stem cell differentiation inhibiting agent according to (10) above, wherein $R^1$, $R^2$, $R^3$, $R^4$, $R^8$ and $R^9$ are hydrogen atoms; $R^5$ is a hydrogen atom, a lower acyl group or a lower alkyl group; $R^6$ and $R^7$ are lower alkyl groups which may be the same or different; $R^{10}$ is a hydrogen atom or a lower alkyl group; $R^{11}$ is a hydrogen atom, a halogen atom, a nitro group, a lower alkoxy group or a lower alkoxycarbonyl group; and $R^{12}$ is a hydrogen atom, a lower alkyl group, a lower acyl group or a lower alkoxy group.

(16) The stem cell differentiation inhibiting agent according to (12) above, wherein $R^1$ and $R^2$ are hydrogen atoms; $R^3$ is a hydroxyl group or an acetoxy group; $R^4$ is an acetoxy alkyl group, a cyclic alkylaminoalkyl group which may contain an oxygen atom, a dialkylaminoalkyl group, a hydroxyalkylamiioalkyl group or a hydrogen atom; $R^5$ is a lower alkyl group or an arylaminovinyl group; $R^6$ is a nitro group; $R^7$, $R^8$ and $R^9$ may be the same or different, each representing a lower alkyl group, a lower alkoxy group or a hydrogen atom.

(17) A compound represented by the formula (9), or a salt thereof.

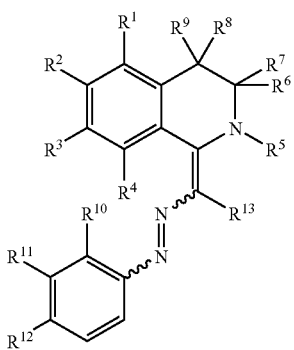

(9)

wherein $R^1$, $R^2$, $R^3$ and $R^4$ may be the same or different, each representing a hydrogen atom, a lower alkyl group, a hydroxyl group, a lower alkoxy group or a halogen atom; $R^5$ is a hydrogen atom, a lower acyl group or a lower alkyl group; $R^6$ and $R^7$ may be the same or different, each representing a hydrogen atom, a lower alkyl group or a lower alkyl group which may form a ring structure; $R^8$ and $R^9$ are hydrogen atoms; $R^{10}$, $R^{11}$ and $R^{12}$ may be the same or different, each representing a hydrogen atom, a halogen atom, a nitro group, a lower alkyl group, a lower acyl group or a lower alkoxy group; $R^{13}$ represents a hydroxycarbonyl group; a lower alkoxycarbonyl group, a secondary aminocarbonyl group or a tertiary aminocarbonyl group; the wavy lined portion represents the presence of the geometric isomer; arrangement of these geometric isomers is not specially restricted, but may be any of the E isomer or the Z isomer each independently.

(18) The compound represented by the formula (9), or a salt thereof.

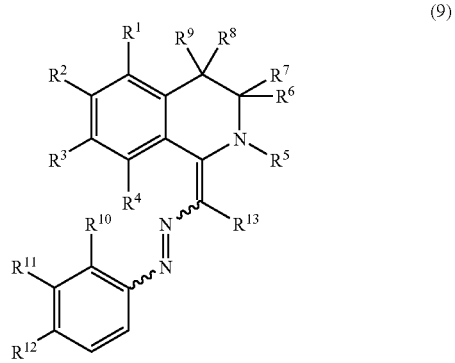

(9)

wherein $R^1$, $R^2$, $R^3$ and $R^4$ may be the same or different, each representing a hydrogen atom, a lower alkyl group, a hydroxyl group, a lower alkoxy group or a halogen atom; $R^5$ is a hydrogen atom, a lower acyl group or a lower alkyl group; $R^6$ and $R^7$ may be the same or different, each representing a hydrogen atom, a lower alkyl group or a lower alkyl group which may form a ring structure; $R^8$ and $R^9$ are hydrogen atoms; $R^{10}$ and $R^{12}$ are a hydrogen atom, a halogen atom, a nitro group, a lower alkyl group, a lower acyl group or a lower alkoxy group; $R^{11}$ is a lower acyl group; $R^{13}$ represents a hydroxycarbonyl group, a lower alkoxycarbonyl group or an aminocarbonyl group; the wavy lined portion represents the presence of the geometric isomer; arrangement of these geometric isomers is not specially restricted, but may be any of the E isomer or the Z isomer each independently.

(19) The compound represented by the formula (9), or a salt thereof.

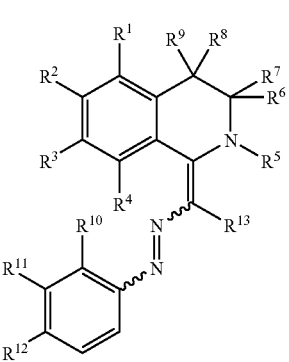

(9)

wherein $R^1$, $R^2$, $R^3$ and $R^4$ may be the same or different, each representing a hydrogen atom, a lower alkyl group, a hydroxyl group, a lower alkoxy group or a halogen group; $R^5$ is a lower acyl group or a lower alkyl group; $R^6$ and $R^7$ may be the same or different, each representing a hydrogen atom, a lower alkyl group or a lower alkyl group which may form a ring structure; $R^8$ and $R^9$ are hydrogen atoms; $R^{10}$, $R^{11}$ and $R^{12}$ may be the same or different, each representing a hydrogen atom, a halogen atom, a nitro group, a lower alkyl group, a lower acyl group or a lower alkoxy group; $R^{13}$ represents a hydroxycarbonyl group, a lower alkoxycarbonyl group or an aminocarbonyl group; the wavy lined portion represents the presence of the geometric isomer; Arrangement of these geometric isomers is not specially restricted, but may be any of the E isomer or the Z isomer each independently.
(20) The compound represented by the formula (9), or a salt thereof.

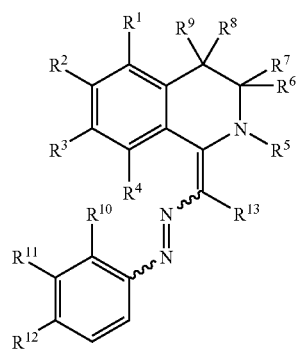

wherein $R^1$, $R^2$, $R^3$ and $R^4$ may be the same or different, each representing a hydrogen atom, a lower alkyl group, a hydroxyl group, a lower alkoxy group or a halogen atom; $R^5$ is a hydrogen atom, a lower acyl group or a lower alkyl group; $R^6$ and $R^7$ may be the same or different, each representing a lower alkyl group or a lower alkyl group which may form a ring structure; $R^8$ and $R^9$ are hydrogen atoms; $R^{10}$, $R^{11}$ and $R^{12}$ may be the same or different, each representing a hydrogen atom, a halogen atom, a nitro group, a lower alkyl group, a lower acyl group or a lower alkoxy group; $R^{13}$ represents a nitrile group; the wavy lined portion represents the presence of the geometric isomer; arrangement of these geometric isomers is not specially restricted, but may be any of the E isomer or the Z isomer each independently.
(21) The compound represented by the formula (10), or a salt thereof.

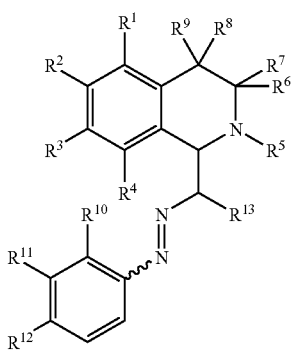

wherein $R^1$, $R^2$, $R^3$ and $R^4$ may be the same or different, each representing a hydrogen atom, a lower alkyl group, a hydroxyl group, a lower alkoxy group or a halogen atom; $R^5$ is a hydrogen atom, a lower acyl group or a lower alkyl group; $R^6$ and $R^7$ may be the same or different, each representing a hydrogen atom, a lower alkyl group or a lower alkyl group which may form a ring structure; $R^8$ and $R^9$ are hydrogen atoms; $R^{10}$, $R^{11}$ and $R^{12}$ may be the same or different, each representing a hydrogen atom, a halogen atom, a nitro group, a lower alkyl group, a lower acyl group or a lower alkoxy group; and $R^{13}$ represents a hydroxycarbonyl group, a lower alkoxycarbonyl group, an aminocarbonyl group or a nitrile group.

(22) The compound according to (17) above or a salt thereof, wherein $R^1$, $R^2$, $R^3$ and $R^4$ are hydrogen atoms; $R^5$ is a hydrogen atom, a lower acyl group or a lower alkyl group; $R^6$ and $R^7$ are lower alkyl groups which may be same or different from each other; $R^8$, $R^9$ and $R^{10}$ are hydrogen atoms; $R^{11}$ and $R^{12}$ may be the same or different, each representing a hydrogen atom, a halogen atom, a nitro group, a lower alkyl group, a lower acyl group or a lower alkoxy group; and $R^{13}$ is a hydroxycarbonyl group, a lower alkoxycarbonyl group, a mono-lower alkylaminocarbonyl group, a di-lower alkylaminocarbonyl group or a phenyl aminocarbonyl group.
(23) The compound according to (18) above or a salt thereof, wherein $R^1$, $R^2$, $R^3$ and $R^4$ are hydrogen atoms; $R^5$ is a hydrogen atom, a lower acyl group or a lower alkyl group; $R^6$ and $R^7$ are lower alkyl groups which may be the same or different; $R^8$, $R^9$ and $R^{10}$ are hydrogen atoms; $R^{11}$ is a lower acyl group; $R^{12}$ is a hydrogen atom, a halo-en atom, a nitro group, a lower alkyl group, a lower acyl group or a lower alkoxy group; and $R^{13}$ is a hydroxycarbonyl group, a lower alkoxycarbonyl group, a carbamoyl group, a mono-lower alkylaminocarbonyl group, a di-lower alkylaminocarbonyl group or a phenyl aminocarbonyl group, or a salt thereof.
(24) The compound according to (19) above or a salt thereof, wherein $R^1$, $R^2$, $R^3$ and $R^4$ are hydrogen atoms; $R^5$ is a lower acyl group or a lower alkyl group; $R^6$ and $R^7$ are lower alkyl groups which may be the same or different; $R^8$, $R^9$ and $R^{10}$ are hydrogen atoms; $R^{11}$ and $R^{12}$ may be the same or different, each representing a hydrogen atom, a halogen atom, a nitro group, a lower alkyl group, a lower acyl group or a lower alkoxy group; and $R^{13}$ is a hydroxycarbonyl group, a lower alkoxycarbonyl group, a carbamoyl group, a mono-lower alkylaminocarbonyl group, a di-lower alkylaminocarbonyl group or a phenyl aminocarbonyl group.
(25) The compound according to (20) above or a salt thereof, wherein $R^1$, $R^2$, $R^3$ and $R^4$ are hydrogen atoms; $R^5$ is a hydrogen atom, a lower acyl group or a lower alkyl group; $R^6$ and $R^7$ are lower alkyl groups which may be the same or different; $R^8$, $R^9$ and $R^{10}$ are hydrogen atoms; $R^{11}$ and $R^{12}$ may be the same or different, each representing a hydrogen atom, a halogen atom, a nitro group, a lower alkyl group, a lower acyl group or a lower alkoxy group; and $R^{13}$ is a nitrile group.
(26) The compound according to (21) above or a salt thereof, wherein $R^1$, $R^2$, $R^3$ and $R^4$ are hydrogen atoms; $R^5$ is a hydrogen atom, a lower acyl group or a lower alkyl group; $R^6$ and $R^7$ are lower alkyl groups which may be the same or different; $R^8$, $R^9$ and $R^{10}$ are hydrogen atoms; $R^{11}$ and $R^{12}$ may be the same or different, each representing a hydrogen atom, a halogen atom, a nitro group, a lower alkyl group, a lower acyl group or a lower alkoxy group; and $R^{13}$ is a hydroxycarbonyl group, a lower alkoxycarbonyl group, a carbonyl group, a mono-lower alkylammiocarbonyl group, a di-lower alkylaminocarbonyl group, a phenyl aminocarbonyl group or a nitrile group.
(27) The compound according to (17) above or a salt thereof, which is (4-acetyl-phenylazo)-(3,3-dimethyl-3,4-dihydro-2H-isoquinoline-1-ylidene)-acetic acid ethyl ester,
(4-acetyl-phenylazo)-(3,3-dimethyl-3,4-dihydro-2H-isoquinoline-1-ylidene)-acetic acid, 2-(4-acetyl-phenylazo)-2-(3,3-dimethyl-3,4-dihydro-2H-isoquinoline-1-ylidene)-N-meth yl-acetamide,
2-(4-acetyl-phenylazo)-2-(3,3-dimethyl-3,4-dihydro-2H-isoquinoline-1-ylidene)-N,N-di methyl-acetamide, or
2-(4-acetyl-phenylazo)-2-(3,3-dimethyl-3,4-dihydro-2H-isoquinoline-1-ylidene)-N-phenyl-acetamide.
(28) The compound according to (18) above or a salt thereof, which is 2-(3-acetyl-phenylazo)-2-(3,3-dimethyl-3,4-dihydro-2H-isoquinoline-1-ylidene)-acetamide.

(29) The compound according to (19) above or a salt thereof, which is 2-(4-acetyl-phenylazo)-2-(2,3,3-trimethyl-3,4-dihydro-2H-isoquinoline-1-ylidene)-acetamide, or 2-(2-acetyl-3,3-dimethyl-3,4-dihydro-2H-isoquinoline-1-ylidene)-2-(4-acetyl-phenylazo)-acetamide.
(30) The compound according to (20) above or a salt thereof, which is (4-acetyl-phenylazo)-(3,3-dimethyl-3,4-dihydro-2H-isoquinoline-1-ylidene)-acetonitrile.
(31) The compound according to (21) above or a salt thereof, which is 2-(4-acetyl-phenylazo)-2-(3,3-dimethyl-1,2,3,4-tetrahydro-isoquinoline-1-yl)-acetamide.
(32) A stem cell differentiation inhibiting agent which comprises the compound according to any of (17) to (31) above or a salt thereof as an active ingredient.
(33) The stem cell differentiation inhibiting agent according to any of (1) to (16) or (32) above wherein the low molecular weight compound is the compound having an action of keeping or increasing an activity of alkaline phosphatase.
(34) The stem cell differentiation inhibiting agent according to any of (1) to (16), (32) or (33) above wherein the low molecular weight compound is a compound which does not activate STAT3 (signal transducer and activator of transcription 3).
(35) The stem cell differentiation inhibiting agent according to any of (1) to (16) or (32) to (34) above wherein the low molecular weight compound is a compound having an action of increasing an SSEA-1 antigen expression level.
(36) The stem cell differentiation inhibiting agent according to any of (1) to (16) or (32) to (35) above wherein the low molecular weight compound is a compound having an action of increasing an Nanog gene expression level.
(37) The stem cell differentiation inhibiting agent according to (36) above wherein the low molecular weight compound is a bicyclic compound having an action of increasing the Nanog gene expression level.
(38) The stem cell differentiation inhibiting agent according to (37) above wherein the low molecular weight compound is a bicyclic compound containing an azo group which has an action of increasing the Nanog gene expression level.
(39) A method for culturing a stem cell, wherein the stem cell is cultured in an undifferentiated state by using the stem cell differentiation inhibiting agent according to any of (1) to (16) or (32) to (38) above.
(40) A method for culturing an embryonic stem cell, wherein the embryonic stem cell is cultured in the undifferentiated state by using the stem cell differentiation inhibiting agent according to any of (1) to (16) or (32) to (38) above.
(41) A culture medium containing the stem cell differentiation inhibiting agent according to any of (1) to (16) or (32) to (38) above as an active ingredient.
(42) A culture medium containing the compound according to any of (17) to (31) above, or a salt thereof.
(43) The culture medium according to (41) or (42) above, wherein the concentration of the differentiation inhibiting agent, the compound, or the salt thereof ranges from 10 ng/mL to 100 μg/mL.
(44) A stem cell cultured in the undifferentiated state by using the differentiation inhibiting agent according to any of (1) to (16) or (32) to (38) above.
(45) A cell or a tissue which is obtained by differentiating a stem cell cultured in the undifferentiated state by using the differentiation inhibiting agent according to any of (1) to (16) or (32) to (38) above.
(46) The cell or the tissue according to (44) or (45) above, wherein the cell or the tissue is used for in vivo transplantation.
(47) A therapeutic method wherein the cell or/and the tissue according to any of (44) to (46) above is subjected to in vivo transplantation.
(48) A prodrug of the compound according to any of (17) to (31) above or a salt thereof.
(49) A pharmaceutical composition comprising the compound according to any of (17) to (31) above or a salt thereof or a prodrug thereof.

BRIEF DESCRIPTION OF THE DRAWINGS

FIG. 2 shows structures of compounds B to F according to the present invention. The compounds B to F are compounds in which $R^1$ to $R^{13}$ of the formula (4) in FIG. 2 are represented by groups or elements presented in the table below.
FIG. 9 shows structures of compounds a to o according to the present invention. For the compounds a to o, $R^1$ to $R^9$ of formula (6) in FIG. 9 are represented by groups or elements presented in the table below.
FIG. 18 shows structure of compound 2̂ to 1̂0̂ according to the present invention. For compounds 2̂ to 1̂0̂, $R^1$ to $R^{13}$ of formula (9) in FIG. 18 are represented by groups or elements presented in the table below.

BEST MODE FOR CARRYING OUT THE INVENTION

Figure 1:
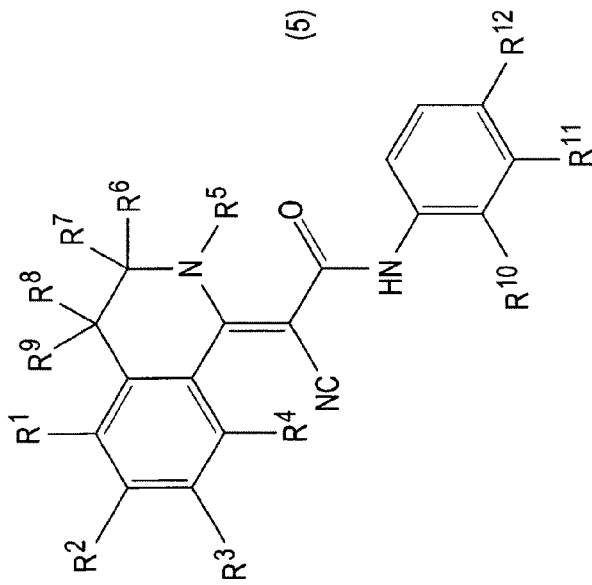
FIG. 1 shows structure of the compound A according to the present invention. The compound A is a compound in which $R^1$ to $R^{12}$ of the formula (5) in FIG. 1 are represented by groups or elements presented in the table below.

Hereinafter, the present invention will be described in detail.
The following technical terms are, unless elsewhere stated, defined as provided below.
All other technical terms used in this specification are, unless otherwise stated, defined regarding usages in specific technical fields related to those terms.

Stem cell: stem cell is a cell differentiable into other cell types, which are differentiable into other cell types having a specified function, in other words, finally differentiated cells or cell types in a narrower range.

Totipotent stem cell: totipotent stem cell is a cell differentiable into arbitrary cell types including multipotent cells or completely differentiated cells (in other words, cells that can no longer differentiate into various cells).

Multipotent stem cell: multipotent stem cell is a cell differentiable into not always all types but one of many different cell types. An example of the multipotent stem cells is a hematopoietic stem cell and this cell can differentiate into various blood cell types such as a lymphocyte and an erythrocyte.

Embryonic stem cell: embryonic stem cell is a totipotent cell obtained from a morula or a blastocyst stage of an embryo particularly in a preimplantation phase among the stem cells, and also called ES cell. The embryonic stem cell is occasionally applied to the multipotent stem cell, which is determined as become a sperm or an ovum, originated from a primordial germ cell of the embryo or the fetus (young). However, this cell is occasionally called an Embryonic Germ (EG) cell, and may be distinguished from the embryonic stem cell. Embryonic stem cells used in this specification may be of any animal species and, for example, include the embryonic stem cells of primates including a human, and mammals other than primates such as mammals and avian.

Totipotency: totipotency is a state differentiable into arbitrary cell types including the multipotent cell or the completely differentiated cell (in other words, cells that can no longer differentiate into various cells).

Multipotency: multipotency is a state differentiable into not always all types but one of many different cell types.

Undifferentiation: undifferentiation is a state in which an arbitrary cell mass comprising 1 cell or a plurality of cells is a cell in a state of having an ability of differentiating into 1 or a plurality of cells in a further differentiated state, or a cell mass containing the cell.

Feeder: feeder used in an aim of describing the present invention is that providing an environment in which the totipotent stem cell is plated thereon to help propagation of the plated totipotent stem cell.

Feeder cell: feeder cell used in an aim of describing the present invention is a nontotipotent stem cell, on which the totipotent stem cell is plated, and the nontotipotent stem cell provides an environment to help propagation of the plated totipotent stem cell.

Component derived from a cell: all components derived from a cell, such as components secreted from the cell, contents and cell membrane components.

The present invention provides a differentiation inhibiting agent allowing propagation and maintenance of the stem cell preferably an embryonic stem cell in a undifferentiated state, a culture method by using the differentiation inhibiting agent, a cell culture liquid prepared by using the differentiation inhibiting agent, and a cell line prepared by culturing the differentiation inhibiting agent. The differentiation inhibiting agent, the culture method, and the culture liquid provided according to the present invention propagate and maintain the undifferentiated embryonic stem cell more conveniently and safely than conventional. The culture method by using the differentiation inhibiting agent according to the present invention may also be used for screening regarding a specific differentiation-inducing factor and a useful combination of differentiation-inducing factors. The ability of propagating the undifferentiated embryonic stem cell by using the differentiation inhibiting agent and the culture method according to the present invention provides an important benefit including the ability of producing an embryonic stem cell line which has a single or a plurality of genetic modifications applicable importantly to a medical treatment.

The differentiation inhibiting agent according to the present invention is a chemically stable low molecular weight compound. Any compound having an activity of maintaining the undifferentiated state of the stem cell can be used. However, preferably, the low molecular weight compound is exemplified by a compound represented by the following formula (1):

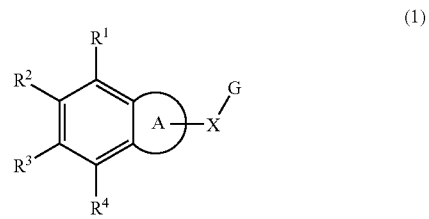

(1)

wherein $R^1$, $R^2$, $R^3$ and $R^4$ may be the same or different, each representing an electron-withdrawing group, an electron-donating group or a hydrogen atom. The electron-donating group is a substituent which can donate an electron to a benzene ring, and the electron-withdrawing group is a substituent having a property of withdrawing a π electron on a benzene ring. By using Hammett's substituent constant s, the electron-donating group and the electron-withdrawing group can be defined as s<0 and s>0, respectively (Kiso Yuuki Hannou Ron (Fundamental Theory of Organic Chemistry), Hasimoto et al., Sankyou Syuppan, 1997).

The ring A represents a 5- to 8-member ring containing at least 1 hetero atom in the ring.

X represents an alkylene group having the atom number of a main chain ranging from 0 to 10. The alkylene group having the atom number 0 means a single bond. 1 or more ethylene constituting the alkylene group may be substituted by —C═C— group and/or —N—N— group and/or —CONH— group. Further, the group may have a double bond bonding to the ring A. The alkylene group may have 1 or more electron-withdrawing groups, electron-donating groups or hydrogen atoms as a substituent.

G represents an aromatic group which may have an electron-withdrawing group, an electron-donating group or a hydrogen atom. The ring A may have 1 or more electron-withdrawing groups and/or electron-donating groups as a substituent other than an —XG group.

Among them, it is preferable that the ring A is a 5- or 6-member ring containing at least 1 hetero atom, which is selected from the group consisting of a nitrogen atom, an oxygen atom and a sulfur atom, in the ring.

It is also preferable that the ring A is a 5- or 6-member ring containing 1 nitrogen atom in the ring. In this case, the 5-member ring is preferably an unsaturated ring and the 6-member ring is preferably a saturated ring.

Further, it is preferable that the alkylene group represented by X has 1 or more groups and/or atoms selected from the group consisting of an alkyl group, an acyl group, an alkoxy group, a nitro group, a hydroxycarbonyl group, an alkoxycarbonyl group, an aminocarbonyl group, a nitrile group and a halogen atom as a substituent.

For instance, the example of the formula (1) includes a tetrahydroisoquinoline derivative represented by the formula (2) and an indole derivative represented by the formula (3).

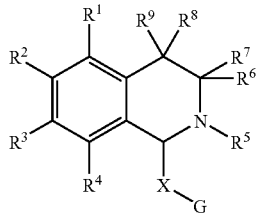

(2)

wherein $R^1$, $R^2$, $R^3$, $R^4$, X and G are the same defined above; $R^5$, $R^6$, $R^7$, $R^8$ and $R^9$ may be the same or different, each representing an electron-withdrawing group, an electron-donating group or a hydrogen atom.

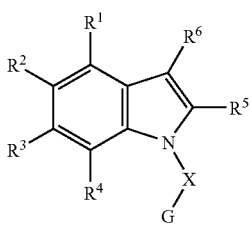

(3)

wherein $R^1$, $R^2$, $R^3$, $R^4$, X and G are the same as defined above; $R^5$ and $R^6$ may be the same or different, each representing an electron-withdrawing group, an electron-donating group or a hydrogen atom.

Specific examples of the tetrahydroisoquinoline derivative represented by the formula (2) include a compound having the structures shown by the formula (4) or the formula (5) and a salt thereof.

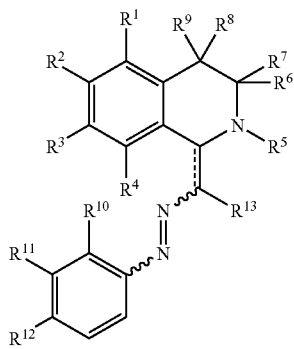

(4)

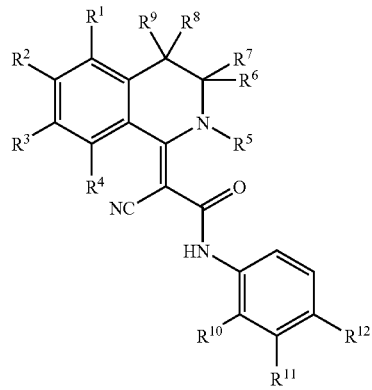

(5)

wherein $R^1$ to $R^{13}$ may be the same or different, each representing an electron-withdrawing group, an electron-donating group or a hydrogen atom.

More preferably, $R^1$ to $R^{13}$ include the group or atom selected from the group consisting of an alkyl group, an acyl group, an alkoxy group, a nitro group, a hydroxycarbonyl group, a nitrile group, an alkoxycarbonyl group, an aminocarbonyl group, a halogen atom and a hydrogen atom.

In the case of the formula (4), it is more preferable that $R^1$ to $R^4$, $R^8$, $R^9$, and $R^{10}$ are hydrogen atoms, $R^5$ is a hydrogen atom, a lower acyl group or a lower alkyl group, $R^6$ and $R^7$ are lower alkyl groups which may be the same or different, $R^{11}$ is a hydrogen atom, a halogen atom, a nitro group or a lower alkoxy group, $R^{12}$ is a hydrogen atom, a lower alkyl group, a lower acyl group or a lower alkoxy group, $R^{13}$ is a hydroxycarbonyl group, a nitrile group, an aminocarbonyl group or a lower alkoxycarbonyl group.

The lower alkyl group represented by R includes, for instance, methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl and the like. Preferred is methyl.

The lower alkoxy group represented by R includes, for example, methoxy, ethoxy, propoxy, isopropoxy, butoxy, sec-butoxy, tert-butoxy, pentoxy, hexyloxy, heptyloxy, octyloxy and the like. Preferred is methoxy.

The halogen atom represented by R includes fluorine, chlorine, bromine, and iodine. Preferred is chlorine or bromine.

The lower acyl group represented by R includes formyl, acetyl, propionyl, butyryl and the like. Preferred is acetyl.

The lower alkyl group which may form a ring structure, represented by R includes cyclobutyl, cyclopentyl, cyclohexyl, cycloheptyl, cyclooctyl and the like. Preferred is cyclopentyl, cyclohexyl or cycloheptyl.

The lower alkoxycarbonyl group represented by R includes methoxycarbonyl, ethoxycarbonyl, propoxycarbonyl and the like. Preferred is methoxycarbonyl or ethoxycarbonyl.

The aminocarbonyl represented by R includes, for example, —$CONR_2$ (each of Rs, which may be the same or different, represents a hydrogen atom, an above-exemplified lower alkyl group, or a phenyl group which may have a substituent) and the like.

The secondary aminocarbonyl group represented by R includes, for example, —CONHR (R represents the above-exemplified lower alkyl group, or the phenyl group which may have a substituent) and the like. The tertiary aminocarbonyl group includes, for example, —$CONR_2$ (each of Rs, which may be the same or different, represents the above-exemplified lower alkyl group, or a phenyl group which may have a substituent) and the like.

An aminoalkyl group represented by R includes, for example, —(CH$_2$)$_n$—NR$_2$ (n represents 1 to 8, preferably 1). Each of Rs, which may be the same or different, includes a hydrogen atom, a lower alkyl group, a lower alkyl groups which may form a cyclic structure (the cyclic structure may contain 1 to 3 hetero atoms such as a nitrogen and an oxygen) and a phenyl group which may have a substituent.

An acetoxyalkyl represented by R includes —(CH$_2$)$_n$—OAc (n represents 1 to 8), preferably n is 1.

The one-side broken double line in the formula (4) represents a single bond or a double bond. When the one-side broken double line in the compound represented by the formula (4) represents a double bond, the wavy lined portions (2 sites) represent the presence of the geometric isomer. Arrangement of these geometric isomers is not specially restricted, but may be any of the E isomer or the Z isomer each independently. The compound according to the present invention may be an arbitrary mixture of geometric isomers having pure shapes based on these geometric isomeric patterns.

In the formula (5), it is more preferable that R$^1$ to R$^4$, R$^8$ and R$^9$ are hydrogen atoms, R$^{10}$ is a hydrogen atom or a lower alkyl group, R$^5$ is a hydrogen atom, a lower acyl group or a lower alkyl group, R$^6$ and R$^7$ are lower alkyl groups, which may be the same or different, R$^{11}$ is a hydrogen atom, a halogen atom, a nitro group, a lower alkoxy group or a lower alkoxycarbonyl group, R$^{12}$ is a hydrogen atom, a lower alkyl group, a lower acyl group or a lower alkoxy group.

Specific examples of the formula (4) includes a compound in the formula (4) wherein the one-side broken double line is a double bond and R$^{13}$ is an aminocarbonyl group, and which is represented by the formula (7).

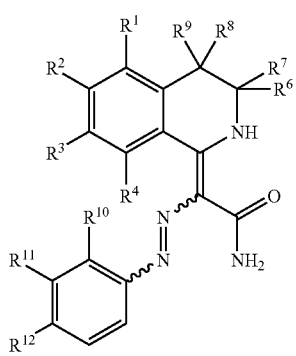

(7)

More specific compounds, which are the tetrahydroisoquinoline derivatives and represented by the before-described formula (4), include the following compounds:
2-(4-acetyl-phenylazo)-2-(3,3-dimethyl-3,4-dihydro-2H-isoquinoline-1-ylidene)-acetamide
2-(3-acetyl-phenylazo)-2-(3,3-dimethyl-3,4-dihydro-2H-isoquinoline-1-ylidene)-acetamide
2-(4-bromo-phenylazo)-2-(3,3-dimethyl-3,4-dihydro-2H-isoquinoline-1-ylidene)-acetamide
2-(3-bromo-phenylazo)-2-(3,3-dimethyl-3,4-dihydro-2H-isoquinoline-1-ylidene)-acetamide
2-(4-chloro-phenylazo)-2-(3,3-dimethyl-3,4-dihydro-2H-isoquinoline-1-ylidene)-acetamide
2-(3-chloro-phenylazo)-2-(3,3-dimethyl-3,4-dihydro-2H-isoquinoline-1-ylidene)-acetamide
2-(3,3-dimethyl-3,4-dihydro-2H-isoquinoline-1-ylidene)-2-m-tolylazo-acetamide
2-(3,3-dimethyl-3,4-dihydro-2H-isoquinoline-1-ylidene)-2-p-tolylazo-acetamide
2-(3,3-dimethyl-3,4-dihydro-2H-isoquinoline-1-ylidene)-2-(4-methoxyphenylazo)-acetamide
2-(3,3-dimethyl-3,4-dihydro-2H-isoquinoline-1-ylidene)-2-(3-methoxyphenylazo)-acetamide
2-(3,3-dimethyl-3,4-dihydro-2H-isoquinoline-1-ylidene)-2-(4-nitro-phenylazo)-acetamide
2-(3,3-dimethyl-3,4-dihydro-2H-isoquinoline-1-ylidene)-2-(3-nitro-phenylazo)-acetamide
2-(3,3-dimethyl-3,4-dihydro-2H-isoquinoline-1-ylidene)-2-(4-sulphamoyl-phenylazo)-acetamide
2-(3,3-dimethyl-3,4-dihydro-2H-isoquinoline-1-ylidene)-2-(3-sulphamoyl-phenylazo)-acetamide
2-(4-acetylamino-phenylazo)-2-(3,3-dimethyl-3,4-dihydro-2H-isoquinoline-1-ylidene)-acetamide
2-(3-acetylamino-phenylazo)-2-(3,3-dimethyl-3,4-dihydro-2H-isoquinoline-1-ylidene)-acetamide
2-(2-acetyl-phenylazo)-2-(3,3-dimethyl-3,4-dihydro-2H-isoquinoline-1-ylidene)-acetamide
2-(3,3-dimethyl-3,4-dihydro-2H-isoquinoline-1-ylidene)-2-phenylazo-acetamide (4-acetyl-phenylazo)-(3,3-dimethyl-3,4-dihydro-2H-isoquinoline-1-ylidene)-acetic acid ethyl ester
2-(4-acetyl-phenylazo)-2-(3,3-dimethyl-1,2,3,4-tetrahydroisoquinoline-1-yl)-acetamide
2-(4-acetyl-phenylazo)-2-(3,3-dimethyl-3,4-dihydro-2H-isoquinoline-1-ylidene)-N-methyl-acetamide
2-(4-acetyl-phenylazo)-2-(3,3-dimethyl-3,4-dihydro-2H-isoquinoline-1-ylidene)-N-phenyl-acetamide
2-(4-acetyl-phenylazo)-2-(2,3,3-trimethyl-3,4-dihydro-2H-isoquinoline-1-ylidene)-acetamide
(4-acetyl-phenylazo)-(3,3-dimethyl-3,4-dihydro-2H-isoquinoline-1-ylidene)-acetonitrile 2-(4-acetyl-phenylazo)-2-(3,3-dimethyl-3,4-dihydro-2H-isoquinoline-1-ylidene)-N,N-dimethyl-acetamide
(4-acetyl-phenylazo)-(3,3-dimethyl-3,4-dihydro-2H-isoquinoline-1-ylidene)-acetic acid 2-(2-acetyl-3,3-dimethyl-3,4-dihydro-2H-isoquinoline-1-ylidene)-2-(4-acetyl-phenylazo)-acetamide Specific examples of the formula (5) include the compounds represented by the following formula (8):

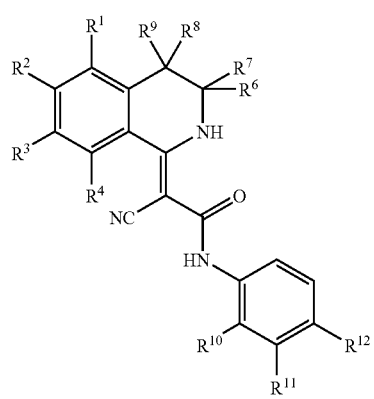

(8)

wherein R$^1$ to R$^4$ and R$^6$ to R$^{12}$ include groups or atoms selected from the same or different electron-withdrawing groups, or electron-donating groups or hydrogen atoms. Preferably, R$^1$ to R$^4$ and R$^6$ to R$^{12}$ include the group selected from the group consisting of an alkyl group, an alkenyl, an alkynyl, a phenyl group, a naphthyl group, a furyl group, a thienyl group, an alkoxy group, an alkylamino group, an alkylcarbonyl group, a benzoyl group, a naphthoyl group, a furoyl group, a tenoyl group, a dialkylcarbamoyl group, an acetyl group, a butanoyl group, a methoxycarbonyl group, a cycloalkyl group, a benzyloxy group, an adamantyloxy group and a nitro group, or a halogen atom or a hydrogen atom, which are all same or different each other. In addition, $R^1$ to $R^4$ and $R^6$ to $R^{12}$ are preferably groups or atoms selected from the group consisting of an alkyl group, an acetyl group, an alkoxy group, a nitro group, a halogen atom and a hydrogen atom.

The compounds represented by the formula (5) are exemplified as follows:

2-cyano-2-(3,3-dimethyl-3,4-dihydro-2H-isoquinoline-1-ylidene)-N-p-tolyl-acetamide 2-cyano-2-(3,3-dimethyl-3,4-dihydro-2H-isoquinoline-1-ylidene)-N-m-tolyl-acetamide 2-cyano-2-(3,3-dimethyl-3,4-dihydro-2H-isoquinoline-1-ylidene)-N-o-tolyl-acetamide 2-cyano-2-(3,3-dimethyl-3,4-dihydro-2H-isoquinoline-1-ylidene)-N-(4-methoxy-phenyl)-acetamide 2-cyano-2-(3,3-dimethyl-3,4-dihydro-2H-isoquinoline-1-ylidene)-N-(3-methoxy-phenyl)-acetamide 2-cyano-2-(3,3-dimethyl-3,4-dihydro-2H-isoquinoline-1-ylidene)-N-(4-nitro-phenyl)-acetamide 2-cyano-2-(3,3-dimethyl-3,4-dihydro-2H-isoquinoline-1-ylidene)-N-(3-nitro-phenyl)-acetamide 4-[2-cyano-2-(3,3-dimethyl-3,4-dihydro-2H-isoquinoline-1-ylidene)-acetylamino]-benzoic acid ethyl ester 3-[2-cyano-2-(3,3-dimethyl-3,4-dihydro-2H-isoquinoline-1-ylidene)-acetylamino]-benzoic acid ethyl ester 2-cyano-2-(3,3-dimethyl-3,4-dihydro-2H-isoquinoline-1-ylidene)-N-phenyl-acetamide 2-cyano-2-(3,3-dimethyl-3,4-dihydro-2H-isoquinoline-1-ylidene)-N-(2,4-dimethyl-phenyl)-acetamide 2-cyano-2-(3,3-dimethyl-3,4-dihydro-2H-isoquinoline-1-ylidene)-acetamide Salts of the compounds represented by the formula (2) or (3) are preferably a pharmaceutically acceptable salt. For example, a hydrochloride salt, a sulfate salt, a phosphate salt, a hydrobromate salt, a acetate salt, a maleate salt, a fumarate salt, a succinate salt, a methane sulfonate salt, a p-toluene sulfonate salt, a citrate salt and a tartarate salt may be formed.

In addition, ester compounds of the compounds represented by the formula (4) or (5) are within the scope of the present invention and, for example, include a carboxylic acid ester, a sulfonic acid ester and an inorganic acid ester.

The indole derivatives represented by the formula (3) include the compounds represented by the following formula (6):

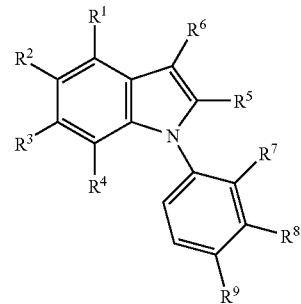

(6)

wherein $R^1$ to $R^9$ are same or different electron-withdrawing groups, electron-donating groups or hydrogen atoms. Among these, preferably, $R^1$ to $R^9$ include the group or atom selected from the group consisting of an alkyl group, an alkoxy group, a hydroxyl group, a nitro group, an acetoxy group, an aminoalkyl group, an acetoxyalkyl group, an aminovinyl group and a hydrogen atom. In addition, it is preferable that $R^1$ and $R^2$ are hydrogen atoms, $R^3$ is an acetoxy group or a hydroxyl group, $R^4$ is a hydrogen atom, a dialkylaminoalkyl group, a cyclic alkylaminoalkyl group, a hydroxyalkylaminoalkyl group or an acetoxy alkyl group, $R^5$ is a lower alkyl group or an arylaminovinyl group, $R^6$ is a nitro group, and $R^7$ to $R^9$ may be the same or different, each representing a lower alkyl group, a lower alkoxy group or a hydrogen atom.

The compounds represented by the formula (6) are exemplified as follows:
2-methyl-3-nitro-1-phenyl-1H-indole-6-ol
1-(4-methoxy-phenyl)-2-methyl-3-nitro-1H-indole-6-ol
2-methyl-3-nitro-1-p-tolyl-1H-indole-6-ol
2-[2-(4-methoxy-phenylamino)-vinyl]-3-nitro-1-p-tolyl-1H-indole-6-ol
1-(2-methoxy-phenyl)-2-methyl-3-nitro-1H-indole-6-ol
7-dimethylaminomethyl-2-(2-dimethylamino-vinyl)-3-nitro-1-p-tolyl-1H-indole-6-ol
1-(4-methoxy-phenyl)-2-methyl-3-nitro-7-piperidine-1-yl-methyl-1H-indole-6-ol hydrochloride
2-(2-dimethylamino-vinyl)-1-(4-methoxy-phenyl)-7-morpholine-4-ylmethyl-3-nitro-1H-indole-6-ol
7-[(3-hydroxy-propylamino)-methyl]-1-(4-methoxy-phenyl)-2-methyl-3-nitro-1H-indole-6-ol hydrochloride
7-dimethylaminomethyl-2-(2-dimethylamino-vinyl)-1-(4-methoxy-phenyl)-3-nitro-1H-indole-6-ol
7-diethylaminomethyl-1-(4-methoxy-phenyl)-2-methyl-3-nitro-1H-indole-6-ol
7-dimethylaminomethyl-2-methyl-3-nitro-1-p-tolyl-1H-indole-6-ol
1-(4-methoxy-phenyl)-2-methyl-3-nitro-7-piperidine-1-yl-methyl-1-indole-6-ol
Acetic acid 7-acetoxymethyl-2-methyl-3-nitro-1-p-tolyl-1H-indole-6-yl ester
2-(2-dimethylamino-vinyl)-1-(4-methoxy-phenyl)-3-nitro-7-piperidine-1-ylmethyl-1H-indole-6-ol
7-dimethylaminomethyl-2-methyl-3-nitro-1-phenyl-1H-indole-6-ol
7-dimethylaminomethyl-1-(4-methoxy-phenyl)-2-methyl-3-nitro-1H-indole-6-ol The compound according to the present invention can be prepared by conducting the methods described below and methods similar to them, or a publicly known method. The method for preparing the compound represented by the formula (9) is presented below:

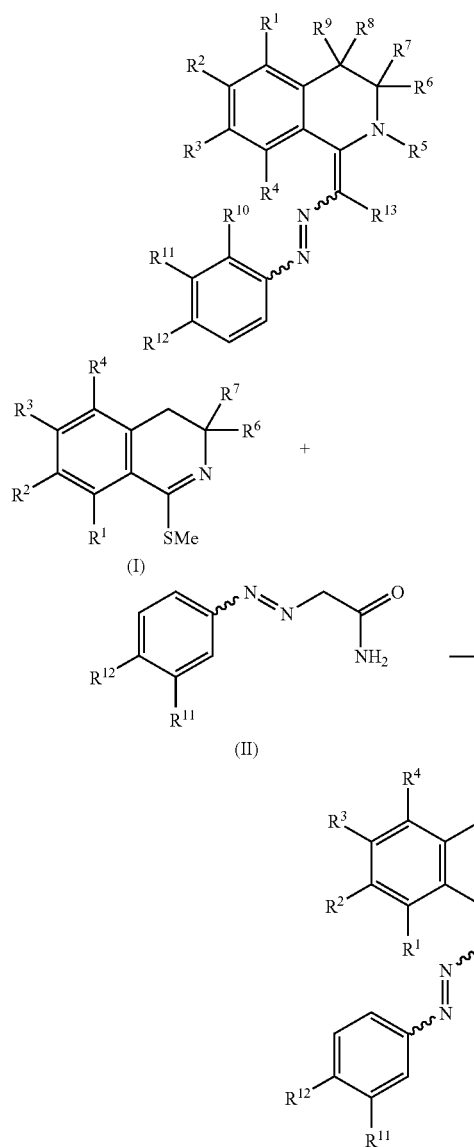

(9)

(I)

(II)

Preparation can be carried out by dissolving equal amounts of a thioether derivative (I) and a phenylazo acetamide derivative (II) in a proper solvent (for example, amide such as dimethyl formamide or dimethyl acetamide, ether such as tetrahydrofuran, or aromatic hydrocarbon such as benzene or toluene) not influencing badly on a reaction and refluxing up to the material is exhausted. The derivative (I) can be prepared by a publicly known method (for example, refer to Khim. Geterotsikl. Soedin., No. 7, p995 (1990) or purchased as a marketed product. Specifically, refer to the following Table 1:

TABLE 1

| Supplier | R1 | R2 | R3 | R4 | R6 | R7 |
|---|---|---|---|---|---|---|
| Asinex | —H | —OMe | —OMe | —H | -Me | -Me |
| Asinex | —H | —H | —H | —H | -cyclohexyl | |
| Asinex | —H | —H | —H | —H | -cyclopentyl | |
| Asinex | —OMe | —H | —H | —OMe | -Me | -Me |
| Asinex | —H | —OMe | —OMe | —H | - cyclopentyl | |
| Asinex | —H | —H | —H | —H | - cycloheptyl | |

TABLE 1-continued

| Supplier | R1 | R2 | R3 | R4 | R6 | R7 |
|---|---|---|---|---|---|---|
| PHARMEKS | —H | —H | —H | —H | -Me | -Me |
| LABOTEST | —H | —H | —H | —H | -Me | -Et |
| LABOTEST | —H | —H | —H | —H | -Et | -Et |
| MCL | —H | -Me | -Me | —H | -Me | -Me |
| MCL | —H | —H | —H | -Me | -Me | -Me |
| MCL | —H | —OCH2Ph | —OMe | —H | -Me | -Me |
| CBI | —H | —OH | —OMe | —H | -Me | -Me |
| CBI | —H | —H | —Br | —OMe | -Me | -Me |

The phenylazo acetamide derivative (II) can be prepared by a publicly known technique (Materialy Ural'sk. Soveshch. po Spektroskopii, 4th, Sverdlovsk 1963, p205 (1965), Bulletin de l'Academie Polonaise des Sciences, Serie des Sciences Chimiques, 14(1), p29 (1966), Am. Chem. Soc., Div. Org. Coatings, Plastics Chem. Preprints, 23(2), p486 (1963), Zhurnal Obshchei Khimii, 35(3), p559 (1965), Zhurnal Obshchei Khimii, 32, p526 (1962), etc.).

The compound represented by the formula (9) can be also synthesized by the following scheme:

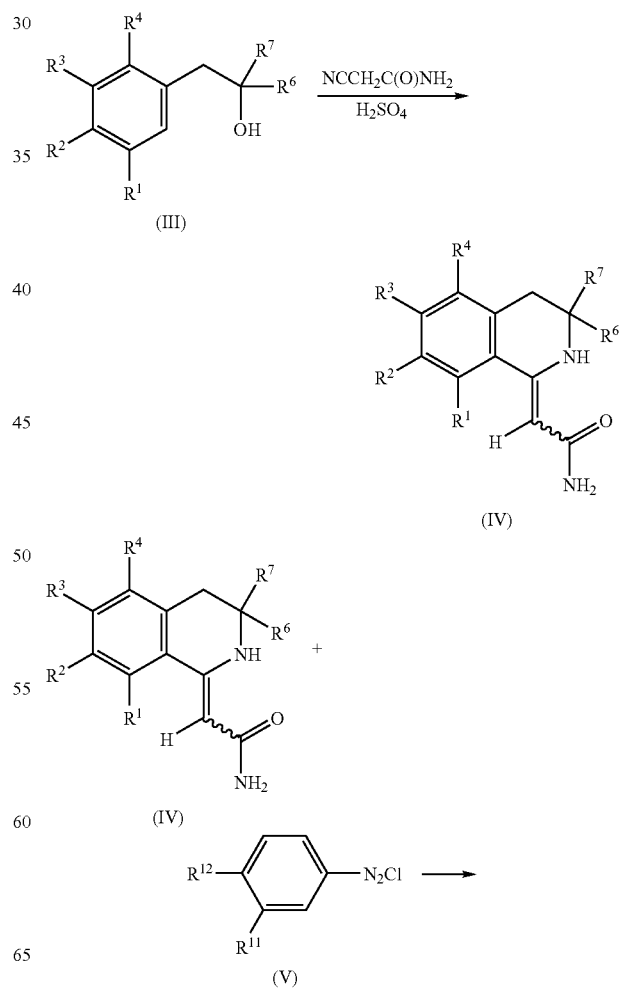

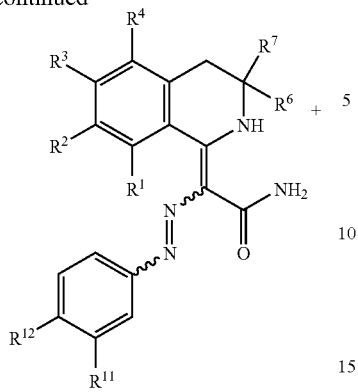

The compound can be obtained by reacting the compound (IV), which is obtained by reacting a benzyl carbinol derivative with a 2-cyanoacetamide derivative in the presence of sulfuric acid, with a diazonium salt (V) in an aqueous alcohol solution, which does not influence badly on the reaction, in the presence of hydrochloric acid. For the benzyl carbinol derivative, various derivatives can be purchased as the marketed product, and further can be prepared by a publicly known method (for example, J. Gen. Chem. USSR, No. 6, p1263 (1936)). The diazonium salt can be derived from a commercialized aminobenzene derivative by a publicly known method using hydrochloric acid and an aqueous solution of sodium nitrite.

Among the compounds represented by the formula (9),
2-(4-acetyl-phenylazo)-2-(3,3-dimethyl-3,4-dihydro-2H-isoquinoline-1-ylidene)-acetamide (Asinex, Russia),
2-(3-chloro-phenylazo)-2-(3,3-dimethyl-3,4-dihydro-2H-isoquinoline-1-ylidene)-acetamide (Asinex, Russia),
2-(3,3-dimethyl-3,4-dihydro-2H-isoquinoline-1-ylidene)-2-(3-methoxy-phenylazo)-acetamide (Asinex, Russia),
2-(3,3-dimethyl-3,4-dihydro-2H-isoquinoline-1-ylidene)-2-(3-nitro-phenylazo)-acetamide e (PHARMEKS, Russia),
2-(3,3-dimethyl-3,4-dihydro-2H-isoquinoline-1-ylidene)-2-(4-methoxy-phenylazo)-acetamide (PHARMEKS, Russia), and
2-(3,3-dimethyl-3,4-dihydro-2H-isoquinoline-1-ylidene)-2-m-tolylazo-acetamide (IBS, Russia);
are commercialized products and can be obtained from a supplier.

Among the compounds represented by the formula (9), the compound wherein $R^5$ is a methyl group, is prepared as follows. Preparation can be conducted by adding the compound ($R^5$=—H) which is represented by the formula (4) and sodium carbonate to a proper solvent (for example, nitrile such as acetonitrile, ether such as tetrahydrofuran, or aromatic hydrocarbon such as benzene or toluene), which does not influence badly on the reaction, to dissolve them; dropping slowly a mixture obtained by dissolving methyl iodide in a proper solvent (for example, amide such as dimethylformamide or dimethylacetamide, ether such as tetrahydrofuran, or aromatic hydrocarbon such as benzene or toluene), and refluxing the obtained mixture.

Among, the compounds represented by the formula (9), the compound wherein $R^5$ is an acetyl group, is prepared as follows. Preparation can be conducted by dissolving the compound ($R^5$=—H) represented by the formula (9) and dimethylaminopyridine in pyridine in an ice bath and adding acetic anhydride followed by stirring.

The compound represented by the formula (11) is prepared as follows:

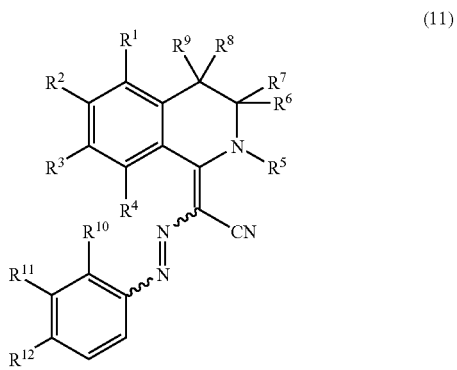

Preparation can be conducted by dissolving the compound represented by the formula (9) in a proper solvent (for example, amide such as dimethylformamide or dimethylacetamide), which does not influence badly on the reaction, and dropping a solution obtained by dissolving thionyl chloride in a proper solvent (for example, amide such as dimethylformamide or dimethylacetamide), which does not influence badly on the reaction, in an ice bath.

The compound represented by the formula (12) is prepared as follows:

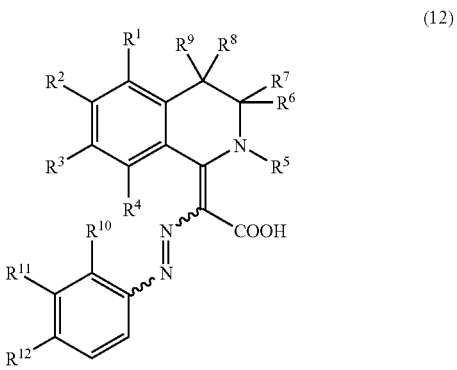

Preparation can be conducted by adding potassium hydroxide and the compound represented by the formula (9) to ethanol followed by reflux.

The compound represented by the formula (13) is prepared as follows:

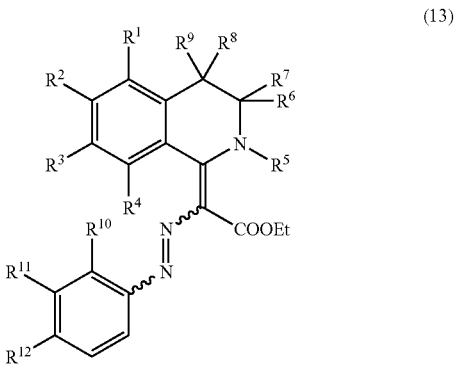

Preparation can be conducted by suspending the compound represented by the formula (12) in ethanol and dropping thionyl chloride slowly while cooling followed by string at room temperature.

The compound represented by the formula (14) is prepared as follows:

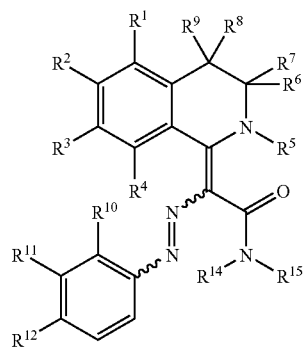

(14)

The compound represented by the formula (12), corresponding primary or secondary amine, HOBt (Advanced ChemTech Corp., USA) and triethylamine are dissolved in a proper solvent (for example, amide such as dimethylformamide or dimethylacetamide), which does not influence badly on the reaction. To this solution was added a solution prepared by dissolving HBTU (Advanced ChemTech Corp., USA) in a proper solvent (for example, amide such as dimethylformamide or dimethylacetamide, or halogen-based solvents such as dichloromethane), which does not influence badly on the reaction, followed by stirring at room temperature for the preparation.

The compound represented by the formula (10) is prepared as follows:

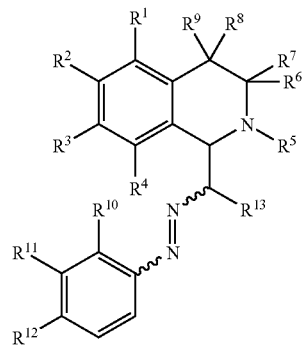

(10)

Preparation can be conducted by dissolving the compounds represented by the formula (9) and (11) to (14) in a proper solvent (for example, nitrile such as acetonitrile), which does not influence badly on the reaction, and adding the solution prepared by dissolving a triphenyltin hydride (Aldrich, USA) in a proper solvent (for example, aromatic hydrocarbon such as benzene, toluene or xylene), which does not influence badly on the reaction, to the above solvent, followed by reflux.

The compound represented by the formula (4) can be dissolved in a proper solvent, and may exist as it is or as a reduced type represented by the following formula (15) or their mixture in the solvent:

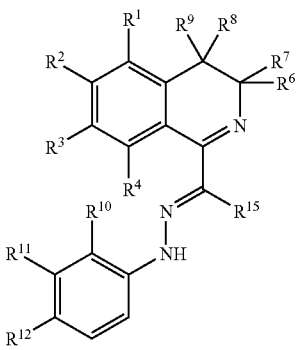

(15)

The compounds according to the present invention or salts thereof, which are obtained in such the way, can be isolated and purified by an ordinary separation means such as recrystallization, distillation or chromatography. When obtained in a free form in such the way, the compound according to the present invention can be converted to a salt thereof by a publicly known method or similar methods. In contrast, obtained in a salt form, the compound can be converted to a free form or other salts by a publicly known method or similar methods. The compound or the salt thereof may have an asymmetric carbon. When the compound is obtained as an optically active mixture (racemic compound), it can be separated into each optical activity by an ordinary optical dividing means.

A usable concentration of the differentiation inhibiting agent according to the present invention is preferably ranges from 0.1 ng/mL to 1 mg/mL, more preferably from 10 ng/mL to 100 μg/mL, particularly preferably from 100 ng/mL to 10 μg/mL.

The differentiation inhibiting agent according to the present invention comprises a low molecular weight compound, particularly a tetrahydroisoquinoline derivative, which keeps undifferentiation of the embryonic stem cell without activation of STAT3 (signal transducer and activator of transcription 3). Undifferentiation of the embryonic stem cell of a specific mouse line is maintained by LIF regardless of the presence or absence of the feeder cell composed of fibroblast cell derived from a mouse fetus. It has been known that the LIF transmits a signal to a downstream through activation of STAT3 (Matsuda et al., EMBO Journal, 18: 15: p4261, 1999). However, in recent years, the presence of a differentiation inhibiting factor keeping undifferentiation of the embryonic stem cell without activation of STAT3 was reported (Dani et al., Developmental Biology 203: p149, 1998), and thus, it is believed that a mechanism of keeping undifferentiation of the embryonic stem cell without activation of STAT3 is present. In addition, LIF shows no effect on keeping undifferentiation of the embryonic stem cell of primates (Thomson et al., Proc. Natl. Acad. Sci. USA 92: p7844, 1995, Thomson et al., Science 282: p1145, 1998, Reubinoff et al., Nature Biotech 18: p399, 2000) and, hence, it is suggested that, in the embryonic stem cell of primates, there is a mechanism of keeping undifferentiation state by a signal different from LIF and STAT3. The differentiation inhibiting agent according to the present invention comprises a low molecular weight compound which keeps undifferentiation of the embryonic stem cell without activation of STAT3. In other words, the differentiation inhibiting agent comprises a low molecular weight compound having the activity of keeping undifferentiation state of the embryonic stem cell by an action different from the action of the LIF.

Recently, as one of molecules regulating undifferentiation of the embryonic stem cell without activation of LIF and STAT3, the Nanog gene was identified (Mitsui et al., Cell 113: p631, 2003, Chambers et al., Cell 113: p643, 2003). The presence of the Nanog gene was found from a mouse and a human. When expression of the Nanog gene is suppressed by gene destruction, the totipotency of the embryonic stem cell is lost and, in contrast, when the Nanog gene is strongly expressed to increase an expression level, undifferentiation of the embryonic stem cell can be maintained even with the absence of LIF. Therefore, a substance, e.g., a low molecular weight compound, enabling increase in the expression level of the Nanog gene, can be used for maintaining undifferentiation of the embryonic stem cell, namely, for culturing the totipotent embryonic stem cell.

On the other hand, the high expression of the Nanog gene does not activate STAT3 and, therefore, the Nanog gene keeps undifferentiation of the embryonic stem cell independently on LIF and STAT3. That is, it is suggested that a substance, e.g., a low molecular weight compound, enabling increase in the expression level of the Nanog gene, can be used for culturing the embryonic stem cell in which the effect of maintaining undifferentiation by LIF is not observed.

The differentiation inhibiting agent according to the present invention comprises a low molecular weight compound which increases the expression level of the Nanog gene. In other words, the differentiation inhibiting agent according to the present invention comprises a low molecular weight compound exerting the ability of keeping undifferentiation of the embryonic stem cell through the increase in the expression level of the Nanog gene.

On the other hand, according to a recent report, also in a certain mesenchymal stem cell derived from a marrow, it was observed similarly to the embryonic stem cell that culture of the stem cell derived from the mouse depends on the LIF and culture of the stem cell derived from the human does not depends on the LIF (Verfaillie al., Nature 418: p41, 2002). This suggests that the stem cell showing multipotency has the mechanism of keeping undifferentiation state similarly to the embryonic stem cell. Therefore, similarly to the embryonic stem cell, it is suggested that the undifferentiation of the stem cell of primates is probably maintained by a signal different from that of a LIF-STAT3 route. The differentiation inhibiting agent according to the present invention comprises a low molecular weight compound having the activity of keeping a cell in undifferentiation state without the STAT3 route.

The differentiation inhibiting agent according to the present invention can be used by adding to an any basic culture medium for mammal cell culture, which is a basic medium for animal cell culture Examples of the basic media for animal cell culture include Dulbecco's modified Eagle medium (DMEM), knockout DMEM, Glasgow MEM (GMEM), RPMI1640 and IMDM (these are Invitrogen Corp., USA made), but are not restricted to these examples. One embodiment of the cell culture medium is Dulbecco's modified Eagle medium (DMEM). In addition, these basic media can be used by adding with proteins involving in cell proliferation and differentiation regulation such as serum or a serum alternate, various kinds of growth factors and cytokines. Further, any compound may be added. Serum may be any serum or serum-based solution to supply a nutrient effective for proliferation and maintaining survival of the stem cell and the embryonic stem cell. Examples of such serum include fetal calf serum (FCS), calf serum (CS), and horse serum (HS). The usable serum replacements include those known to those skilled in the art, proteins, amino acids, lipids, vitamins, and the like independently or in combination of them. Proteins include insulin, transferrin, albumin, peptone, FGF (Fibroblast Growth Factor), EGF (Epithelial Growth Factor) and the like, amino acids include arginine, cysteine, glutamine, glycine, histidine, isoleucine, leucine, lysine, methionine, phenylalanine, serine, threonine, tryptophane, tyrosine, valine and the like, and vitamins include pantothenic acid, choline, folic acid, inositol, nicotinic acid amide, riboflavin, thiamine, pyridoxine and the like, however, restriction is not applied to these compounds. In one embodiment, serum is bovine fetus serum. In more specific embodiment, bovine fetus serum is provided with a concentration between about 25% and about 1%. In more specific embodiment, the concentration of bovine fetus serum in the cell culture medium is 15%. In another embodiment, the serum replacement is knockout serum replacement: KSR (Invitrogen Corp. USA made). The cell growth factors which can be added include a hepatocyte growth factor (HGF), epidermal growth factor (EGF), fibroblast growth factor (FGF), insulin-like growth factor (IGF), nerve growth factor (NGF), platelet-derived growth factor (PDGF), vascular endothelial growth factor (VEGF), transforming growth factor (TGF), bone morphogenetic protein (BMP), stem cell factor (SCF), Wnt, and the like, however, restriction is not applied to these compounds. The cytokines which can be added include interleukin (IL), granulocyte-macrophage colony stimulating factor (GM-CSF), and the like, however, restriction is not applied to these compounds. Further, differentiation regulation factor such as LIF and notch ligand can be added. The compound to be added is not specially restricted and may be an agonist or an antagonist to any protein and, also, may be an any phosphorylation inhibitor. In one embodiment, PD98059 (Cell Signaling Technology Corp. made) is provided. In another embodiment, 6-bromoindirubin-3oxim is provided.

Cell culture medium also contains an antioxidant (a reductant) (for instance, β-mercaptoethanol). In a preferable embodiment, β-mercaptoethanol has a concentration of about 0.1 mM. Other antioxidants (for instance, monothioglycerol or dithiothreitol (DTT) independently or in combination) can be used to provide a same effect. Further, other equivalent substances are known to those skilled in the art of cell culture.

The differentiation inhibiting agent according to the present invention and the active ingredient thereof can be used by accompanying any culture medium material or by immobilizing it to the culture medium material. For the culture medium material, a porous material can be used. The porous material is the material having many fine pores and is not specially restricted in a kind, thickness, shape, and size of the material. The kind of the material may be an organic material, an inorganic material, and a complex material composed of an organic material and an inorganic material. The shape of the porous material may be any forms including flat plate, globular, rod-like, fibrous and hollow, and, for example, includes a film, sheet, membrane, board, unwoven fabric, filter paper, sponge, cloth, knitted fabric, lump, thread, hollow tube and particle. For culturing cells, the unwoven fabric is more preferable in consideration of an easily regulatable pore size to support cells for allowing 3-dimensional culture and easy and low cost preparation of the material. The pore size of the porous material is not specially restricted, however, in consideration of 3-dimensional support of cells, an average pore size is preferably between 0.1 μm and 100 μm and further preferably between 1 μm and 50 μm. A fiber diameter is not specially restricted, however, 0.03 denier or smaller is preferable.

In order to increase adhering performance, undifferentiation-maintaining ability, and proliferation ability of cells, the porous material as described above may be subjected to surface coating treatment with a high polymer. The high polymer is the substance that is constructed by linking linearly, squarely, or cubically 1 or more species of monomers being repeating constitutional units and that has a some-hundred molecular weight. The high polymer is classified into 3 major categories: natural high polymer, semisynthesized high polymer, and synthesized high polymer. For the present invention, any high polymers can be used.

For example, the natural high polymer includes mica, asbestos, graphite, diamond, starch, cellulose, saccharides such as alginic acid, and proteins such as gelatin, fibronectin, fibrinogen, laminin, and collagen. The semisynthesized high polymer includes glass, cellulose nitrate, cellulose acetate, rubber hydrochloride, and carboxymethyl cellulose. The synthesized high polymer includes polyphosphonitrile chloride, polyethylene, polyvinyl chloride, polyamide, polyethylene terephthalate, polysulfon, polyacrylonitrile, polyvinyl alcohol, polymethyl methacrylate, polyhydroxyethyl methacrylate, polydimethylaminoethyl methacrylate, and a copolymer, which is composed of 2 or more types of synthesized monomers, represented by the copolymer prepared by hydroxyethyl methacrylate and dimethylaminoethyl methacrylate.

In consideration of easy coating processing, organic high polymers are preferable, and proteins, peptides and synthesized organic high polymers are more preferable. In one embodiment, the culture medium material is gelatin. In another embodiment, Matrigel (BD Bioscience Corp. made.) is used.

A method and an apparatus for separation of the stem cell or the embryonic stem cell from a population of a plurality of different cells to carry out culturing can be provided by using the culture medium material, to which the differentiation inhibiting agent according to the present invention has been immobilized, as a cell-capturing material. Namely, a culture method of the stem cell or the embryonic stem cell is provided, wherein the stem cell or the embryonic stem cell and a cell-containing liquid containing cells, which should be removed, are introduced into a container in which the cell-capturing material of the culture medium material such as the porous material (on which the differentiation inhibiting agent according to the present invention has been immobilized) is filled, the stem cell or the embryonic stem cell is captured by the cell-capturing material, and, after the cells, which should be removed, are lead out from the container, the whole of the cell-containing solution with the container is cultured; and a cell-culturing apparatus, wherein the cell-capturing material of the culture medium material, on which the differentiation inhibiting agent according to the present invention is immobilized, is filled in the container, is provided, the cell-culturing apparatus being characterized in that the cell-capturing material as described above can be used as a support for cell culture and the container can be used for cell culture. The cells, which should be removed, are all cells other than the stem cells or the embryonic stem cells. In addition, cells which were differentiated from the stem cells or the embryonic stem cells and lost multipotentcy, are also included in this cell group. The cell-containing liquid to be introduced into the cell-capturing material is satisfied by any cell liquid containing the stem cells or the embryonic stem cells and, as the example, includes blood, marrow, fragment tissue liquid, or a culture solution of the stem cells or the embryonic stem cells.

The present invention relates to a method for proliferating the stem cells or the embryonic stem cells. A cultured product of the stem cells or the embryonic stem cells proliferated by using the differentiation inhibiting agent according to the present invention can be provided.

Cells cultured by using the differentiation inhibiting agent according to the present invention includes all the stem cells or the embryonic stem cells which can be obtained by using the publicly known method and material. The stem cell includes, as an example, the stem cell available by the following publicly known method. A marrow cell ("Marrow Transplantation Guide" by H. J. Deeg, H. G. Klingemann, G. L. Phillips, translated in Japanese by Sinpei Kasakura), a marrow stem cell (Osawa et al., Science 273: p242-245, 1996, Goodell et al., J. E. Med. 183: p1797-1806, 1996, Verfaillie et al., Nature 418: p41, 2002), a neural stem cell (Reynolds et al., Science, p1707-1710, 1992), a tissue stem cell (Goodell et al., J. E. Med. 183: p1797-1806, 1996, Matsuzaki et al., Experimental Medicine 19: p345-349, 2001, Blau et al., Cell, 105: p829-841, 2001), a mesenchymal stem cell (Liechty et al., Nature Medicine, 6: p1282-1286, 2000, Pittenger et al., Science 284: p143-147, 1999) and a skin stem cell and epidermal stem cell (Murota Seiitsu (ed.), "Regeneration Medicine and Regeneration Therapy," Gendai Kagaku Extra Number 41, Tokyo Kagaku Douzin).

The embryonic stem cells to be cultured can be obtained by using the following publicly known method and material. Murine embryonic stem cell: Evans et al., Nature 292: p154, 1981, bovine ES cell: Schellander et al., Theriogenology 31: p15-17, 1989, swine ES cell: Strojek et al., Theriogenology 33: p901, 1990, sheep ES cell: Handyside, Roux's Arch. Dev. Biol. 196: p185, 1987, hamster ES cell: Doetschman et al., Dev. Biol. 127: p224, 1988, rhesus monkey ES cell: Thomson et al., Proc. Natl. Acad. Sci. USA 92: p7844, 1995, cynomolgus monkey ES cell: Suemori et al., Dev. Dyn. 222: p273, 2001, human ES cell: Thomson et al., Science 282: p1145, 1998, Reubinoff et al., Nature Biotech 18: p399, 2000, human EG cell: Gearhart et al., Proc. Natl. Acad. Sci. USA, 95: p13726, 1998. On the other hand, mouse embryonic stem cell (129SV and C57/BL6) can be obtained from Dai Nippon Seiyaku k. k.

The differentiation inhibiting agent provided according to the present invention can be used for all the stem cells and the embryonic stem cells, and is desirably used for the stem cells and the embryonic stem cells of mammals and more preferably used for the stem cells and the embryonic stem cells of primates.

Cells and embryonic stem cells, which have been once isolated, can be cultured in the undifferentiated state by using the differentiation inhibiting agent of the present invention.

The degree of the undifferentiated state of the stem cell, preferably the embryonic stem cell, cultured by using the differentiation inhibiting agent of the present invention can be confirmed by measuring an alkaline phosphatase (ALP) activity existing on a cell membrane of the stem cell. It is known that in an undifferentiated embryonic stem cell, the ALP activity is kept and, when the cell is differentiated, decreases (Williams et al., Nature 336: p684, 1988, Thomson et al., Science 282: p1145, 1998). The alkaline phosphatase (ALP) activity is detected by methods including a staining method by using an insoluble substrate or a spectrophotometric method by using a water-soluble substrate.

In one embodiment, the ALP activity can be quantified by the spectrophotometric method. An alkaline solution of paranitrophenylphosphate (pNPP) is added to a cell on a culture dish. pNPP is hydrolyzed by ALP present on the cell membrane to produce paranitrophenol. Measuring an absorbance of the produced solution at 405 nm enables quantification of alkaline phosphatase activity. Measuring the ALP activity of the embryonic stem cell cultured by adding the differentiation inhibiting agent of the present invention on the basis of the method described in Example 1 (5) shows that this cell has significantly higher ALP activity than that of a control embryonic stem cell cultured by using a culture medium lacking the differentiation inhibiting agent. This means that the differentiation inhibiting agent of the present invention allows the cells to proliferate while keeping the undifferentiated state of the embryonic stem cell.

In another embodiment, the ALP activity can also be detected by ALP staining method. A reaction solution containing a phosphate ester salt and a diazonium salt as the substrate are added to cells on a culture dish. The phosphate ester salt is hydrolyzed by alkaline phosphatase present on the cell membrane and, subsequently, a coupling reaction with the diazonium salt produces an azo pigment resulting in sedimentation of the pigment in an ALP active site. Counting number of stained colonies enables quantification of the ALP activity of the cell to allow quantifying the degree of undifferentiation of the cell. ALP staining of the embryonic stem cell cultured by using the differentiation inhibiting agent of the present invention on the basis of the method described in Example 1 (6) shows that this cell has significantly higher ALP activity than that of a control cell cultured by using a culture medium lacking the differentiation inhibiting agent. This means that the differentiation inhibiting agent of the present invention allows the cell to proliferate while keeping the undifferentiated state of the embryonic stem cell.

In addition, the degree of undifferentiation of the embryonic stem cell can be known by measuring the expression level of the Oct-3/4 gene. The Oct-3/4 gene is a transcription factor belonging to a POU family, and is expressed specifically in the undifferentiated state in the embryonic stem cell and an embryonic cancer cell (EC cell) (Okamoto et al., Cell 60: p461, 1990) and is expressed only in an undifferentiated cell line (Scholer, Trends Genet 7: p323, 1991). In addition, homozygous mice of which Oct-3/4 gene has been disrupted, stops development at the blastodermic vesicle stage. Hence, it was found that the Oct-3/4 gene has an important function for keeping the undifferentiated state (Nichols et al., Cell 95: p379, 1998). On the other hand, it was recently found that an over expression of the Oct-3/4 gene promotes differentiation of the embryonic stem cell (Niwa et al., Nat. Genet. 24: p372, 2000). Therefore, it is important to keep the expression level of the Oct-3/4 in a specific range to maintain the undifferentiated state. As an embodiment of measuring the expression level of the Oct-3/4 gene, a quantitative PCR (polymerase chain reaction) method can be used.

In one embodiment, a real time PCR method is used to enable a convenient and reliable quantitative measurement having a wide dynamic range. The real time PCR technique includes the method by using a TaqMan probe using ABI-PRISM7700™ (Applied Biosystems) and the method by using LightCycler™ (Ropehe Diagnostics). Particularly in the latter case, in a high rate reaction cycle in which a temperature cycle of PCR is completed for some 10 minutes, a change of an amplified amount of a DNA synthesized for every cycle can be detected in a real time. DNA detection method of the real time PCR method includes 4 methods using a DNA-binding pigment (intercalator), a hybridization probe (kissing probe), TaqMan probe, or Sunrise Uniprimer (molecular beacon). On the other hand, the expression level of the Oct-3/4 gene can be analyzed by using a DNA-binding pigment such as SYBR GreenI. SYBR GreenI is a binding pigment specific to a double strand of the DNA and, when bound to a double strand, an inherent fluorescence intensity is reinforced. By adding SYBR GreenI at the PCR reaction and measuring the fluorescence intensity at the end of each cycle of an elongation reaction, the increase in a PCR product can be detected. For detection of Oct-3/4 gene, similar to normal PCR, a primer is designed by using a commercialized gene analysis software on the basis of a sequence of the Oct-3/4 gene. SYBR GreenI detects a nonspecific product and, thus, requires designing an optimal primer. Required designing standards are a length of an oligomer, a base composition of the sequence, a GC content, and a Tm value.

Frequently, quantitative PCR aims to know the amount of a target DNA for a specific amount of a sample. For this purpose, an evaluation is required for the sample amount first added to a reaction system. In this case, measuring other DNA than the target DNA as an internal standard reflecting the sample amount enables to correct the sample amount first added to the reaction system. The internal standard used for correction of the sample amount can be a house keeping gene, ordinarily, of which expression level is believed to show no difference between tissues. For example, the internal standard includes genes of glyceraldehydes phosphate dehydrogenase (GAPDH) being a major enzyme in a glycolysis system, β-actin or γ-actin being a compositional component of a cell skeleton, and S26 being a compositional protein of a ribosome.

An expression level of the Oct-3/4 gene can be determined for the cell exposed to the differentiation inhibiting agent of the present invention. The compound, which has the activity capable of keeping significantly the expression level of Oct-3/4 gene as compared with the expression level of Oct-3/4 gene of a control cell which has not been exposed to the differentiation inhibiting agent of the present invention, that is, which has been differentiated and induced from the embryonic stem cell, is regarded as the differentiation inhibiting agent which maintains undifferentiation of the embryonic stem cell.

Still further another method for screening an optimized culture medium material for keeping undifferentiation of the embryonic stem cell includes a method for detecting such antigen as Stage Specific Embryonic Antigen (hereafter SSEA)-1, SSEA-3, and SSEA-4 which are expressed specifically in undifferentiated cells (Smith et al., Nature 336: p688, 1988, Solter et al., Proc. Natl. Acad. Sci. U.S.A 75: p5565, 1978, and Kannagi et al., EMBO J. 2: p2355, 1983).

In one embodiment, a surface antigen such as SSEA-1 can be labeled by incubating together with a specific antibody (primary antibody) recognizing the antigen and further incubating together with a second antibody (secondary antibody) bound to such reporter as a fluorescence labeling substance. This operation makes the cell expressing the target antigen fluorescent. Subsequently, the labeled cell can be counted and collected separately by employing such a standard method as flow cytometry. Following this step, numbers of labeled and nonlabeled cells can be compared to determine an effect of the target culture medium material. Alternatively, following exposure to a marker antibody of the nonlabeled cell surface, the cell can be exposed to the second antibody specific to an anti-cell surface antigen antibody (for example, anti-SSEA-1 antibody) in ELISA (enzyme-linked immunosorbent assay) manner, and number of cells expressing a desired surface antigen can be quantified by colorimetry or fluorescence measurement. Other methods for quantifying cells expressing surface antigen have been known by those skilled in the art concerning cell culture.

The improved differentiation inhibiting agent, culture method, and culture liquid for proliferation of the stem cells or the embryonic stem cells which are provided according to the present invention, are expected to be applied to all techniques for which the stem cells or the embryonic stem cells are useful.

Cells produced by using the differentiation inhibiting agent, culture method, and culture liquid according to the present invention can be used, after differentiation thereof, for cell transplantation and artificial tissue construction accompanying with the use of an artificial support tissue to use for in vivo transplantation and an artificial organ. Using for cell transplantation therapy and tissue engineering of the stem cell can solve some problems in transplantation therapy, which includes conventional autotransplantation, such as tissue deficit after a transplanting piece is resected from a donor and shortage of the donor. The cell and tissue cultured for transplantation are used for returning to the identical person from whom the cell and tissue were collected, and for transplanting into other person, for medical treatment, and the cell and tissue of the present invention can be used for both purposes.

The differentiation inhibiting agent of the present invention, the culture method using the inhibiting agent, and the culture product of a natural and a modified stem cell, preferably embryonic stem cell, obtained by using the culture liquid containing the inhibiting agent is used for monitoring the stem cell, preferably embryonic stem cell or for screening a substance which improving the collection of the stem cell. For example, the substance presumably inducing differentiation of the stem cell or the embryonic stem cell can be added to a cell culture product proliferated by using the method as described above. In comparison with a control cell culture product lacking the substance presumably inducing differentiation of the stem cell or the embryonic stem cell, a substance inducible of differentiation into a triploblastic lines is identified as an embryonic stem cell differentiation-inducing factor.

The differentiation inhibiting agent and/or compound of the present invention or the salt thereof has an excellent stem cell undifferentiation-maintaining and proliferating abilities and, hence, can be used as a remedy for the tissue and the organ damaged by a disease or an injury Targeted diseases include, for example, burn, intractable skin ulcer, bedsore, hyperplastic scar, birthmark, and tattoo and the like, which are related to a skin; fracture, osteoporosis and the like, which are related to a bone; osteoarthritis, chronic rheumatism, hernia of intervertebral disk, apophysitis, sport damage, which are related to a cartilage; Parkinson's disease, Huntington's disease, Alzheimer's disease, break of a nerve of limb caused by an injury, damage caused by head and neck surgery or thoracic surgery, facial nerve palsy, phrenic nerve damage, intrapelvic nerve damage and the like, which are related to a nerve; alveolar bone damage and anodontia caused by periodontal disease or pyorrhea and the like, which are related to a tooth; male pattern alopecia, which is related to a hair; birth defect, endothelial cell decompensation, opacity caused by cornea infection, cornea degeneration, cornea shape abnormality and the like, which are related to a cornea; hypertension, chronic arterial occlusion, ischemic heart disease and the like, which are related to a blood vessel; myocardial infarction, which is related to a cardiac muscle; diabetes and the like, which are related to a pancreas; hepatitis, hepatic cirrhosis, hepatic failure and the like, which are related to a liver; however, are not restricted to these examples.

The differentiation inhibiting agent and/or compound of the present invention can be administered orally or parenterally as preventive and/or remedy for diseases as described above; and is orally administered normally in a solid form such as tablet, capsule, granule and powder through blending with a pharmaceutically acceptable carrier, or is parenterally administered intravenously, subcutaneously or intramuscularly as an injection, suppository, or sublingual tablet. Further, sublingual, subcutaneous and intramuscular administration may be conducted as a sustained-release preparation such as a sublingual tablet and a microcapsule. A daily dose depends on a degree of a symptom; an age, sexuality, body weight, difference in sensitivity of an administrative subject; time and interval of administration, property, compounding and kind of a medicine preparation; a kind of the active ingredient, however, are not restricted especially. Normally, for a 1 kg mammal body weight about 0.01-100 mg, preferably about 0.02-20 mg, more preferably about 0.1-10 mg, or most preferably 0.5-10 mg is normally given in 1 to 4 times a day. The dose for using in animal husbandry and fisheries fields follows the above standard and, for a 1 kg body weight of a target organism, about 0.01-30 mg or preferably about 0.1-10 mg is normally given in 1 to 3 times a day. The content of the compound of the present invention contained in a pharmaceutical composition ranges from about 0.01-100% by weight of the whole composition.

As the above-described pharmaceutically acceptable carrier, various kinds of organic or inorganic carrier substances conventionally used as a drug preparation materials are used and compounded as a vehicle, lubricant, binder, disintegrator in a solid preparation; and a solvent, solubilizer, suspending agent, isotonizing agent, buffering agent, soothing agent and the like in a liquid preparation. Further, when required, such preparation additives as an antiseptic agent, antioxidant, colorant, edulcorant and the like can also be used. Preferable examples of the vehicle include, for example, lactose, saccharose, D-mannitol, starch, crystallized cellulose, light anhydrous silicic acid, and the like. Preferable examples of the lubricant include, for example, magnesium stearate, calcium stearate, talc, colloid silica, and the like. Preferable examples of binder include, for example, crystallized cellulose, saccharose, D-mannitol, dextrin, hydroxypropyl cellulose, hydroxypropylmethyl cellulose, polyvinyl pyrolidone, and the like.

Preferable examples of disintegrator include, for example, starch, carboxymethyl cellulose, calcium carboxymethyl cellulose, croscarmellose sodium, sodium carboxymethyl starch, and the like. Preferable examples of the solvent include, for example, water for injection, alcohol, propylene glycol, macrogol, sesame oil, corn oil, and the like. Preferable examples of solubilizer include, for example, polyethylene glycol, propylene glycol, D-mannitol, benzyl benzoate, ethanol, tris amino methane, cholesterol, triethanolamine, sodium carbonate, sodium citrate, and the like. Preferable examples of the suspending agent include, for example, surfactants such as stearyl triethanolamine, sodium lauryl sulfate, lauryl aminopropionic acid, lecithin, benzalkonium chloride, benzethonium chloride and glycerin monostearate, hydrophilic high polymer such as polyvinyl alcohol polyvinyl pyrrolidone, sodium carboxymethyl cellulose, methyl cellulose, hydroxymethyl cellulose, hydroxyethyl cellulose, hydroxypropyl cellulose, and the like.

Preferable examples of the isotonizing agent include, for example, sodium chloride, glycerin, D-mannitol and the like. Preferable examples of the buffering agent include, for example, a buffer liquid of phosphate, acetate, carbonate, citrate and the like. Preferable examples of the soothing agent include, for example, benzyl alcohol and the like. Preferable examples of the antiseptic agent include, for example, paraoxybenzoic acid esters, chlorobutanol benzyl alcohol, phenethyl alcohol, dehydroacetic acid, sorbic acid and the like. Preferable examples of the antioxidant include, for example, sulfite, ascorbic acid and the like.

The suspending agent, solubilizer, stabilizer, isotonizing agent, preservative or the like is added to the differentiation inhibiting agent and/or compound of the present invention, so as to prepare a venous, subcutaneous or intramuscular injection by a publicly known method. At this preparation, when required, a freeze-dried product can be prepared by a publicly known method. When administered to a human, for example, the compound of the present invention can be safely administered orally or parenterally in an independent form or in the form, which is blended with a proper pharmacologically acceptable carrier, vehicle or diluent, as a pharmaceutical composition. The pharmaceutical composition as described above includes an orally-administering agent (example: powder, granule, capsule, tablet), a parenterally-administering agent [example: an injection, a drip, an external using agent (example: a nasal preparation, a percutaneous preparation and the like), and a suppository (example: a rectum suppository, a vaginal suppository and the like)]. These preparations can be manufactured by a method known per se ordinarily commonly used for drug preparation steps.

The differentiation inhibiting agent and/or compound of the present invention can be made in an injection by forming as an aqueous injection by blending with a dispersant (example: Tween 80 (Atlas Powder Corp., USA made), HCO60 (Nikkou Chemicals made), polyethylene glycol, carboxymethyl cellulose, sodium alginate and the like), a preservative (example: methyl paraben, propyl paraben, benzyl alcohol and the like), an isotonizing agent (example: sodium chloride, mannitol, sorbitol, glucose and the like), or an oily injection prepared by dissolving, suspending, or emulsifying in a plant oil such as olive oil, sesame oil, cotton seed oil, corn oil or the like, or propylene glycol. The oral preparation can be manufactured by adding the differentiation inhibiting agent and/or compound of the present invention to, for example, a vehicle (for example, lactose, saccharose, starch or the like), a disintegrator (starch, calcium carbonate or the like), a binder (for example, starch, gum acacia, carboxymethyl cellulose, polyvinyl pyrrolidone, hydroxypropyl cellulose or the like), and a lubricant (for example, talc, magnesium stearate, polyethylene glycol 6000 or the like) to be subjected to compression molding followed by, when required, taste masking and coating for the purpose of an enteric preparation and a prolonged action by the method known per se. The usable coating agent includes, for example, hydroxypropylmethyl cellulose, ethyl cellulose, hydroxymethyl cellulose, hydroxypropyl cellulose, polyoxy ethylene glycol, Tween 80, Pluronic F68, cellulose acetate phthalate, hydroxypropylmethylcellulose phthalate, hydroxymethylcellulose acetate succinate, Eudragit (Rohm Pharma made, Germany: methacrylic acid-acrylic acid copolymer), or a pigment (example; colcothar, titanium dioxide or the like) after the method known per se. For an enteric preparation, an intermediate phase can be made between an enteric phase and a drug-containing phase by a method publicly known per se in order to separate both these phases.

To prepare drugs for an external use, the differentiation inhibiting agent and/or compound of the present invention can be made in a solid, semisolid or liquid drug for the external use according to a publicly known method. For example, the usable solid form as described above includes a powder composition of the intact compound of the present invention or that prepared by adding and blending the vehicle (example: glycol mannitol, starch, finely crystallized cellulose or the like), thickener (example: natural rubbers, cellulose derivatives, acrylic acid polymer or the like). The liquid form is prepared as an oily or aqueous suspension almost similar to the injection. The semisolid form is preferably an oily or aqueous gelatinous agent or ointment-like product. To all these forms and products may be added with a pH adjuster (example: carbonic acid, phosphoric acid, citric acid, hydrochloric acid, sodium hydroxide or the like) and an antiseptic agent (example: paraoxybenzoic acid esters, chlorobutanol, benzalkonium chloride or the like). For example, the compound of the present invention can be prepared as an oily or aqueous solid, semisolid or liquid suppository by a method publicly known per se. An oily base used for the composition as described above includes, for example, a glyceride of a higher fatty acid (example: cacao butter, Witepsols (Dynamite Nobel Corp, Germany,) or the like) or a medium fatty acid (example: Miglyols (Dynamite Nobel Corp, Germany,) or the like), or plant oil (example: sesame oil, soy bean oil, cotton seed oil or the like). The aqueous medium includes, for example, polyethylene glycols, propylene glycol, and the aqueous gelatinous medium includes, for example, natural rubbers, cellulose derivatives, vinyl polymers, acrylic acid derivatives or the like.

The prodrugs of the compounds (9) and (10) are compounds which are converted to the compound (9) or (10) having the stem cell proliferation action by an in vivo metabolic reaction by an enzyme and a gastric acid. The prodrug of the compounds (9) and (10) include: when the compounds (9) and (10) have an amino group, the compound produced by acylation, alkylation or phosphorylation of the amino group (example: the compounds produced by bonding an eicosanoyl, aranyl, pentylaminocarbonyl, (5-methyl-2-oxo-1,3-dioxolene-4-yl)methoxycarbonyl, tetrahydrofuranyl, pyrrolidylmethyl, pivaloyloxymethyl or tert-butyl to the amino groups of the compounds (9) and (10)); when the compounds (9) and (10) have a carboxyl group, the compound produced by esterification or amidation of the carboxyl group (example: the compounds produced by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolene-4-yl)methyl esterification, cyclohexyloxycarbonylethyl esterification or methylamidation of the carboxyl group of the compounds (9) and (10)). These compounds can be prepared by the publicly known method. The prodrugs of the compounds (9) and (10) may be those changeable to the compounds (9) and (10) according to a physiological condition, which have been described in "Iyakuhin no Kaihatsu (Development of Drugs)" Vol. 7, Bunsi Sekkei: p163-198, 1990, Hirokawa Syoten.

The prodrugs of the compounds (9) and (10) may be themselves or the pharmacologically acceptable salt. Such the salt includes salts made from, when the prodrugs of the compounds (9) and (10) have an acidic group such as carboxyl group, inorganic base (example: alkali metals such as sodium and potassium, alkali earth metals such as calcium and magnesium, transition metals such as zinc, iron, copper, or the like) or organic base (example: organic amine such as trimethyl amine, triethyl amine, pyridine, picoline, ethanolamine, diethanolamine, triethanolamine, dicyclohexylamine, N,N'-dibenzylethylenediamine, or the like or basic amino acid such as arginine, lysine, ornithine, or the like). When the prodrugs of the compounds (9) and (10) have a basic group such as an amino group, the salts made from inorganic acid and organic acid (example: hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluene sulfonic acid, or the like) or acid amino acid such as aspartic acid or glutamic acid are exemplified. The prodrugs of the compounds (9) and (10) may be either a hydrate or a nonahydrate. The compounds (9) and (10) may have 1 or 2 sites in the molecule capable of producing geometric isomers (cis-trans isomers) and the compound having the cis- and trans-isomers in an arbitrary proportion is included in the present invention. The compounds (10) may have 1 or more asymmetric carbons in the molecule and both of an R arrangement and S arrangement related to these asymmetric carbons are included in the present invention. The compounds (9) and (10) may be labeled with an isotope (example: $^3$H or $^{14}$C), or the like.

The prodrugs of the compounds (9) and (10) may be those prepared by binding, a polysaccharide (dextran, pluran, mannan, chitin, chitosan, or the like) with the compounds (9) and (10) in a reaction point which is an amino group, carboxyl group, hydroxyl group or the like. On the other hand, the prodrugs of the compounds (9) and (10) may be a complex prepared by inclusion in cyclodextrin (there are α form, β form and γ form, however, preferably β or γ0 form).

EXAMPLES

Examples as implementation of the present invention will be presented below. These examples are provided to help those skilled in the art for practice of the present invention. These examples do never restrict the scope of the present invention in any modes. In addition, modification is allowed in a range not going out of the scope of the present invention. The "room temperature" described in the following examples represents a range from 0 to 30° C. "%" means a percent by weight unless otherwise stated.

Example 1

(1) Preparation of a Mouse ES Cell Culture Medium

With a purpose to proliferate the ES cell, the factor was added to Dulbecco's modified Eagle medium (hereafter DMEM) (Invitrogen Corp. made, 11995) with a final concentration shown below to prepare an ES cell culture medium. 15% bovine fetus serum (Invitrogen Corp. made) or 15% knockout serum replacement: KSR (Invitrogen Corp. made), 0.1 mM β-mercaptoethanol (Sigma Corp. made), 1× nonessential amino acid stock (Invitrogen Corp. made, 11140-050), 2 mM L-Glutamine (Invitrogen Corp. made, 25030-081), $10^3$ unit/mL ESGRO (CHEMICON International Inc., made).

ESGRO contains a mouse LIF as the active ingredient. As the culture medium for ES cell differentiation inhibition assay, an assay medium was prepared by excluding ESGRO from the ES cell culture medium as described above.

(2) Culture of the Mouse ES Cell 5 mL of a sterilized 0.1% gelatin (SIGMA Corp. made, Type A: from porcinESkin, G2500) aqueous solution was added in a 6 cm diameter dish, and it was left stand at 37° C. for 30 minutes or more. After removal of gelatin aqueous solution, 2×$10^6$ mouse embryonic fibroblast cells (Invitrogen Corp. made, YE9284400) treated with mitomycin C (Kyouwa Hakkou Corp. made) was seeded and cultured using 5 mL of DNEM containing 10% fetal bovine fetus serum (Invitrogen Corp. made) at 37° C. in 5% $CO_2$ in an incubator (Tabai Espec Corp. made) for 5 hours or more. A mouse embryonic stem cell line D3ES cell (available from Rolf Kemler, Max Planck Institut for Immunbiologie, Stuheweg 51, D-79108, Freiburg, Germany) was seeded on a fibroblast cell feeder layer with a 6 cm diameter and cultured and proliferated using 5 mL-ES culture medium at 37° C. in 5% $CO_2$ in the incubator for 2 days.

(3) Preparation of a Mouse ES Cell

D3ES cells cultured after the above described (2) the method for culturing the ES cell was washed twice with PBS and, then, 0.25% trypsin solution (Invitrogen Corp. made, 15090-046) was added and incubated at 37° C. for 5 minutes to remove a colony of undifferentiated D3ES cells from the feeder. A 5 mL-ES cell culture medium was added, the cell colonies were dispersed by using a pipette with a small diameter and transferred to a 50 mL-sterilized tube, and centrifuged at 1000 rpm for about 5 minutes by using a centrifuge (TOMY SEIKO K.K.) to make pellets. The supernatant was discarded, cells were suspended again in a 20 mL fresh ES cell culture medium and seeded on a 15 cm diameter dish for cell culture, which had been previously coated with a 0.1% gelatin aqueous solution, and incubated at 37° C. for 20 minutes. After 20 minutes, the culture medium containing floating cells was collected by using a pipette, seeded again in the 15 cm diameter dish for cell culture, which had been previously coated with a 0.1% gelatin aqueous solution, and incubated at 37° C. for 20 minutes. The medium containing the floating cells was transferred to a 50 mL-sterilized tube, centrifuged at 1000 rpm for about 5 minutes by using a table centrifuge, and then, the supernatant was removed followed by suspending again in a 5 mL-ES cell assay medium to obtain the ES cell.

(4) ES Cell Differentiation Inhibiting Agent Assay 1

For the D3ES cell obtained by the preparation of the mouse ES cell as described in (3) above, 3×$10^2$ to 1×$10^3$ cells per well was seeded in 90 ml of the ES cell assay medium in a well of a 96-well cell culture dish (Falcon Corp. made, Cat. No. 3072, USA) coated previously with a 0.1% aqueous gelatin solution. A 10 µl of the differentiation inhibiting agent (A,B,C,D,E,F: A to D were ASINEX Corp. (Russia) made and E to F were purchased from PHARMEKS Corp. (Russia)) of the present invention or ESGRO, which was dissolved in dimethylsulfoxide (DMSO), or water, or the mixture, was added to each well to make 0.4 to 40 µg/mL, and culturing was carried out at 37° C. in 5% $CO_2$ incubator for 7 days. DMSO added to the medium was adjusted to make a final concentration of 0.1% or lower. On the other hand, to a control well was added only DMSO to make the final concentration of 0.1%. Structure of the compound A is presented in FIG. 1, and structures of the compound B to F are presented in FIG. 2.

(5) Alkaline Phosphatase Quantification 1

An alkaline phosphatase activity of the ES cell was quantified by using p-NITROPHENYLPHOSPHATE SOLUTION (MOSS Inc. made, PRODUCT NO. NPPD-1000, USA, or SIGMA Corp. made A-3469, USA made) (hereafter p-NPP.)

Figure 3:
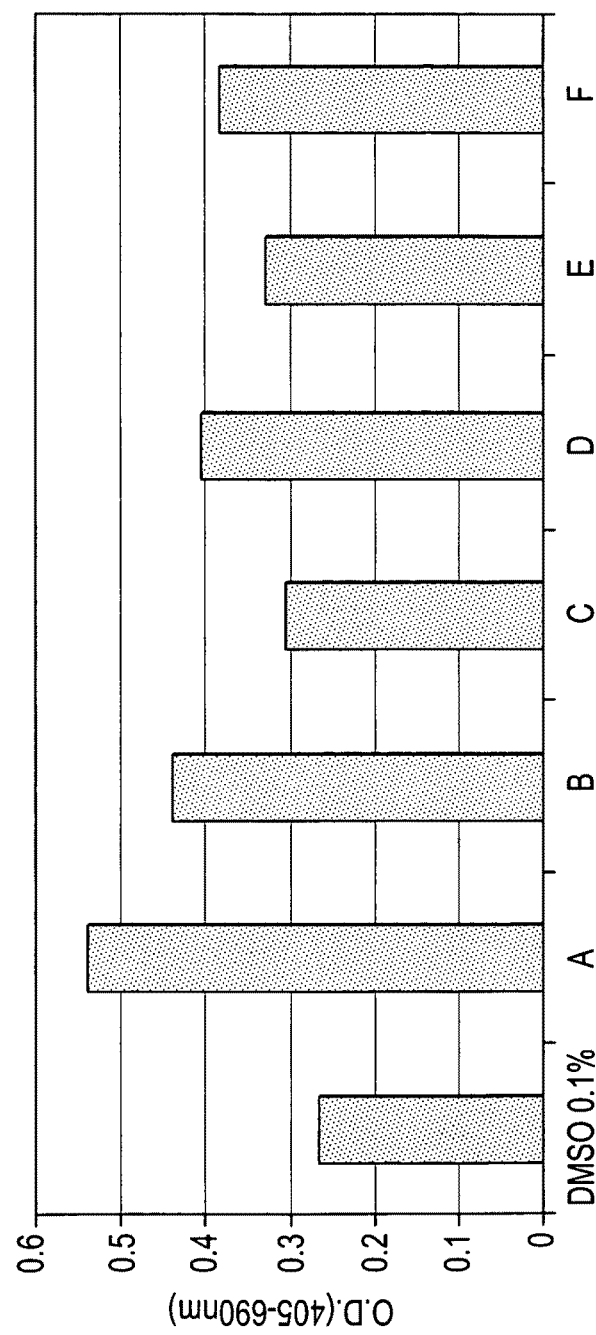
FIG. 3 shows a result of alkaline phosphatase quantification 1.

The medium was removed by sucking from individual wells of the ES cells cultured for 7 days according to the method described in ES cell differentiation inhibiting agent assay 1 as described above, and the cells were washed once with 100 µl of phosphate buffered saline (PBS) and, then, p-NPP 100 µl was added to each well to left stand at room temperature for 10 minutes. 12.5 µL of 8 M sodium hydroxide aqueous solution was added to each well to stop the reaction. An absorbance at 405 nm (O.D.405) and absorbance at 690 nm (O.D.690) were measured by using a spectrophotometer (Molecular Devices Corp. made, type: SPECTRA MAX190), and a value calculated by O.D.405-O.D.690 was determined as the alkaline phosphatase activity. FIG. 3 shows the graphed result of the quantification.

The differentiation inhibiting agent, the compound A to F, of the present invention increased significantly the alkaline phosphatase activity in comparison with the control, DMSO (0.1%). From this, it is known that the differentiation inhibiting agent of the present invention supported the culture of undifferentiated ES cells.

(6) Alkaline Phosphatase Staining 1

The ES cells were stained by using an alkaline phosphatase kit (SIGMA Diagnostic Corp. made, Cat. No. 86-R). The medium was removed by sucking from individual wells of the ES cells cultured by the method described in (4) ES cell differentiation inhibiting agent assay 1 as described above, and the cells were washed once with 2 mL of phosphate buffered saline (PBS), and then 2 mL of a cell-fixing solution (25 mL citric acid solution (SIGMA Corp. made, Cat. No. 91-5), 65 mL acetone, 8 mL 37% formaldehyde) was added to each well to be left stand at room temperature for 30 seconds.

The fixing solution was removed by sucking, and 2-mL of deionized water was added to individual wells and left stand at room temperature for 45 seconds.

Figure 4:
FIG. 4 shows a result of alkaline phosphatase staining 1.

The deionized water was removed by sucking and, then, a 2-mL of alkaline phosphatase staining solution (1 mL sodium nitrite solution, 1 mL Fast Red Violet LB salt solution, 1 mL naphthol AS-BI alkaline solution, 45 mL distilled water) was added to each well and left stand at room temperature for 15 minutes followed by removal of the staining solution by sucking, and washing was carried out with 2 mL of deionized water. Staining images were compared among the ES cells cultured in the absence of ESGRO being a negative control, the ES cells cultured in the presence of ESGRO (1000 units/mL) being a positive control, and the ES cells cultured in the presence of the compound B (4 μg/mL) which is the differentiation inhibiting agent of the present invention (refer to FIG. 4). The ES cells cultured in presence of the compound B were, in comparison with the ES cells cultured in the absence of ESGRO, stained significantly more densely showing that the ES cells have a higher alkaline phosphatase activity. Moreover, the differentiation inhibiting agent of the present invention allowed to form an undifferentiated colony equal to that of the ES cells cultured in the presence of ESGRO being the positive control. From this result, the differentiation inhibiting agent of the present invention supported strongly proliferation of the ES cells in the undifferentiated state.

In this connection, for the compound A and C to F also, staining was similar to the compound B.

(7) STAT3 Activation Assay 1

Figure 5:
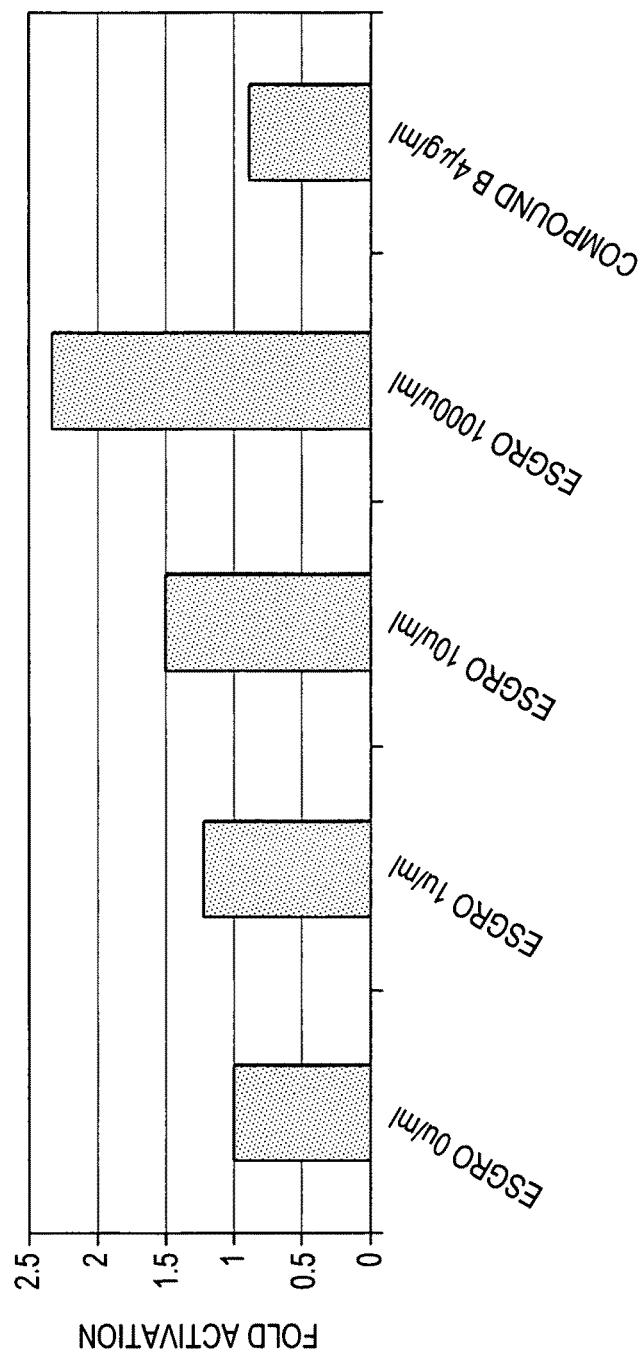
FIG. 5 shows a result of STAT3 activation assay 1.

For the D3ES cells prepared by the method described in (3) preparation of a mouse ES cell of Example 1, $1 \times 10^5$ cells in 500 μL ES medium were seeded in a well of a 24-well cell culture dish (Falcon Corp. made, Cat No. 3047, USA) coated previously with a 0.1% aqueous gelatin solution, followed by culturing at 37° C. in 5% $CO_2$ incubator for 12 hours to 24 hours. Next, by using LipofectAMINE 2000 (Invitrogen Corp. made, USA) by a protocol attached to the product, 0.9 μg per 1 well of pSTAT3-TA-Luc or pTA-Luc vector (Clontech Corp. made, USA) was transfected into the ES cells. In addition, 0.1 μg of an internal control, pRL-TK vector (Promega Corp. made, USA) was transfected at the same time for each well. Following culturing at 37° C. in 5% $CO_2$ incubator for 4 hours, the medium was sucked, and the cells were washed twice with PBS and, then, a 500 μL-ES assay medium was added to each well. Subsequently, a 50 μL of the differentiation inhibiting agent, which was dissolved in dimethylsulfoxide (DMSO) or water, or their mixture to make 0.4 to 40 μg/mL per each well, or ESGRO which was diluted with the ES assay medium to make 10 to 10,000 unit/mL, was added, and culturing was carried out at 37° C. in 5% $CO_2$ incubator for 6 to 24 hours. Next, by using PicaGene Dual SeaPansy (Toyo Ink made, Japan) by the attached protocol, a luminescence signal generated by a luciferase reporter enzyme of each cell was measured. As shown in FIG. 5, ESGRO dose-dependently accelerated the expression of the reporter enzyme by pSTAT3-TA-Luc and, on the contrary, the compound B of the present invention did not induce the expression of the reporter enzyme.

Also, by performing the same experiments for the compounds A, C to F, the presence or absence of the expression of the reporter enzyme can be confirmed.

Example 2

(1) ES Cell Differentiation Inhibition Assay 2

For the D3ES cells prepared by the method described in (3) preparation of a mouse ES cell of Example 1, $8 \times 10^4$ cells were seeded in a 10 cm-diameter cell culture dish coated previously with a 0.1% aqueous gelatin solution to make 10 mL of the ES cell assay medium. 1 mL of the differentiation inhibiting agent A to F, which were dissolved in dimethylsulfoxide (DMSO) or culture medium or their mixture to make 40 μg/mL per each dish, or ESGRO, which was adjusted to make $10^4$ unit/mL, was added, and culturing was carried out at 37° C. in 5% $CO_{62}$ incubator for 7 days. To the culture medium was added DMSO to make the final concentration 0.1% or lower.

(2) Isolation of RNA 1

A total RNA was extracted from the ES cells cultured by the method described in (1) ES cell differentiation inhibition assay 2 as described above, by using ISOGEN (K.K. Nippon Gene, Japan made) by the attached method. First, the medium was removed from the dish after the culture, the cells were washed twice with 10 mL of PBS, and dissolved in 1 mL of ISOGENE. After leaving stand at room temperature for 5 minutes, the solution was collected in a 1.5 mL Eppendorf tube. 0.2 mL of chloroform (Wako Pure Chemical Industries made) was added, shaken for 15 seconds and, then, left stand at room temperature for 2 or 3 minutes. The solution was centrifuged at 4° C. at 10000 rpm for 10 minutes by using a micro centrifuge (TOMY SEIKO Corp. made). 400 μL of the supernatant was transferred to a fresh 1.5 mL Eppendorf tube, 500 μL of isopropanol (Wako Pure, Chemical Industries made) was added, and left stand at room temperature for 10 minutes, and, then, centrifuged at 4° C. at 10000 rpm for 10 minutes by using the micro centrifuge. After the supernatant was removed, 1 mL of a 70% aqueous ethanol solution was added followed by shaking and, then, centrifugation was carried out at 4° C. at 10000 rpm for about 5 minutes by using, the micro centrifuge. After the supernatant was removed, a precipitation was dried and dissolved in 30 μL of distilled water to obtain the total RNA solution.

2 μg of the thus obtained total RNA was used as a template to synthesize a cDNA according to the attached protocol by using Deoxyribonuclease I (Amplification Grade)(Invitrogen Corp. made), Oligo(dT) 12-18 primer (Invitrogen Corp. made, 18418-012) and Omniscript reverse transcriptase (QIAGEN Corp, made). Thus, a reaction solution was prepared by adding 1 μL of 10× DNaseI Reaction Buffer, 1 μL of 10× DNaseI (all were made by Invitrogen Corp.) and distilled water to 2 μg of total RNA to make 10 μL in total, and the mixture was incubated at room temperature for 10 minutes. 1 μL of 25 mM EDTA solution was added and heated at 65° C. for 10 minutes. The mixture was cooled to room temperature, and then, 2 μL of 10× Buffer RT, 2 μL of 5 mM dNTP Mix, 2 μL of Oligo(dT) 12-18 primer, 0.25 μL of RNaseOUT (Invitrogen Corp. made, 10777-019) and 1 μL of Omniscript Reverse Transcriptase were added, and RNase-free purified water was added to give the total volume of 20 μL, and the mixture was incubated at 37° C. for 60 minutes to obtain cDNA solution. A portion of the synthesized cDNA obtained in such the way was diluted 5 folds with distilled water, and 2 μL of the solution was used as the template to conduct PCR by using Light Cycler-Fast Start DNA Master SYBR Green I Kit (Roche Diagnostics Corp. made) according to the attached protocol. The expression levels of the Oct-3/4 gene and glyceraldehyde-3-phosphate dehydrogenase (GAPDH) gene as the internal standard were measured. For amplifying the Oct-3/4 gene, sense primer OCT3 up (SEQ ID No.: 1) and antisense primer Oct3 down (SEQ ID No.: 2) were used, and for amplifying the GAPDH gene, sense primer GAPDH up (SEQ ID No.: 3) and antisense primer GAPDH down (SEQ ID No.: 4) were used. The composition of the PCR reaction solution and the reaction condition will be each presented below.

| Composition of the PCR reaction solution for Oct-3/4 gene quantification | |
|---|---|
| 25 mM MgCl$_2$ | 1.6 μL |
| 5 μM sense primer | 1.0 μL |
| 5 μM antisense primer | 1.0 μL |
| cDNA (5-fold dilution) | 2.0 μL |
| Light Cycler-Fast Start DNA Master | 2.0 μL |
| H$_2$O | 12.4 μL |
| Total | 20.0 μL |

| Reaction condition of PCR for Oct-3/4 gene quantification | | | | | | |
|---|---|---|---|---|---|---|
| Step | Program | Cycle No. | Section | Temp. (° C.) | Time (sec) | Temp. change rate (° C./sec) |
| 1 | Denature | 1 | 1 | 95 | 600 | 20 |
| 2 | Amplification | 45 | 1 | 95 | 15 | 20 |
| | | | 2 | 55 | 10 | 20 |
| | | | 3 | 72 | 20 | 20 |
| 3 | Melting curve analysis | 1 | 1 | 95 | 0 | 20 |
| | | | 2 | 65 | 10 | 1 |
| | | | 3 | 96 | 0 | 0.1 |

Figure 6:
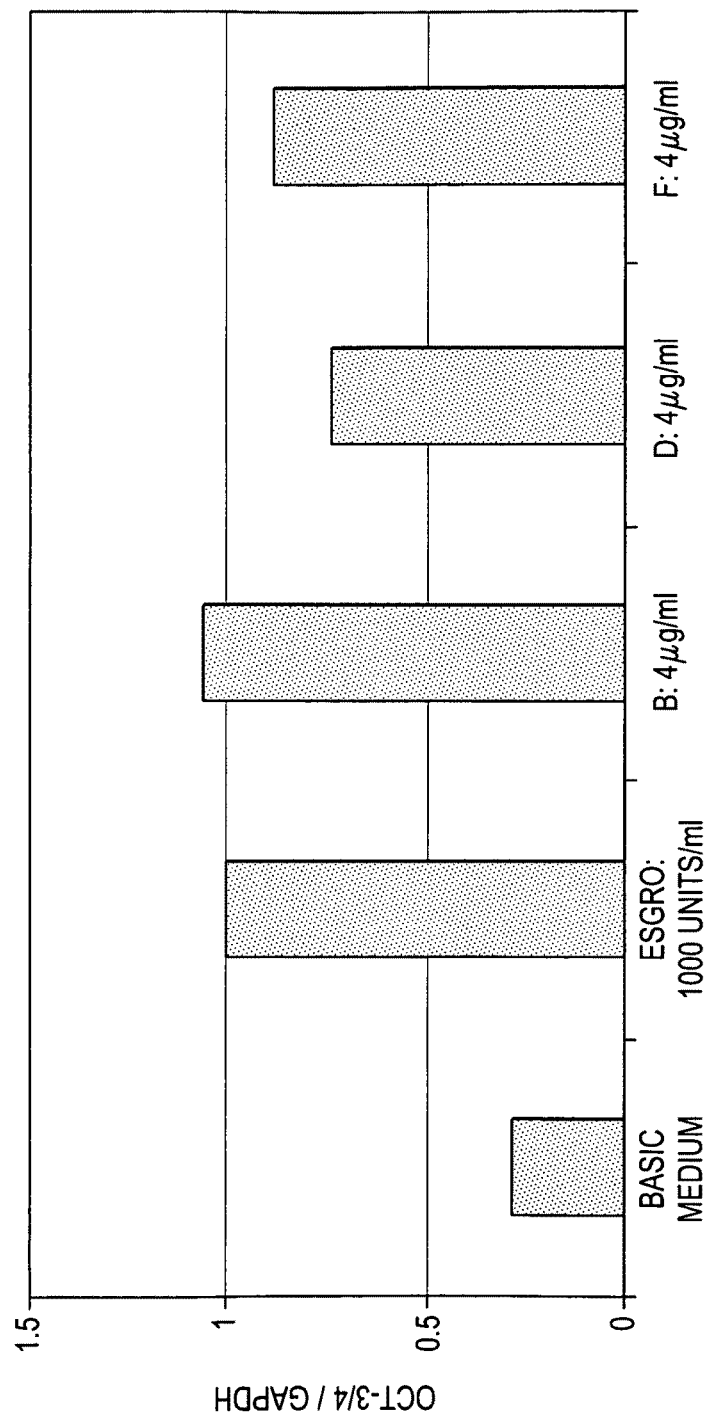
FIG. 6 shows an Oct-3/4 gene expression level.

The expression of Oct-3/4 gene of the ES cells cultured in the presence of the differentiation inhibiting agents (B, D and F) of the present invention was significantly promoted in comparison with the ES cells cultured in the medium without the differentiation inhibiting agent, and showed the effect of keeping the expression of the Oct-3/4 gene, comparable with 1,000 units/mL of ESGRO (FIG. 6). In conclusion, it was found from the expression level of the Oct-3/4 gene that the differentiation inhibiting agents (B. D and F) of the present invention maintain undifferentiation of the ES cell. From the result as described above, it was shown that, also from the expression level of the Oct-3/4 gene, the differentiation inhibiting agents B, D and F of the present invention keeps the undifferentiation state of the ES cell.

Further, the same examination was carried out for the differentiation inhibiting agents A, C and E and, similarly to the differentiation inhibiting agents (B, D and F), these compounds maintained the expression of the Oct-3/4 gene. In other words, these compounds maintained the undifferentiation of the ES cell.

(3) ES Cell Differentiation Inhibition Assay 3

For the D3ES cells prepared by the method described in (3) preparation of a mouse ES cell of Example 1, 7.85×10$^5$ cells were seeded in a 10 cm-diameter cell culture dish coated previously with a 0.1% aqueous gelatin solution to make 10 mL of the ES cell assay medium. The differentiation inhibiting agent B of the present invention in the final concentration of 4 μg/mL or ESGRO in the final concentration of 1×10$^3$ unit/mL was added to each dish, and culturing was carried out at 37° C. in 5% CO$_2$ incubator for 1 day.

(4) Isolation of RNA 2

The total RNA was extracted from the ES cell cultured by the method shown in (3) ES cell differentiation inhibition assay 3 as described above by using ISOGEN (K.K. Nippon Gene Corp. Japan made) by the attached method. In this method, the cell was collected in a 15 mL sterilized tube, centrifuged at 1,000 rpm for about 5 minutes by using the table centrifuge (TOMY SEIKO made) to make pellets. The supernatant was removed, the pellets were washed twice with 10 mL of PBS, and then, transferred to a 1.5 mL Eppendorf tube. The pellets were dissolved in 1 ml ISOGENE and left stand at room temperature for 5 minutes and, then, added with 0.2 mL of chloroform (Wako Pure Chemicals), shaken for 15 seconds, and left stand at room temperature for 2 or 3 minutes. Centrifugation was carried out at 4° C. at 10,000 rpm for 15 minutes by using the micro centrifuge (TOMY SEIKO made), 400 μL of the supernatant was transferred to a fresh 1.5 mL Eppendorf tube. 500 μL of isopropanol (Wako Pure Chemicals) was added and the mixture was left stand at room temperature for 10 minutes and, then, was centrifuged at 4° C. at 10,000 rpm for 10 minutes by using the micro centrifuge. The supernatant was removed and, then, 1 mL of a 70% ethanol aqueous solution was added. The mixture was shaken and then was centrifuged at 4° C. at 10,000 rpm for about 5 minutes by using the micro centrifuge. The supernatant was removed and the precipitation was dried and, then, dissolved in 30 μL of distilled water to obtain the total RNA solution.

The cDNA was synthesized by using 2 μg of the total RNA obtained by such the way as the template, using DeoxyribonucleaseI (Amplification Grade) (Invitrogen Corp. made) and SuperScript III First-Strand Synthesis System for RT-PCR (Invitrogen Corp. made, 18080-051) by the attached protocol. In this step, 1 μL of 10× DNaseI Reaction Buffer, 1 μL of 10× DNaseI (all these were of Invitrogen Corp. made) were added to 2 μg of the total RNA to give the total volume of 10 μL by adding distilled water to prepare the reaction solution, and then incubation was carried out at room temperature for 10 minutes. 1 μL of 25 mM EDTA solution was added, and the mixture was heated at 65° C. for 10 minutes and then, cooled to room temperature. 8 μL of the reaction solution was taken out, and 1 μL of 50 mM Oligo(dT) 20 primer and 1 μL of 10 mM dNTP Mix were added, and incubation was carried out at 65° C. for 5 minutes. The reaction solution was placed on ice for 1 minute, and then 2 μL of 10× RT Buffer, 4 μL of 25 mM MgCl$_2$, 2 μL of 0.1 M DTT, 1 μL of RNaseOUT (Invitrogen Corp. made) and 1 μL of SuperScript III RT were added for incubation at 50° C. for 50 minutes. Subsequently, incubation was carried out at 85° C. for 5 minutes, and then the mixture was left stand on ice for 1 min. 1 μL of RNaseH was added, and incubation was carried out at 37° C. for 20 minutes to obtain cDNA. PCR was conducted by diluting a portion of the synthetic cDNA thus obtained 5 folds with distilled water and using 2 μL of it as the template and also using Light Cycler-Fast Start DNA Master SYBR Green I Kit (Roche Diagnostics Corp. made) by the attached protocol. The expression level of the Nanog gene and the glyceraldehyde-3-phosphate dehydrogenase (GAPDH) gene as the internal standard were measured. For amplifying the Nanog gene, sense primer Nanog_up (SEQ ID No.: 5) and antisense primer Nanog-down (SEQ ID No.: 6) were used, and for amplifying the GAPDH gene, sense primer GAPDH_up (SEQ ID No.: 3) and antisense primer GAPDH_down (SEQ ID No.: 4) were used. The composition of the PCR reaction solution and the reaction condition will be each presented below.

| Composition of the PCR reaction solution for the Nanog gene quantification | |
|---|---|
| 25 mM MgCl$_2$ | 2.4 μL |
| 5 μM sense primer | 1.0 μL |
| 5 μM antisense primer | 1.0 μL |
| cDNA (5-fold dilution) | 2.0 μL |
| Light Cycler-Fast Start DNA Master | 2.0 μL |
| H$_2$O | 11.6 μL |
| Total | 20.0 μL |

| Reaction condition of PCR for Nanog gene quantification | | | | | | |
|---|---|---|---|---|---|---|
| Step | Program | Cycle No. | Section | Temp. (° C.) | Time (sec) | Temp. change rate (° C./sec) |
| 1 | Denature | 1 | 1 | 95 | 600 | 20 |
| 2 | Amplification | 45 | 1 | 95 | 15 | 20 |
| | | | 2 | 58 | 10 | 20 |
| | | | 3 | 72 | 20 | 20 |
| 3 | Melting curve analysis | 1 | 1 | 95 | 0 | 20 |
| | | | 2 | 65 | 10 | 1 |
| | | | 3 | 96 | 0 | 0.1 |

Figure 7:
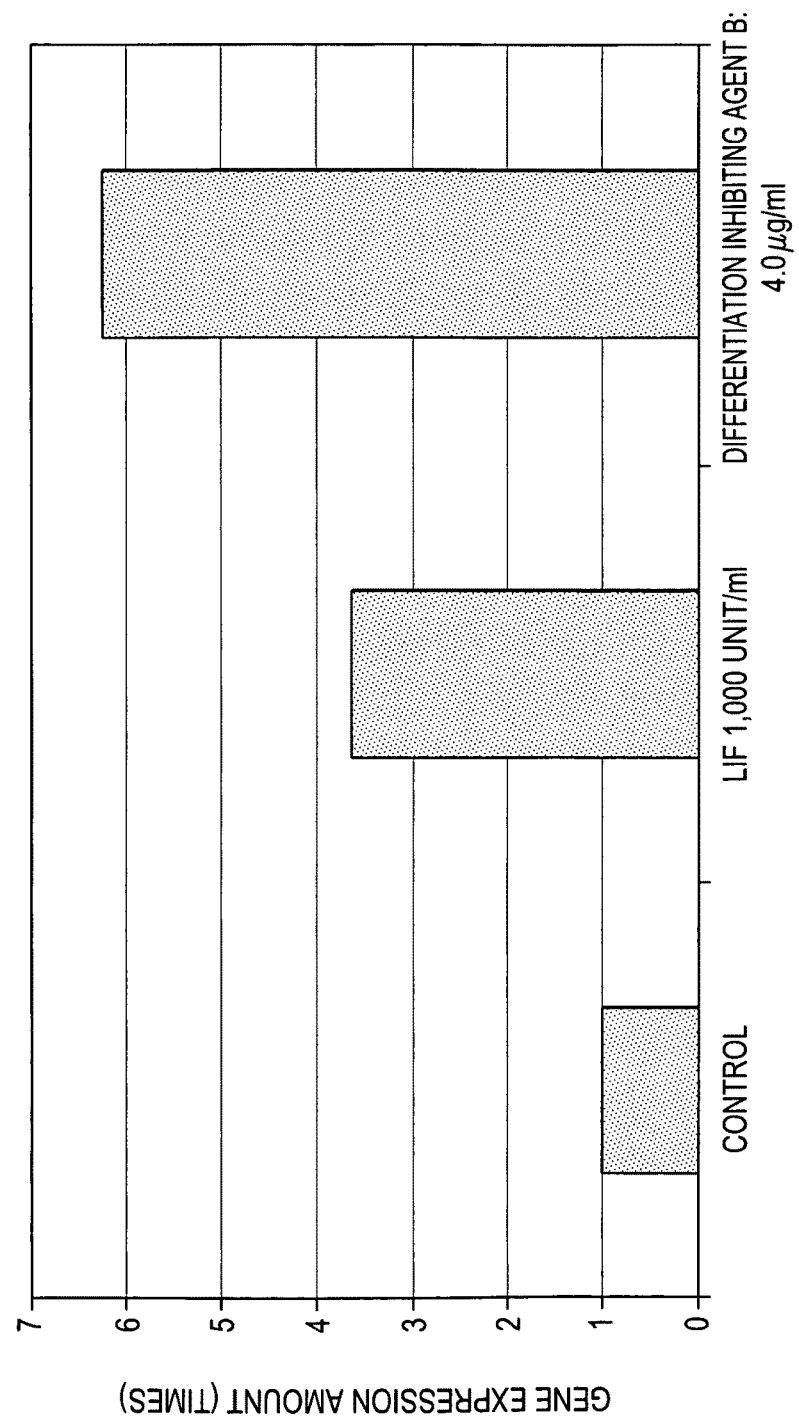
FIG. 7 shows a nanog gene expression level.

The expression level of Nanog gene of the ES cells cultured in the presence of the differentiation inhibiting agents B of the present invention increased significantly in comparison with the ES cells cultured in the medium without the differentiation inhibiting agent and the ES cells cultured in the medium containing 1,000 units/mL of ESGRO (FIG. 7). In conclusion, it was found from the expression level of the Nanog gene that the differentiation inhibiting agents B of the present invention has the effect of maintaining undifferentiation of the ES cell.

Further, the same examination was carried out for the differentiation inhibiting agents A, C, D, E and F and the expression level of the Nanog gene increased similarly to the differentiation inhibiting agents B. That is, it was shown that they have the activity of keeping the undifferentiation state of the ES cell.

(5) Evaluation of the Expression Level of SSEA-1 Antigen 1

Figure 8:
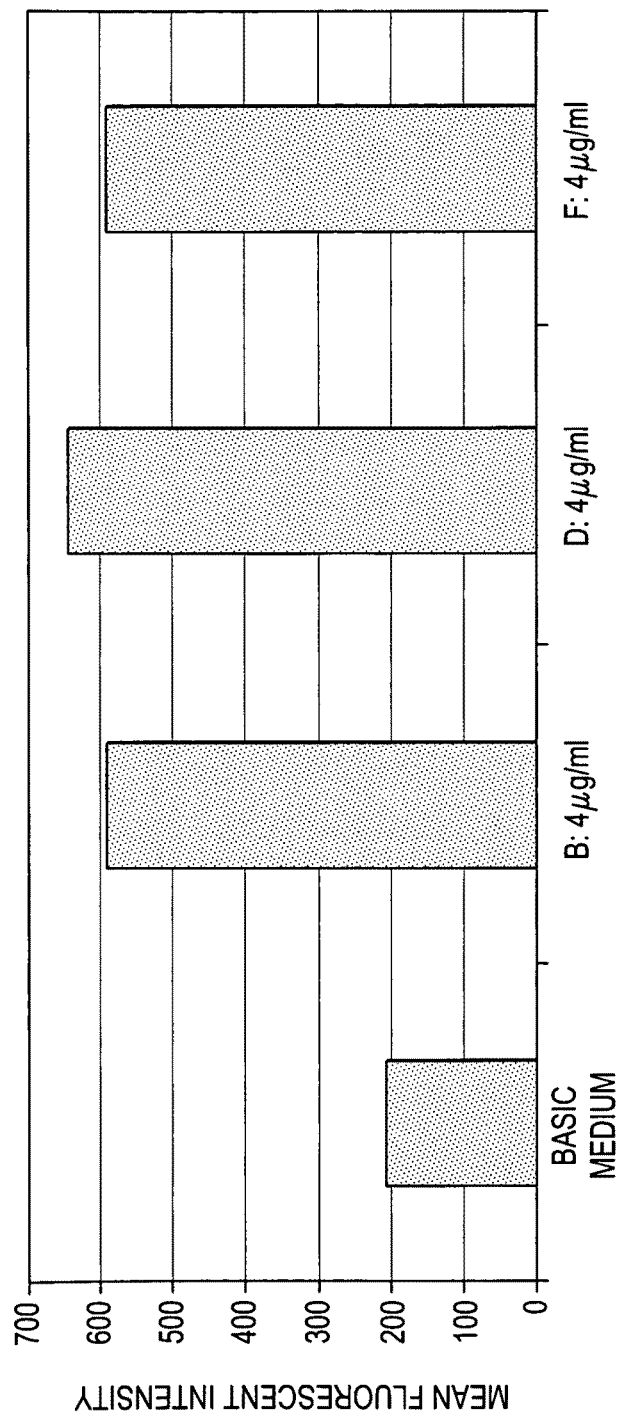
FIG. 8 shows a result of an average fluorescent strength in expression level evaluation 1 of SSEA-1 antigen.

The cells cultured in (1) ES cell differentiation inhibition assay 2 as described above were washed twice with PBS, and were removed from the dish with a cell scraper. 300 μL of Hanks balanced salt solution (HBSS, Invitrogen Corp. made) containing 2% FBS was added to give 6×10$^5$ cells. 30 μL of MX-SSEA-1 antibody (Kyowa Medex Corp. made) diluted 50 folds with HBSS was added, and left stand for 40 minutes on ice. The cells were washed twice with HBSS (1 mL) and, then, dispersed again in HBSS (300 μL), and 30 μL of FITC-Goat anti Mouse IgM antibody (ZYMED Corp. made) diluted 20 folds with HBSS was added and, then, left stand on ice for 30 minutes in shielded light. The cells were washed twice with HBSS (1 mL) and, then, dispersed again in HBSS (1 mL), added with 100 μL of 20 μg/mL PI solution (Dojindo Corp. made) to obtain a sample used for flow cytometry. The sample used for flow cytometry was measured after passed through a nylon mesh with a 100 μm pore size to eliminate a coagulated mass. A flow cytometer used was FACS Calibur (BECTON DICKINSON Corp. made) and software applied for collection and analysis of data of the measuring condition was CELL Quest (BECTON DICKINSON Corp. made). The result is shown in FIG. 8. An average fluorescence intensity per 1 cell, in other words, an SSEA-1 antigen expression intensity per 1 cell, of the cells cultured by adding each differentiation inhibiting agent, was increased significantly in comparison with the cells cultured in the medium without the differentiation inhibiting agent. The same experiment was carried out for the differentiation inhibiting agents A, C and E and the expression level of the SSEA-1 was significantly high as well. Thus, it was shown that the differentiation inhibiting agents of the present invention maintain the undifferentiated ES cell.

Example 3

The same experiment was carried out for the indole derivatives a to o and the following results were obtained.

(1) ES Cell Differentiation Inhibition Assay 4

For the D3ES cells prepared by the method described in (3) preparation of a mouse ES cell of Example 1, 3200 cells/well were seeded on a 96-well cell culture dish (Falcon Corp. made, Cat. No. 3072, USA) coated previously with a 0.1% aqueous gelatin solution to make 100 μL of the ES cell assay medium. Subsequently, 10 μL of the differentiation inhibiting agent of the present invention (a to o: a and j to m were purchased from IF LAB Ltd., Ukraine, b, c, f and n were from PHARMEKS Corp., Russia, d, e and o were from SPECS Corp., The Netherlands, g to i were from CHEMBRIDGE Corp., USA), which was dissolved in dimethylsulfoxide (DMSO) or water, or their mixture to make 0.4 to 40 μg/mL per each well, or ESGRO was added, and culturing was carried out at 37° C. in 5% CO$_2$ incubator for 4 days. The final concentration of DMSO in the culture medium was 0.1% or lower. On the other hand, to a control well was added only DMSO to make the final concentration 0.1%. The structures of the differentiation inhibiting agents a to o are presented in FIG. 9.

(2) Alkaline Phosphatase Quantification 2

Figure 10:
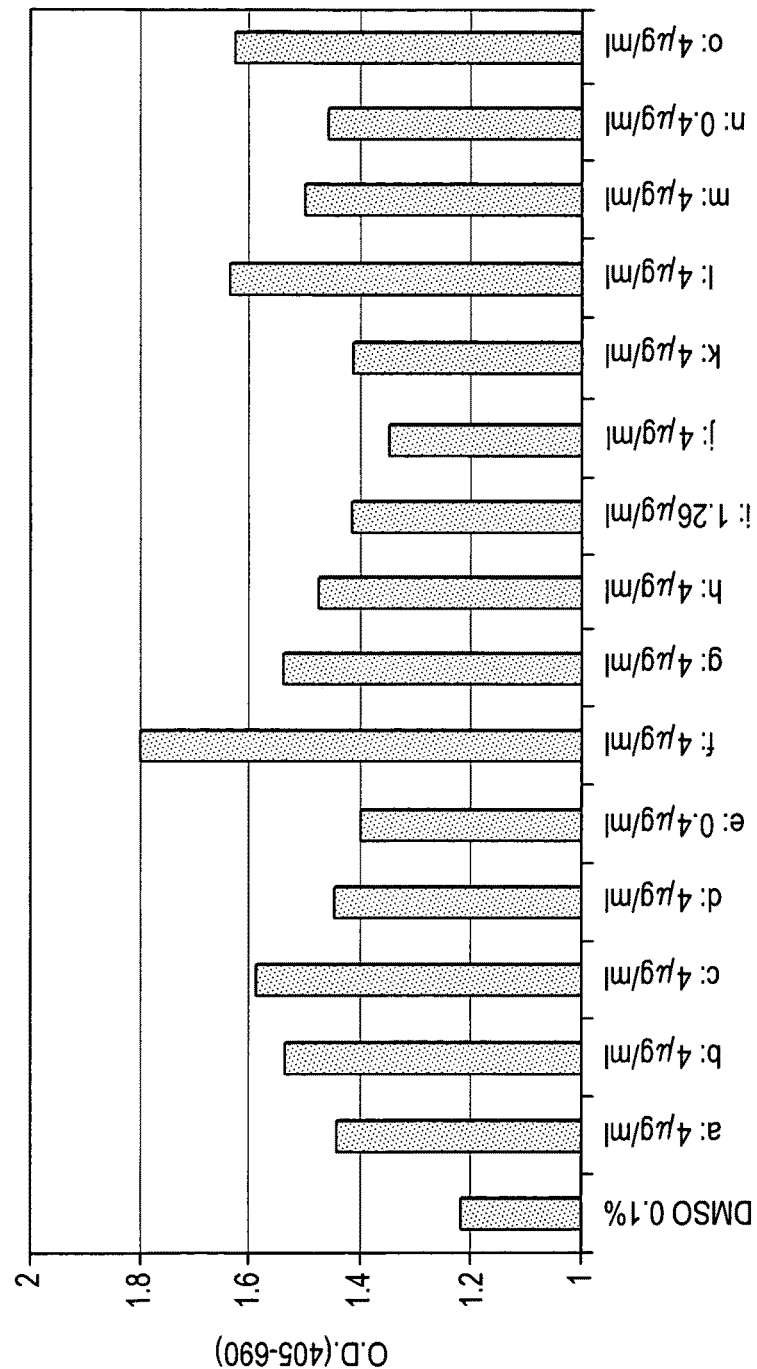
FIG. 10 shows a result of alkaline phosphatase quantification 2 when the differentiation inhibiting agent according to the present invention is used.

The alkaline phosphatase activity of the ES cell was quantified by using p-NITROPHENYLPHOSPHATE SOLUTION (MOSS Inc. made PRODUCT NO. NPPD-1000, USA; or SIGMA Corp. made A-3469, USA made) (hereafter p-NPP). The medium was removed by sucking from individual wells of the ES cells cultured for 4 days according to the method described in (1) ES cell differentiation inhibition assay 4 as described above, and the cells were washed once with 100 μL of phosphate buffered saline (PBS), and then 100 μL of p-NPP was added to each well to left stand at room temperature for 10 minutes. 12.5 μL of an 8 M sodium hydroxide aqueous solution was added to each well to stop the reaction. The absorbance at 405 nm (O.D.405) and absorbance at 690 nm (O.D.690) were measured by using a spectrophotometer (Molecular Devices Corp. made, type: SPECTRA MAX190), and the value calculated from O.D.405-O.D.690 was determined as the alkaline phosphatase activity. FIG. 10 shows the graphed result of the quantification. The differentiation inhibiting agents, the compounds a to o, of the present invention increased significantly the alkaline phosphatase activity in comparison with the control, DMSO (0.1%). From this, it is known that the differentiation inhibiting agent of the present invention supported the culture of the undifferentiated ES cells.

(3) ES Cell Differentiation Inhibition Assay 5

For the D3ES cells prepared by the method described in (3) preparation of the mouse, ES cell of Example 1, $8 \times 10^4$ cells were seeded on a 10 cm-diameter cell culture dish coated previously with a 0.1% aqueous gelatin solution to make 10 mL of the ES cell assay medium, 1 mL of the differentiation inhibiting agent (a to o) of the present invention, which was dissolved in dimethylsulfoxide (DMSO) or culture medium, or their mixture to make 40 μg/mL per each dish, or ESGRO was added, and culturing was carried out at 37° C. in 5% $CO_2$ incubator for 4 days. The final concentration of DMSO in the culture medium was 0.1% or lower.

(4) Evaluation of the Expression Level of SSEA-1 Antigen 2

Figure 11:
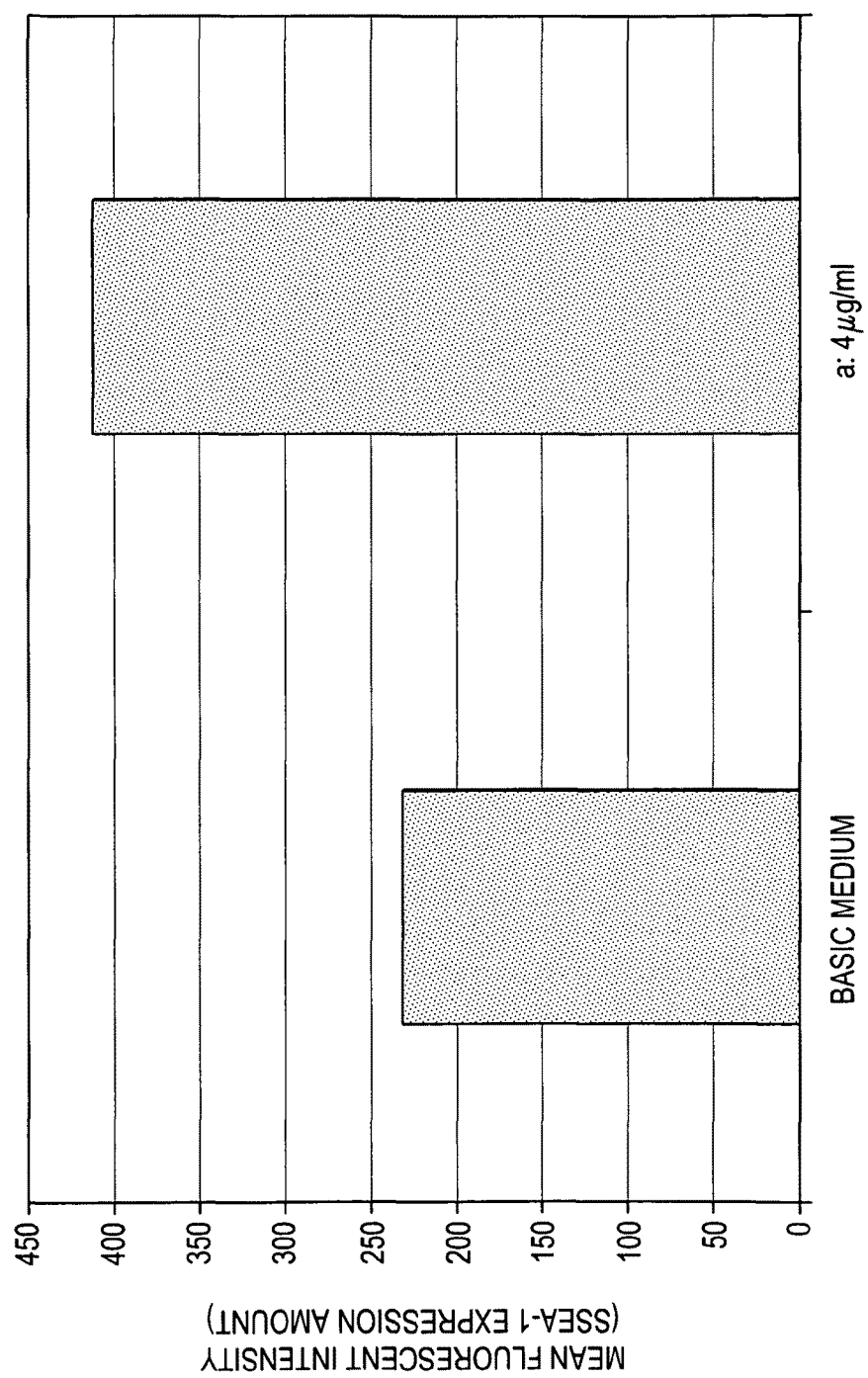
FIG. 11 shows a result of an average fluorescent strength in expression level evaluation 2 of SSEA-1 antigen.

The cells cultured in (3) ES cell differentiation inhibition assay 5 as described above were washed twice with PBS, and were removed from the dish with a cell scraper. 300 μL of Hanks balanced salt solution (HBSS, Invitrogen Corp. made) containing 2% FBS was added to make cell number in $6 \times 10^5$. 30 μL of MX-SSEA-1 antibody (Kyowa Medex Corp. made) diluted 50 folds with HBSS was added and left stand for 40 minutes on ice. The antigen was washed twice with HBSS (1 mL) and, then, dispersed again in HBSS (300 μL), and 30 μL of FITC-Goat anti Mouse IgM antibody (ZYMED Corp. made) diluted 20 folds with HBSS was added and, then, left stand on ice for 30 minutes in shielded light. The cells were washed twice with HBSS (1 mL) and, then, dispersed again in HBSS (1 mL), added with 100 μL of 20 μg/mL PI solution (Dojindo Corp. made) to obtain the sample used for flow cytometry. The sample used for flow cytometry was measured after passed through the nylon mesh with the 100 μm pore size to eliminate the coagulated mass. The flow cytometer used was FACS Calibur (BECTON DICKINSON Corp. USA made) and software applied for collection and analysis of data of the measuring condition was CELL Quest (BECTON DICKINSON Corp. USA made). The result is shown in FIG. 11. The average fluorescence intensity per 1 cell, in other words, the SSEA-1 antigen expression intensity per 1 cell, of the cells cultured by adding each differentiation inhibiting agent was increased significantly in comparison with the cells cultured in the medium without the differentiation inhibiting agent. The same experiment was carried out for the differentiation inhibiting agents b to o and the expression level of the SSEA-1 was significantly high as well. It was shown that the differentiation inhibiting agents of the present invention maintain the undifferentiated ES cells.

(5) STAT3 Activation Assay 2

Figure 12:
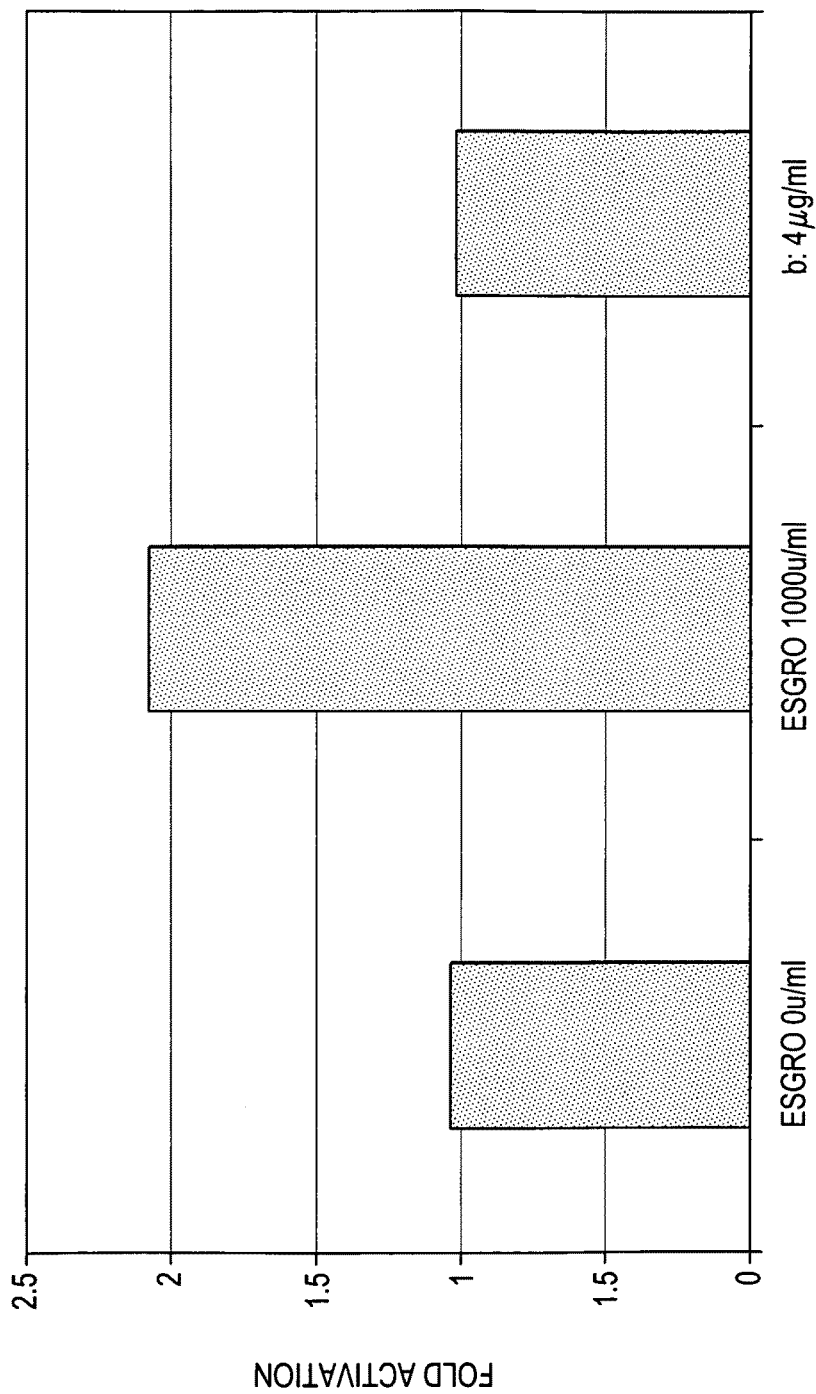
FIG. 12 shows a result of STAT3 activation assay 2.

For the D3ES cells prepared by the method described in (3) preparation of the ES cell of Example 1, $1 \times 10^5$ cells were seeded on a 24-well cell culture dish (Falcon, Cat. No. 3047, USA) coated previously with a 0.1% aqueous gelatin solution to make the ES cell medium in 500 μL per 1 well followed by culturing at 37° C. in 5% $CO_2$ incubator for 12 hours to 24 hours. Next, by using LipofectAMINE 2000 (Invitrogen Corp. made, USA) by a protocol attached to the product, 0.9 μg/well of pSTAT3-TA-Luc or pTA-Luc vector (Clontech Corp. made, USA) was transfected into the ES cells. On the other hand, 0.1 μg of the internal control, pRL-TK vector (Promega Corp. made, USA) was transfected at the same time for each well. Following culturing at 37° C. in 5% $CO_2$ incubator for 4 hours, the medium was sucked and washed twice with PBS and, then, the 500 μL-ES assay medium was added to each well. Subsequently, 50 μL of the differentiation inhibiting agent, which was dissolved in dimethylsulfoxide (DMSO) or water, or their mixture to make 0.4 to 40 μg/mL per each well, or ESGRO, which was diluted with the ES assay medium to make 10 to 10,000 unit/mL, was added, and culturing was carried out at 37° C. in 5% $CO_2$ incubator for 6 to 24 hours. Next, by using PicaGene Dual SeaPansy (Toyo Ink, Japan) by the attached protocol, the luminescence signal generated by the luciferase reporter enzyme of each cell was measured. As shown in FIG. 12, ESGRO promoted the expression of the reporter enzyme by pSTAT3-TA-Luc and, on the contrary, the compound b of the present invention did not induce the expression of the reporter enzyme.

Also, by carrying out the same experiments for the compound a, c to o, the presence or absence of the expression of the reporter enzyme can be confirmed.

Example 4

Subculture of ES Cells

For the ES cells prepared by the method described in (3) preparation of the mouse ES cell of Example 1, $3 \times 10^5$ cells were seeded on a 6 cm-diameter cell culture dish coated previously with a 0.1% aqueous gelatin solution to make 4.5 mL of the ES cell assay medium. 0.5 mL of the differentiation inhibiting agent (A to F and a to o) of the present invention, which was dissolved in dimethylsulfoxide (DMSO) or culture medium, or their mixture to make 10 to 40 μg/mL per each dish, or $10^4$ units/mL of ESGRO was added. The final concentration of DMSO in the culture medium was 0.1% or lower. As the control, only DMSO was made the final concentration in 0.1% by adding 0.5 mL of a 1% concentration solution diluted with the medium. Culturing was conducted at 37° C. in 5% $CO_2$ incubator for 7 to 30 days. The medium was replaced every day, and the cells were passaged to make $3 \times 10^5$ cells/dish for every 2 to 3 days.

Figure 13:
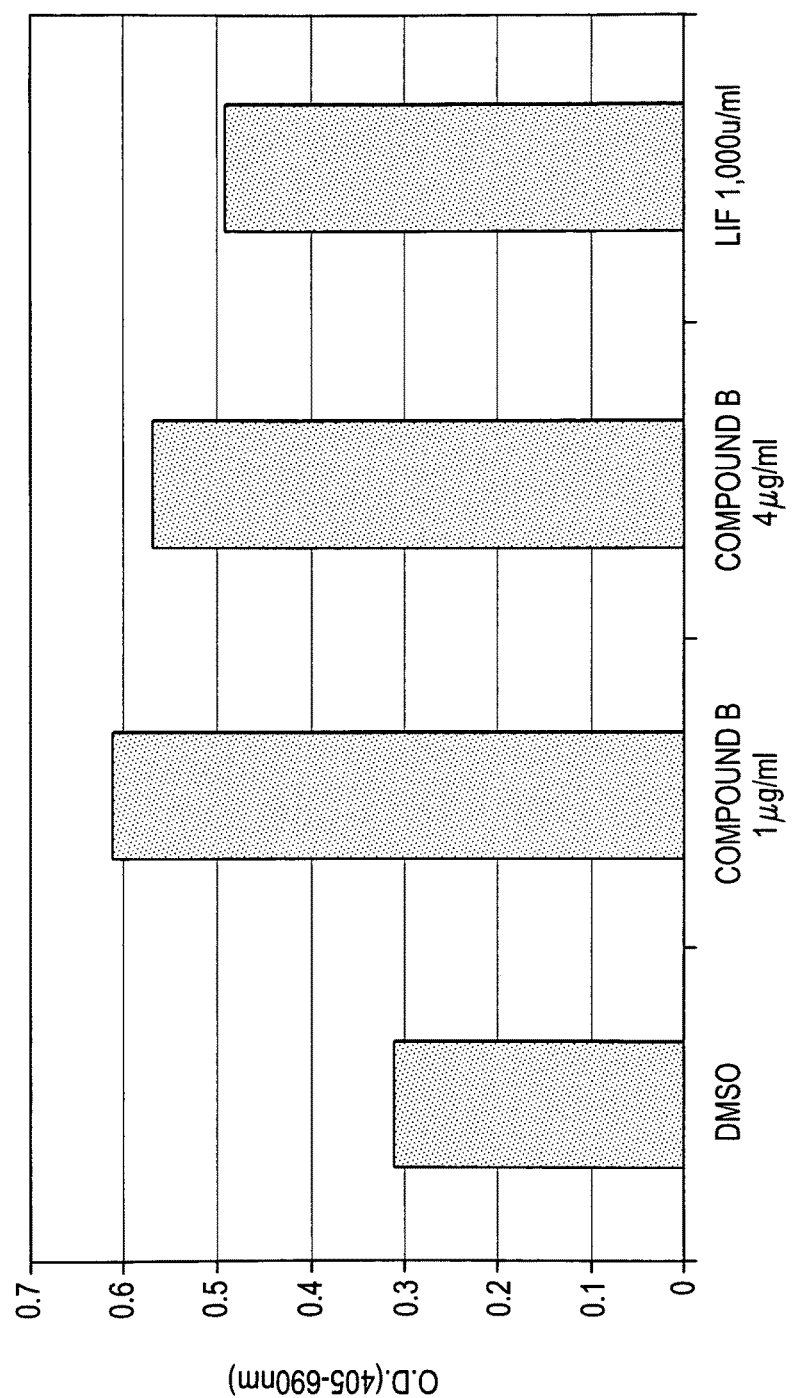
FIG. 13 shows result 1 of ES cell subculture.
Figure 14:
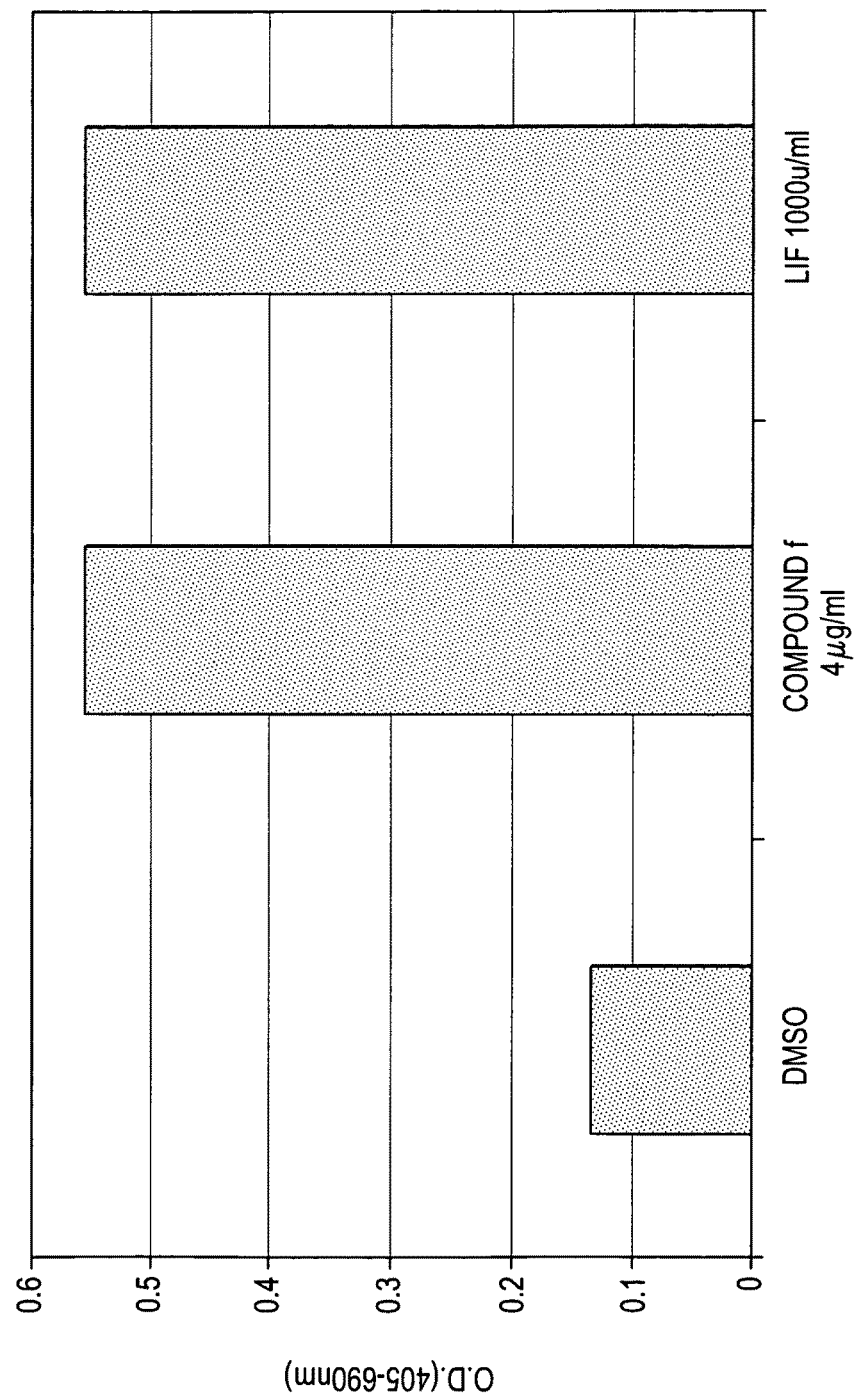
FIG. 14 shows result 2 of ES cell subculture.

The alkaline phosphatase activity of the ES cells cultured for 7 or 30 days by using the differentiation inhibiting agents of the present invention was quantified by applying colony assay. For the ES cells subcultured by the method as described above, $1 \times 10^3$ cells/1 well were seeded on a 96-well cell culture dish (Falcon Corp. made, Cat. No. 3072, USA) coated previously with a 0.1% aqueous gelatin solution to make the ES cell assay medium in 90 μL/1 well. 10 μL of ESGRO diluted with the medium was added to each well to make 0 to $10^3$ units/mL, and culturing was carried out at 37° C. in 5% $CO_2$ incubator for 4 days. The medium was removed by sucking from individual wells, and the cells were washed once with 100 μL of phosphate buffered saline (PBS), and then, 100 μL of p-NPP was added to each well to left stand at room temperature for 10 min. 12.5 μL of a 8 M sodium hydroxide aqueous solution was added to each well to stop the reaction. The absorbance at 405 nm (O.D.405) and absorbance at 690 nm (O.D.690) of the solution were measured by using the spectrophotometer (Molecular Devices Corp. made, type: SPECTRA MAX190), and the value calculated from O.D.405-O.D.690 was determined as the alkaline phosphatase activity. FIG. 13 shows the result of the quantification of the alkaline phosphatase of the ES cells subcultured for 30 days by adding the compound B. FIG. 14 shows the result of the quantification of the alkaline phosphatase of the ES cells subcultured in the medium without serum for 7 days by adding the compound f.

The ES cells subcultured by using the differentiation inhibiting agents of the present invention, the compounds B and f, increased significantly the alkaline phosphatase activity in comparison with the ES cells cultured by using DMSO (0.1%). From this, it is known that the differentiation inhibiting agent of the present invention supported the undifferentiated state of the ES cells even in a long-term culture.

The same examination was carried out for the differentiation inhibiting agents A, C to E and a to o, and the alkaline phosphatase activity was maintained similarly to the differentiation inhibiting agents B and f. It was shown that these differentiation inhibiting agents maintained the undifferentiation state of the ES cell.

Example 5

(1) Culture of Cynomolgus Monkey ES Cells

As the medium for culturing cynomolgus monkey ES cells, DME/F-12, 1:1 (SIGMA D6421) was added with respective factors in the final concentration as presented below to prepare a cynomolgus monkey ES cell culture medium: 20% knockout serum replacement: KSR (Invitrogen Corp. made, 10828-028), 1× nonessential amino acids (SIGMA M7145), 2 mM L-Glutamine (SIGMA G7513), 1 mM sodium pyruvate (SIGMA S8636), 1× penicillin/streptomycin solution (SIGMA P0781). The culture medium for a mouse feeder cell used for culturing cynomolgus monkey ES cells was prepared by adding respective factors to DMEM (Invitrogen Corp. made, 11960-044) in the final concentration shown below: 10% bovine fetus serum (Invitrogen Corp. made), 2 mM L-glutamine (Sigma G7513), 1× penicillin/streptomycin solution (Sigma P0781).

Gelatin (SIGMA Corp. made, Type A: from porcine ESkin, G2500) was dissolved in distilled water in 0.1% concentration, and 5 mL of the thus prepared 0.1% sterilized aqueous gelatin solution was added in a 6 cm-diameter cell culture dish, and then left stand at 37° C. for 30 minutes or longer. The aqueous gelatin solution was removed, and 2×10⁶ mouse embryonic primary culture cell (Invitrogen Corp. made, YE9284400) treated with mitomycin, C (Kyouwa Hakkou Corp. made) was seeded and cultured by using the culture medium for the feeder cell as described above at 37° C. in 5% $CO_2$ incubator (Tabai Espec Corp. made) for 5 hours or longer. The cynomolgus monkey ES cells (Tanabe Seiyaku, K.K. made) was seeded on mouse embryonic primary culture cell, and cultured and proliferated in 5 mL of cynomolgus monkey ES cell culture medium at 37° C. in 5% $CO_2$ incubator for 3 days.

(2) Preparation of Cynomolgus Monkey ES Cells

The cynomolgus monkey ES cells cultured by the method described in (1) culture of cynomolgus monkey ES cells as described above were washed with PBS and, then, a 0.1% collagenase solution (Wako Corp. made, 032-10534) dissolved in DMEM (Invitrogen Corp. made 11960-044), or a trypsin solution (prepared by mixing 10 mL of a 2.5% trypsin solution (Invitrogen Corp. made 15090-046), 20 mL of Knockout Serum Replacement (Invitrogen Corp. made 10828-028), 1 mL of a 100 mM $CaCl_2$ aqueous solution and 69 mL of PBS) was added, and incubation was carried out at 37° C. for 5 minutes. 5 mL of the cynomolgus monkey ES cell culture medium was added, cell colonies were removed by using a small sized pipette and, then, dispersed, transferred to a 15 mL sterilized tube, and centrifuged at 1000 rpm for about 5 minutes by using the micro centrifuge (TOMY SEIKO made) to prepare pellets. The supernatant was removed, and then the cells were suspended again in 5 mL of the fresh ES cell culture medium to obtain the cynomolgus monkey ES cells.

(3) Preparation of Matrigel-Coated Dish

Growth Factor Reduced (GFR) BD Matrigel (Becton Dickinson Japan made, 354230, Japan) and BD Matrigel basement membrane Matrix (Becton Dickinson Japan made, 354234, Japan) were melted at 2 to 8° C. in a refrigerator overnight, and then blended slowly by using a cooled pipette. The Matrigel was diluted 20 folds by using cooled DMEM/F12 1:1 (Sigma Corp. made, D6421, USA), added to a culture dish, and incubated at room temperature for 1 hour. The solution was removed and the residue was washed with DMEM/F12 1:1 to obtain a Matrigel-coated dish.

(4) ES Cell Differentiation Inhibition Assay 6

The cynomolgus monkey ES cells prepared by the method described in (2) preparation of cynomolgus monkey ES cells as described above were diluted 3 to 5 folds by adding the medium, and 4.5 mL (per dish) of the cell solution were seeded on a 6 cm-diameter cell culture dish coated previously with Matrigel (Becton Dickinson Japan made). Subsequently, 0.5 mL of the differentiation inhibiting agent (A to F and a to o) of the present invention and 6-bromoindirubin-3-oxime, which were dissolved in dimethylsulfoxide (DMSO) or culture medium, or their mixture to make 8 to 40 μg/mL per each dish, was added, and culturing was carried out at 37° C. in 5% $CO_2$ incubator. Subculture was carried out for every 2 to 4 days by the method described in (2) preparation of cynomolgus monkey ES cells as described above. The final concentration of DMSO in the culture medium was 0.1% or lower. The cultured cells as described above were evaluated by the alkaline phosphatase staining described in Example 1 as described above.

Figure 15:
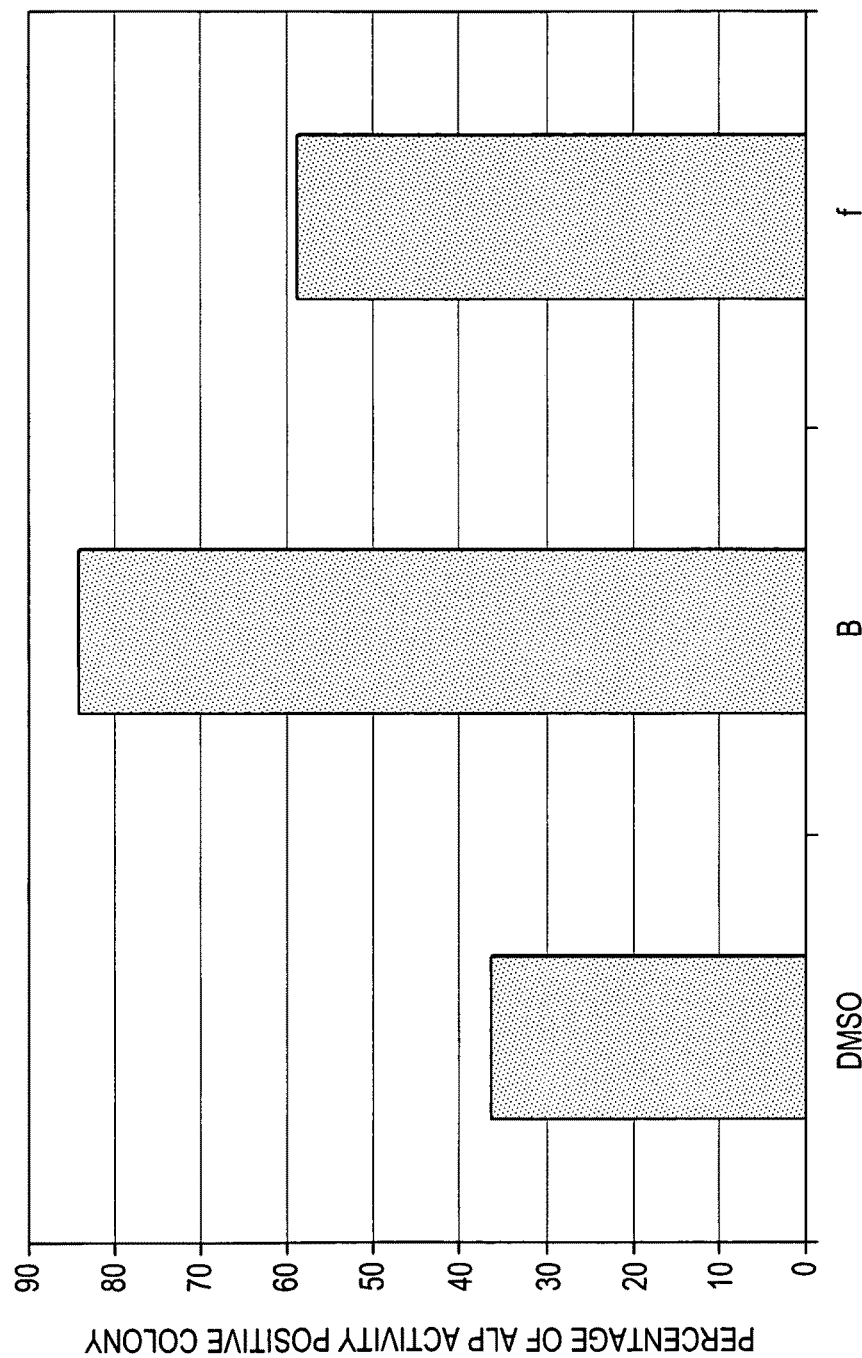
FIG. 15 shows an embryonic stem cell undifferentiation-maintaining effect of the differentiation inhibiting agent according to the present invention.
Figure 16:
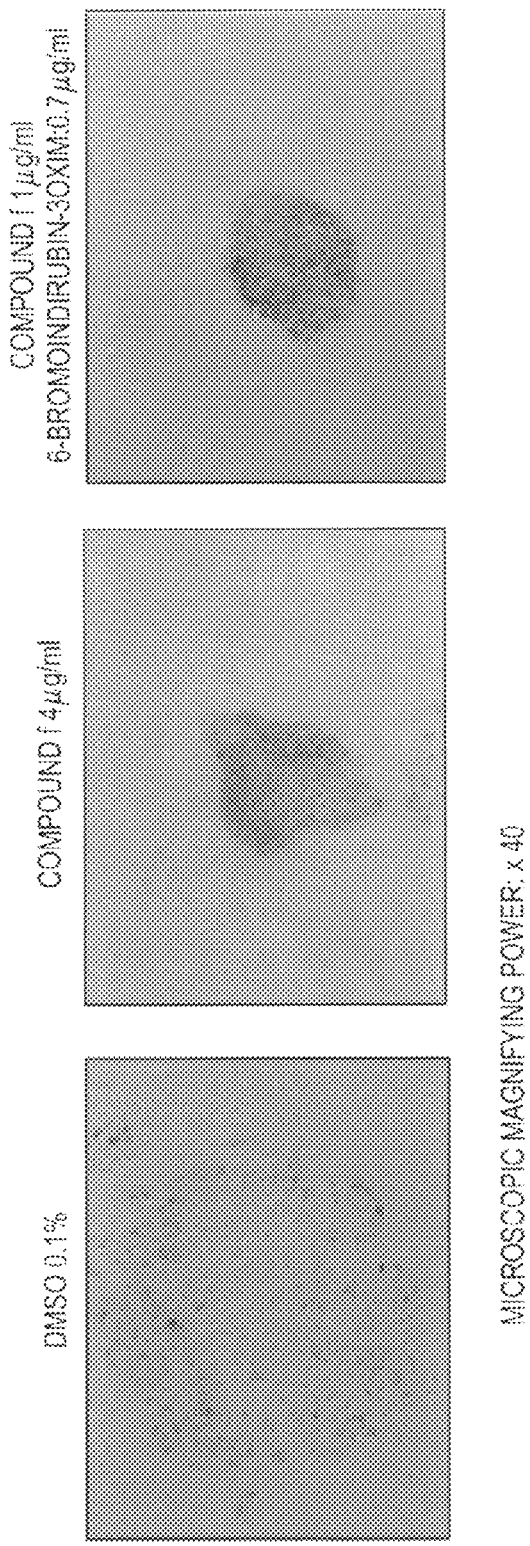
FIG. 16 shows an embryonic stem cell undifferentiation-maintaining effect (staining image) of the differentiation inhibiting agent according to the present invention.

The result of the alkaline phosphatase staining of the cells which were cultured for 2 days after the compound B or the compound f was added is presented in FIG. 15 as a proportion of number of stained colony to number of the total colony, and a photograph of the alkaline phosphatase staining at 3rd day after subculture after 3-day culture by adding the compound f in the absence or the presence of 6-bromoindirubin-3-oxime is shown in FIG. 16.

The cynomolgus monkey ES cells cultured with the differentiation inhibiting agent, the compound B and the compound f, of the present invention showed a significantly higher proportion of colonies stained with alkaline phosphatase, in comparison with the cynomolgus monkey ES cells cultured with DMSO (0.1%). Further, the cynomolgus monkey ES cells subcultured in the presence of the compound f was stained significantly in comparison with the cynomolgus monkey ES cells subcultured in the presence of DMSO. Moreover, in the presence of 6-bromoindirubin-3-oxime, the effect of the compound f was reinforced. From this, it is shown that the differentiation inhibiting agent of the present invention supported the undifferentiated state of the cynomolgus monkey ES cells. The same examination was carried out for the compounds A, C to E, a to e and g to o, and the alkaline phosphatase activity was maintained similarly to the differentiation inhibiting agents B and f. It was shown that these differentiation inhibiting agents maintained the undifferentiation state of the cynomolgus monkey ES cell.

Example 6

Method for Preparing Compounds

[1] Synthesis of 3,3-dimethyl-1,2,3,4-tetrahydroisoquinolinidene-1-acetamide

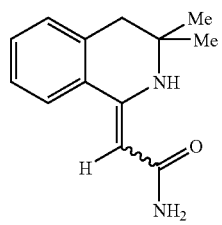 [SMILES: CC1(C)Cc2ccccc2C(=CC(N)=O)N1]

2-cyanoacetamide (Aldrich Corp. made, USA) is added to benzene, and concentrated sulfuric acid is slowly dropped to prevent a rise of the temperature to 10° C. with stirring. The solution is cooled to room temperature, and then dimethylbenzylcarbinol (Lancaster Corp. made, UK) is added. After refluxed for about 30 minutes, the solution is left stand for cooling to room temperature and, then, the reaction mixture is poured into ice water. A water phase extracted is neutralized and the resultant precipitation is filtered. After drying, the precipitation is recrystallized by using isopropanol to obtain the title compound.
MS (m/z)=217(M+1)

[2] Synthesis of 2-(4-acetyl-phenylazo)-2-(3,3-dimethyl-3,4-dihydro-2H-isoquinoline-1-ylidene)-acetamide

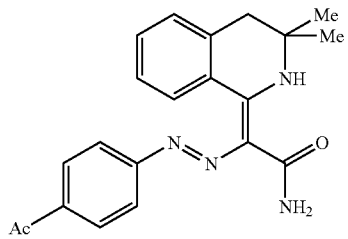 [SMILES: CC(=O)c1ccc(/N=N/C(C(N)=O)=C2/NC(C)(C)Cc3ccccc32)cc1]

p-aminoacetophenon (Aldrich Corp., USA) is added to benzene, and hydrochloric acid gas is passed. The obtained precipitation is filtered and recrystallized with isopropanol to obtain p-aminoacetophenon hydrochloride. The obtained p-aminoacetophenon hydrochloride is dissolved in a 20% aqueous ethanol solution, and made it acidic by adding concentrated hydrochloric acid on an ice bath. An aqueous sodium nitrite solution is dropped and urea treatment is carried out to obtain a diazonium salt solution.
3,3-dimethyl-1,2,3,4-tetrahydroisoquinolinidene-1-acetamide is dissolved in a 20% aqueous ethanol solution, and concentrated hydrochloric acid is added. The temperature is regulated to prevent to exceed 10° C. and the above diazonium salt solution is added. The reaction solution changes, and a saturated aqueous sodium acetate solution is added with stirring. The obtained precipitation is filtered and, then, recrystallized by isopropanol to obtain the title compound.
MS (m/z)=363(M+1)

[3] Synthesis of 2-(3-acetyl-phenylazo)-2-(3,3-dimethyl-3,4-dihydro-2H-isoquinoline-1-ylidene)-acetamide

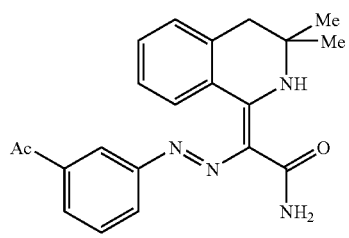 [SMILES: CC(=O)c1cccc(/N=N/C(C(N)=O)=C2/NC(C)(C)Cc3ccccc32)c1]

m-aminoacetophenon (Aldrich Corp., USA) is added to benzene and hydrochloric acid gas is passed. The obtained precipitation is filtered and recrystallized with isopropanol to obtain p-aminoacetophenon hydrochloride. The obtained p-aminoacetophenon hydrochloride is dissolved in a 20% aqueous ethanol solution and made it acidic by adding concentrated hydrochloric acid on an ice bath. An aqueous sodium nitrite solution is dropped, and urea treatment is carried out to obtain a diazonium salt solution.
3,3-dimethyl-1,2,3,4-tetrahydroisoquinolinidene-1-acetamide is dissolved in a 20% aqueous ethanol solution, and concentrated hydrochloric acid is added. The temperature is regulated to prevent to exceed 10° C., and the above diazonium salt solution is added. The reaction solution changes, and a saturated aqueous sodium acetate solution is added by stirring. The obtained precipitation is filtered and, then, recrystallized by isopropanol to obtain the title compound.
MS (m/z)=363(M+1)

[4] Synthesis of 2-(4-acetyl-phenylazo)-2-(2,3,3-trimethyl-3,4-dihydro-2H-isoquinoline-1-ylidene)-acetamide

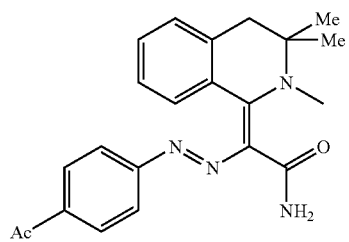

2-(4-acetyl-phenylazo)-2-(3,3-dimethyl-3,4-dihydro-2H-isoquinoline-1-ylidene) acetamide (Asinex Corp., Russia) and sodium carbonate are added to acetonitrile, and an acetonitrile solution of methyl iodide is slowly dropped and refluxed. The refluxed product is cooled to room temperature and, then, the solvent is removed by reducing a pressure; the residue is dissolved in dichloromethane and washed with distilled water. Thereafter, the product is dried with anhydrous sodium sulfate and filtered and, then, the solvent is removed by reducing the pressure. The residue containing the reaction product is purified by column chromatography to obtain the title compound.
MS (m/z)=377(M+1)

[5] Synthesis of 2-(2-acetyl-3,3-dimethyl-3,4-dihydro-2H-isoquinoline-1-ylidene)-2-(4-acetyl-phenylazo)-acetamide

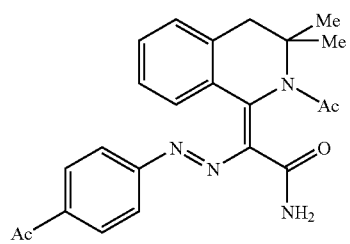 [SMILES: CC(=O)c1ccc(/N=N/C(C(N)=O)=C2\c3ccccc3CC(C)(C)N2C(C)=O)cc1]

2-(4-acetyl-phenylazo)-2-(3,3-dimethyl-3,4-dihydro-2H-isoquinoline-1-ylidene)-acetamide (Asinex Corp., Russia) and dimethylaminopyridine are dissolved in pyridine on the ice bath, and acetic anhydride is added. After the reaction is stopped, the solvent after the reaction as described above is poured on ice water to extract the reaction product by adding dichloromethane. The reaction product is dried by using anhydrous sodium sulfate and filtered and, then, the solvent is removed by reducing the pressure. The residue containing the reaction product is purified by column chromatography to obtain the title compound.

MS (m/z)=405(M+1)

[6] Synthesis of (4-acetyl-phenylazo)-(3,3-dimethyl-3,4-dihydro-2H-isoquinoline-1-ylidene)-acetonitrile

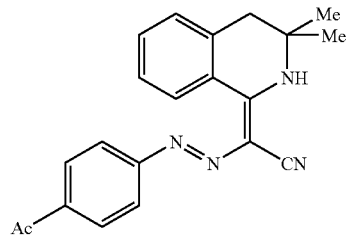 [SMILES: CC(=O)c1ccc(/N=N/C(C#N)=C2/NC(C)(C)Cc3ccccc32)cc1]

2-(4-acetyl-phenylazo)-2-(3,3-dimethyl-3,4-dihydro-2H-isoquinoline-1-ylidene)-acetamide (Asinex Corp., Russia), thionyl chloride and DMF are mixed and stirred slowly. An excess of thionyl chloride is removed from the mixed solvent by reducing the pressure. The residue containing the reaction product is purified by column chromatography to obtain the title compound.

MS (m/z)=345(M+1)

[7] Synthesis of (4-acetyl-phenylazo)-(3,3-dimethyl-3,4-dihydro-2H-isoquinoline-1-ylidene)-acetic acid

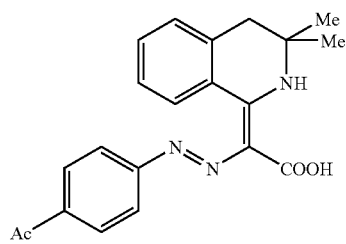 [SMILES: CC(=O)c1ccc(/N=N/C(C(=O)O)=C2/NC(C)(C)Cc3ccccc32)cc1]

Potassium hydroxide and 2-(4-acetyl-phenylazo)-2-(3,3-dimethyl-3,4-dihydro-2H-isoquinoline-1-ylidene)-acetamide (Asinex Corp., Russia) are added to ethanol, and the mixture is refluxed under heating. The refluxed product is cooled to room temperature and, then, added with distilled water, and further added with hydrochloric acid to make the pH neutral, followed by extracting the reaction product with diethylether. The reaction product is dried by using anhydrous sodium sulfate and filtered and, then, the solvent is removed by reducing the pressure. The residue containing the reaction product is purified by column chromatography to obtain the title compound.

MS (m/z)=364(M+1)

[8] Synthesis of (4-acetyl-phenylazo)-(3,3-dimethyl-3,4-dihydro-2H-isoquinoline-1-ylidene)-acetic acid ethyl ester

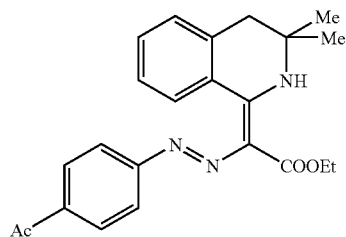 [SMILES: CCOC(=O)C(/N=N/c1ccc(C(C)=O)cc1)=C1\NC(C)(C)Cc2ccccc21]

(4-acetyl-phenylazo)-(3,3-dimethyl-3,4-dihydro-2H-isoquinoline-1-ylidene)-acetic acid is suspended on ethanol, and the mixture is stirred. Thionyl chloride is dropped slowly in the solution with cooling and, then, stirred at room temperature. The solvent is removed by reducing the pressure and the residue is washed with water. The reaction product is dried with anhydrous sodium sulfate and filtered and, then, the solvent is removed by reducing the pressure. The residue containing the reaction product is purified by column chromatography to obtain the title compound.

MS (m/z)=392(M+1)

[9] Synthesis of 2-(4-acetyl-phenylazo)-2-(3,3-dimethyl-3,4-dihydro-2H-isoquinoline-1-ylidene)-N-methyl-acetamide

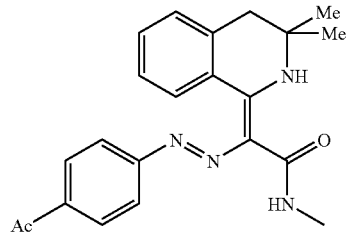 [SMILES: CNC(=O)C(/N=N/c1ccc(C(C)=O)cc1)=C1\NC(C)(C)Cc2ccccc21]

(4-acetyl-phenylazo)-(3,3-dimethyl-3,4-dihydro-2H-isoquinoline-1-ylidene)-acetic acid, methylamine, HOBt (Advanced ChemTech Corp., USA) and triethylamine are dissolved in DMF, and a dichloromethane solution of HBTU (Advanced ChemTech Corp., USA) is added thereto. The mixture is then stirred at room temperature. The mixture is washed with a saturated aqueous sodium chloride solution and a 5% aqueous sodium hydrogen carbonate solution. The reaction product is dried with anhydrous sodium sulfate and filtered and, then, the solvent is removed by reducing the pressure. The residue containing the reaction product is purified by column chromatography to obtain the title compound.

MS (m/z)=377(M+1)

[10] Synthesis of 2-(4-acetyl-phenylazo)-2-(3,3-dimethyl-3,4-dihydro-2H-isoquinoline-1-ylidene)-N,N-dimethyl-acetamide

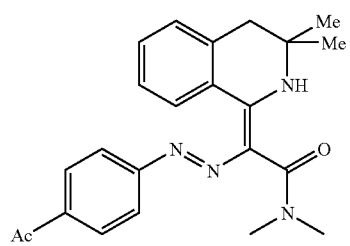 [SMILES: CC(=O)c1ccc(/N=N/C(C(=O)N(C)C)=C2/NC(C)(C)Cc3ccccc32)cc1]

(4-acetyl-phenylazo)-(3,3-dimethyl-3,4-dihydro-2H-isoquinoline-1-ylidene)-acetic acid, dimethylamine, HOBt (Advanced ChemTech Corp., USA) and triethylamine are dissolved in DMF, a dichloromethane solution of HETU (Advanced ChemTech Corp., USA) is added, and then the mixture is stirred at room temperature. The stirred and blended solvent is washed with a saturated aqueous sodium chloride solution and a 5% aqueous sodium hydrogen carbonate solution. The reaction product is dried with anhydrous sodium sulfate and filtered and, then, the solvent is removed by reducing the pressure. The residue containing the reaction product is purified by column chromatography to obtain the title compound.

MS (m/z)=391 (M+1)

[11] Synthesis of 2-(4-acetyl-phenylazo)-2-(3,3-dimethyl-3,4-dihydro-2H-isoquinoline-1-ylidene)-N-phenyl-acetamide

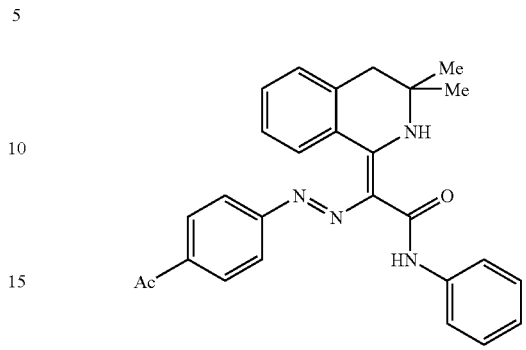

(4-acetyl-phenylazo)-(3,3-dimethyl-3,4-dihydro-2H-isoquinoline-1-ylidene)-acetic acid, phenylamine, HOBt (Advanced ChemTech Corp., USA) and triethylamine are dissolved in DMF, a dichloromethane solution of HBTU (Advanced ChemTech Corp., USA) is added, and then the mixture is stirred at room temperature. The mixture is washed with the saturated aqueous sodium chloride solution and a 5% aqueous sodium hydrogen carbonate solution. The reaction product is dried with anhydrous sodium sulfate and filtered and, then, the solvent is removed by reducing the pressure. The residue containing the reaction product is purified by column chromatography to obtain the title compound.

MS (m/z)=439(M+1)

[12] Synthesis of 2-(4-acetyl-phenylazo)-2-(3,3-dimethyl-1,2,3,4-tetrahydro-isoquinoline-1-yl)-acetamide

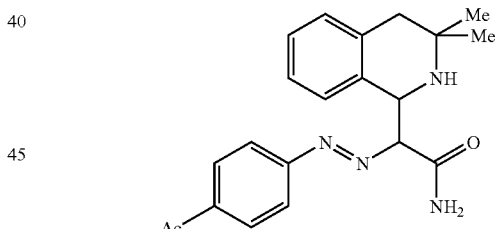

In a nitrogen atmosphere, 2-(4-acetyl-phenylazo)-2-(3,3-dimethyl-3,4-dihydro-2H-isoquinoline-1-ylidene)-acetamide (Asinex Corp., Russia) is dissolved in acetonitrile, and the obtained product is added with xylene in which triphenyl tin hydride (Aldrich, Corp., USA) is dissolved, and the mixture is refluxed. The refluxed product is cooled to room temperature and an insoluble matter is separated by filtration. The solvent is removed from the filtrate by reducing the pressure. The residue containing the reaction product is purified by column chromatography to obtain the title compound.

MS (m/z)=365(M+1)

Example 7

(1) ES Cell Differentiation Inhibition Assay 7

Figure 17:
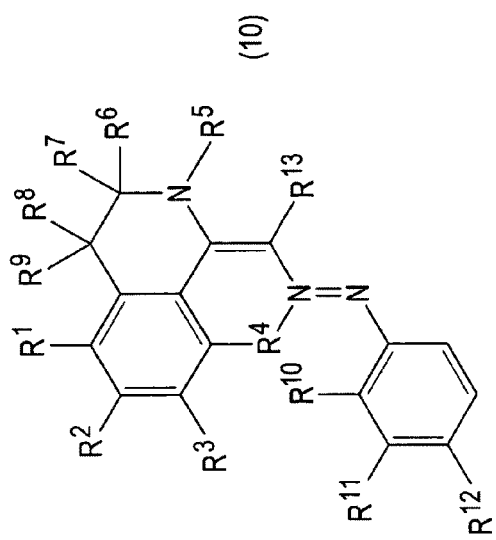
FIG. 17 shows structure of compound 1̂ according to the present invention. For compounds 1̂, $R^1$ to $R^{13}$ of formula (10) in FIG. 17 are represented by groups or elements presented in the table below.

D3ES cells cultured by using the method described in (2) culturing the mouse ES cell of Example 1 was washed twice with PBS, and then a 0.25% trypsin solution (Invitrogen Corp. made) was added and incubated at 37° C. for 5 minutes to remove the colony of the undifferentiated D3ES cells from the feeder. The 5 mL-ES cell culture medium was added, the cell colonies were dispersed by using a pipette with a small diameter and transferred to a 15 mL-sterilized tube, and centrifuged at 800 rpm for about 5 minutes by using the table centrifuge (TOMY SEIKO K.K.) to make pellets. The supernatant was discarded, cells were suspended again in a 5 mL fresh ES cell culture medium and seeded on a 10 cm-diameter dish for cell culture, which had been previously coated with a 0.1% gelatin aqueous solution, and incubated at 37° C. for 20 minutes. After 20 minutes, the culture medium containing floating cells was collected by using a pipette, transferred to a 15 mL-sterilized tube, centrifuged at 1000 rpm for about 5 minutes by using the table centrifuge to make the pellets. Then, the supernatant was removed followed by suspending again in a 5 mL-ES cell assay medium. $3 \times 10^2$ to $1 \times 10^3$ cells/well were seeded on a 24-well cell culture dish (Falcon Corp. made, Cat. No. 3047, USA), which had been coated previously with a 0.1% aqueous gelatin solution, to make the ES cell assay medium in 500 µL/1 well. 50 µL of the compounds $\hat{1}$ to $\hat{10}$, which were prepared by the method described in Example 6, dissolved in dimethylsulfoxide (DMSO) or water, or their mixture to make 0.4 to 40 µg/mL per each well, or ESGRO was added, and culturing was carried out at 37° C. in 5% $CO_2$ incubator for 7 days. The final concentration of DMSO in the culture medium was 0.1% or lower. In a control well, only DMSO was added to make the final concentration of 0.1%. The structure of the compound $\hat{1}$ is presented in FIG. 17, and the structures of the compounds $\hat{2}$ to $\hat{10}$ are presented in FIG. 18.

(2) Alkaline Phosphatase Staining

Figure 19:
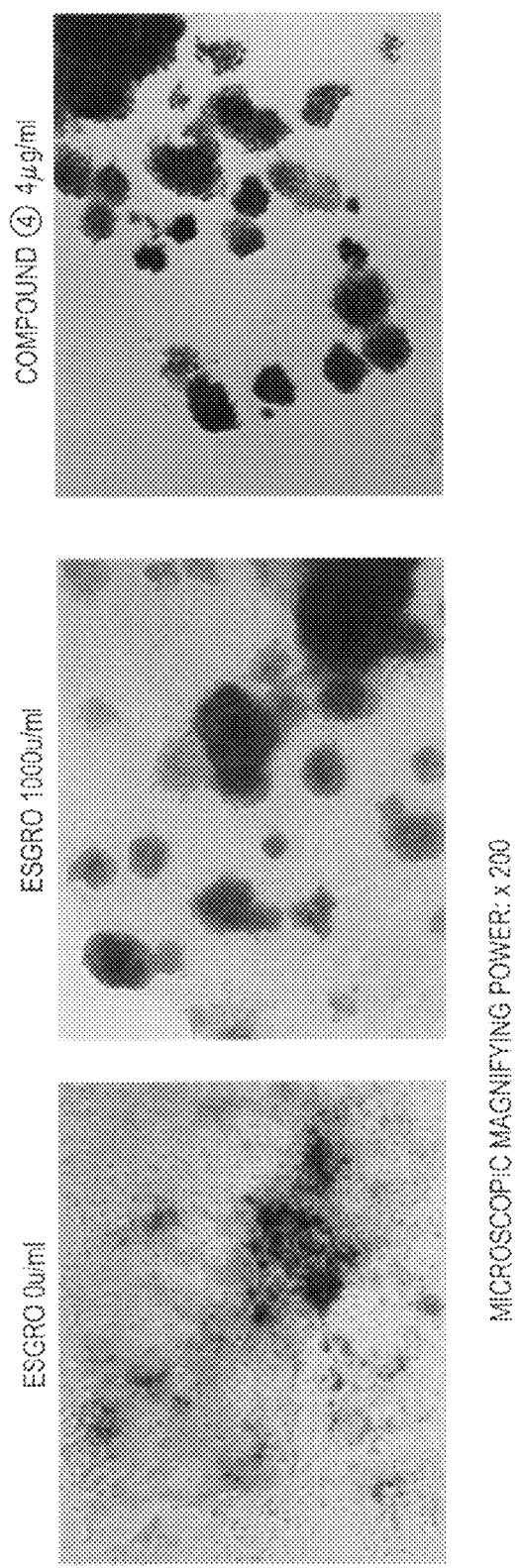
FIG. 19 shows a staining image of alkaline phosphatase staining.

The ES cells were stained by using an alkaline phosphatase kit (SIGMA Diagnostic Corp. made, Cat. No. 86-R). The medium was removed by sucking from individual wells of the ES cells cultured by the method described in the "ES cell differentiation inhibitor assay" as described above, and the cells were washed once with 0.5 mL of phosphate buffered saline (PBS) and, then, 0.5 mL of a cell-fixing solution (25 mL citric acid solution (SIGMA Corp. made, Cat. No. 91-5), 65 mL acetone and 8 mL 37% formaldehyde) was added to each well, and the cells were left stand at room temperature for 30 seconds. The fixing solution was removed by sucking, and 0.5 mL of deionized water was added to individual wells and left stand at room temperature for 45 seconds. The deionized water was removed by sucking and, then, 0.5 mL of an alkaline phosphatase staining solution (1 mL sodium nitrite solution, 1 mL Fast Red Violet LB salt solution, 1 mL naphthol AS-BI alkaline solution and 45 mL distilled water) was added to each well and left stand at room temperature for 15 minutes followed by removal of the staining solution by sucking, and washing was carried out with 0.5 mL of deionized water. Staining images were compared among the ES cells as the negative control cultured in the absence of ESGRO, the ES cells as the positive control cultured in the presence of ESGRO (1000 units/mL), and the ES cells cultured in the presence of the compound $\hat{4}$ (4 µg/mL) of the present invention (refer to FIG. 19). The ES cells cultured in the presence of the compound $\hat{4}$ was, in comparison with the ES cells cultured in the absence of ESGRO, were stained significantly more densely, showing that the ES cells have a high alkaline phosphatase activity. Moreover, the compound of the present invention also allowed the cells to form the undifferentiated colony equal to that of the ES cells cultured in the presence of ESGRO being the positive control. From this result, the compound of the present invention supported strongly proliferation of the ES cells in the undifferentiated state.

In the case of the compounds $\hat{1}$ to $\hat{3}$ and $\hat{5}$ to $\hat{10}$, similar staining was observed as in the case of the compound $\hat{4}$.

INDUSTRIAL APPLICABILITY

According to the present invention, the stem cell, preferably the embryonic stem cell, can be safely proliferated with keeping the undifferentiated state in a prolonged period or endlessly in a large quantity. The differentiation inhibiting agent, the culture method by using the same, and the culture liquid, which are provided by the present invention, can be applied to produce the stem cell, preferably the embryonic stem cell, as a cell source of uses for cell transplantation. In addition to many benefits provided by using the stem cell, preferably the embryonic stem cell, the differentiation inhibiting agent and the culture method by using the same, which are provided by the present invention, can be applied to produce the embryonic stem cell having 1 or more genetic modifications. The application includes, for example, developing a cell-based model related to a disease and developing a tissue specified to transplantation for treating a genetic disease, however, is not restricted to them.

As described above, the differentiation inhibiting agent and/or the bicyclic compounds of the present invention can proliferate the stem cell in the undifferentiated state and, as the result, cells and tissues cultured can be preferably used for regeneration medical field. In addition, the compound can be applied to a pharmaceutical composition.

The contents of Japanese Patent Application dated Jun. 27, 2003 (Application No. 2003-185398) and Japanese Patent Application dated Oct. 14, 2003 (Application No. 2003-353870), which are the basis of the priority claimed by the present application, are all incorporated herein by reference as a part of the disclosure of the present specification.

The invention claimed is:

1. A culture medium comprising a basic medium for animal cell culture and a stem cell differentiation inhibiting agent which comprises a low molecular weight compound represented by formula (6) or a salt thereof as an active ingredient,

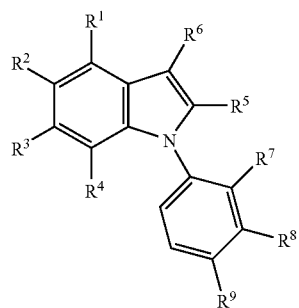

(6)

wherein $R^1$ and $R^2$ are hydrogen atoms; $R^3$ is a hydroxyl group or an acetoxy group; $R^4$ is an acetoxy alkyl group, a cyclic alkylaminoalkyl group which may contain an oxygen atom, a dialkylaminoalkyl group, a hydroxyalkylaminoalkyl group or a hydrogen atom; $R^5$ is a lower alkyl group or an arylaminovinyl group; $R^6$ is a nitro group; $R^7$, $R^8$ and $R^9$ may be the same or different, each representing a lower alkyl group, a lower alkoxy group or a hydrogen atom.

2. The culture medium according to claim 1, wherein a concentration of the compound or the salt thereof ranges from 10 ng/mL to 100 μg/mL.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: The forward primer used for amplifying murine
      Oct-3/4 gene by PCR

<400> SEQUENCE: 1

```
ggcgttctct ttggaaaggt gttc                                          24

<210> SEQ ID NO 2
<211> LENGTH: 20
<212> TYPE: DNA
<213> ORGANISM: Artificial Sequence
<220> FEATURE:
<223> OTHER INFORMATION: The reverse primer used for amplifying murine
      Oct-3/4 gene by PCR

<400> SEQUENCE: 2
ctcgaaccac atccttctct                                               20

<210> SEQ ID NO 3
<211> LENGTH: 22
<212> TYPE: DNA
<213> ORGANISM: Artificial Sequence
<220> FEATURE:
<223> OTHER INFORMATION: The forward primer used for amplifying murine
      GAPDH gene by PCR

<400> SEQUENCE: 3
ggtgaaggtc ggtgtgaacg ga                                            22

<210> SEQ ID NO 4
<211> LENGTH: 22
<212> TYPE: DNA
<213> ORGANISM: Artificial Sequence
<220> FEATURE:
<223> OTHER INFORMATION: The reverse primer used for amplifying murine
      GAPDH gene by PCR

<400> SEQUENCE: 4
tgttagtggg gtctcgctcc tg                                            22

<210> SEQ ID NO 5
<211> LENGTH: 24
<212> TYPE: DNA
<213> ORGANISM: Artificial Sequence
<220> FEATURE:
<223> OTHER INFORMATION: The forward primer used for amplifying murine
      Nanog gene by PCR

<400> SEQUENCE: 5
agggtctgct actgagatgc tctg                                          24

<210> SEQ ID NO 6
<211> LENGTH: 24
<212> TYPE: DNA
<213> ORGANISM: Artificial Sequence
<220> FEATURE:
<223> OTHER INFORMATION: The reverse primer used for amplifying murine
      Nanog gene by PCR

<400> SEQUENCE: 6
caaccactgg tttttctgcc accg                                          24
```